(12) United States Patent
Kirshenbaum et al.

(10) Patent No.: US 9,969,773 B2
(45) Date of Patent: May 15, 2018

(54) POLYMERS, PHARMACEUTICAL COMPOSITIONS AND METHODS OF SYNTHESIZING THE SAME

(71) Applicants: Kent Kirshenbaum, New York, NY (US); Paul Levine, Somerville, MA (US); Timothy Craven, Randolph, NJ (US)

(72) Inventors: Kent Kirshenbaum, New York, NY (US); Paul Levine, Somerville, MA (US); Timothy Craven, Randolph, NJ (US)

(73) Assignee: NEW YORK UNIVERSITY, New York, NY (US)

( * ) Notice: Subject to any disclaimer, the term of this patent is extended or adjusted under 35 U.S.C. 154(b) by 0 days. days.

(21) Appl. No.: 14/688,026

(22) Filed: Apr. 16, 2015

(65) Prior Publication Data
US 2015/0299254 A1    Oct. 22, 2015

Related U.S. Application Data

(60) Provisional application No. 61/980,255, filed on Apr. 16, 2014.

(51) Int. Cl.
| | |
|---|---|
| *C07K 7/06* | (2006.01) |
| *C07K 17/08* | (2006.01) |
| *C07K 7/08* | (2006.01) |
| *C07K 14/00* | (2006.01) |
| *C07K 5/117* | (2006.01) |
| *C07K 5/078* | (2006.01) |
| *C07K 5/097* | (2006.01) |

(52) U.S. Cl.
CPC ............ *C07K 7/06* (2013.01); *C07K 5/06165* (2013.01); *C07K 5/0823* (2013.01); *C07K 5/1024* (2013.01); *C07K 7/08* (2013.01); *C07K 14/001* (2013.01); *C07K 17/08* (2013.01)

(58) Field of Classification Search
CPC .. C07K 14/001; C07K 17/08; C07K 5/06165; C07K 5/0823; C07K 5/1024; C07K 7/06; C07K 7/08
See application file for complete search history.

(56) References Cited

U.S. PATENT DOCUMENTS

2012/0253011 A1    10/2012  Li et al.

FOREIGN PATENT DOCUMENTS

WO    2011017837    2/2011

OTHER PUBLICATIONS

Kling, "PEGYlation of Biologics", BioProcess International, 2013, 11:35-43.

Yoshimoto et al, "PEGylated protein separations: challenges and opportunities", Biotechnol. J., 2012, 7:592-593.
Levine et al, Chemoselective fragment condensation between peptide and peptidomimetic oligomers:, Org. Biomol. Chem., 2013, 11:4142-4146.
Dumas et al, "Self-liganded Suzuki-Miyaura coupling for site-selective protein PEGylation", Angew. Chem. Int. Ed., 2013, 52, 3916-3921.
Li et al, "Copper-free Sonogashira cross-coupling for functionalization of alkyne-encoded proteins in aqueous medium and in bacterial cells", J. Am. Chem. Soc., 2011, 133:15316-15319.
Zhou et al, "Comparison of site-specific PEGylations of the N-terminus of interferon beta-1b: selectivity, efficiency, and in vivo/vitro activity", Bioconj. Chem., 2014, 25:138-146.
Wendeler et al, "Enhanced catalysis of oxime-based bioconjugations by substituted anilines", Bioconj. Chem., 2014, 25:93-101.
Obermeyer et al, "Mild bioconjugation through the oxidative coupling of ortho-aminophenols and anilines with ferricyanide", Angew. Chem. Int. Ed., 2014, 53:1057-1061.
Li et al, Salicylaldehyde Ester-Induced Chemoselective Peptide Ligations: Enabling Generation of Natural Peptidic Linkages at the Serine/Threonine Sites, Organic Letters, 2010, 8:1724-1727.
Toda et al, "Rapid, stable, chemoselective labeling of thiols with Julia-Kocieński-like reagents: a serum-stable alternative to maleimide-based protein conjugation", Angew. Chem. Int. Ed., 2013, 52:12592-12596.
Marsac et al, "Site-specific attachment of polyethylene glycol-like oligomers to proteins and peptides", Bioconj. Chem., 2006, 17:1492-1498.
Alconcel et al, "FDA-approved poly(ethylene glycol)-protein conjugate drugs", Polym. Chem., 2011, 2:1442-1448.
Fee et al, "PEG-proteins: Reaction engineering and separation issues", Chem. Eng. Sci., 2006, 61:924-939.
Rashidian et al, "Chemoenzymatic reversible immobilization and labeling of proteins without prior purification", J. Am. Chem. Soc., 2012, 134:8455-8467.
Jones et al, "Direct Peptide Bioconjugation/PEGylation at Tyrosine with Linear and Branched Polymeric Diazonium Salts", J. Am. Chem. Soc., 2012, 134:7406-7413.
Ban et al, "Facile and Stable Linkages through Tyrosine: Bioconjugation Strategies with the Tyrosine-Click Reaction", Bioconj. Chem., 2013, 24:520-532.

(Continued)

*Primary Examiner* — Pancham Bakshi
*Assistant Examiner* — Mark R Luderer
(74) *Attorney, Agent, or Firm* — Klauber & Jackson LLC

(57) ABSTRACT

Novel methods to prepare novel polymers are disclosed. Oxazolidinyl compounds according to formula IV:

IV

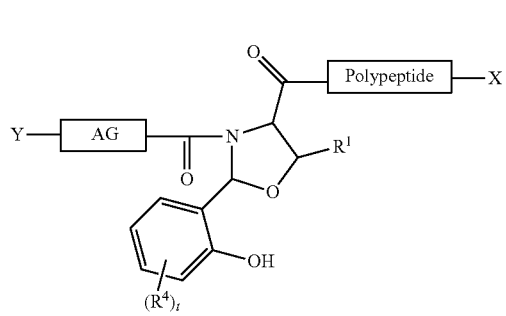

are also disclosed as intermediate compounds that can be reacted with an acid to form a polymer of formula I.

28 Claims, 64 Drawing Sheets

(56) References Cited

OTHER PUBLICATIONS

Fee et al, "Protein Purification, Principles, High Resolution Methods, and Applications, Third Edition, Purification of PEGylated Proteins", John Wiley & Sons, Inc., J. Janson (Editor), Hoboken, 2011, 339-362.
Levine et al, "Semisynthesis of Peptoid-Protein Hybrids by Chemical Ligation at Serine", Org. Lett., 2014, 16:512-515.
Zhang et al, "Protein chemical synthesis by serine and threonine ligation", Proceedings of the National Academy of Sciences of the United States of America, 2013, 110:6657-6662.
Van Cauwenberghe et al, "Analytical characterizaton challenges of PEGylated peptides", 2000 Eli Lilly and Company.
Liu et al., "Development and application of serine/threonine ligation for synthetic protein chemistry", Org Biomol Chem, 2014, 12:3768-3773.

Figure 2
2A
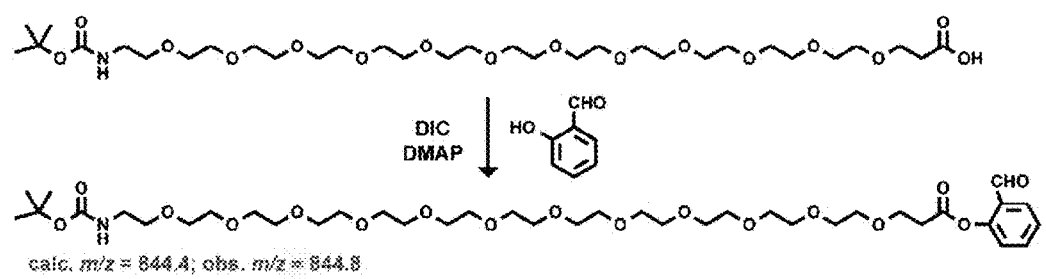
calc. m/z = 844.4; obs. m/z = 844.8
2B
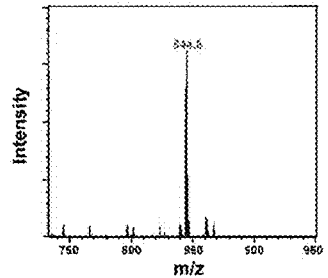

2C

Figure 3 (cont)
3D
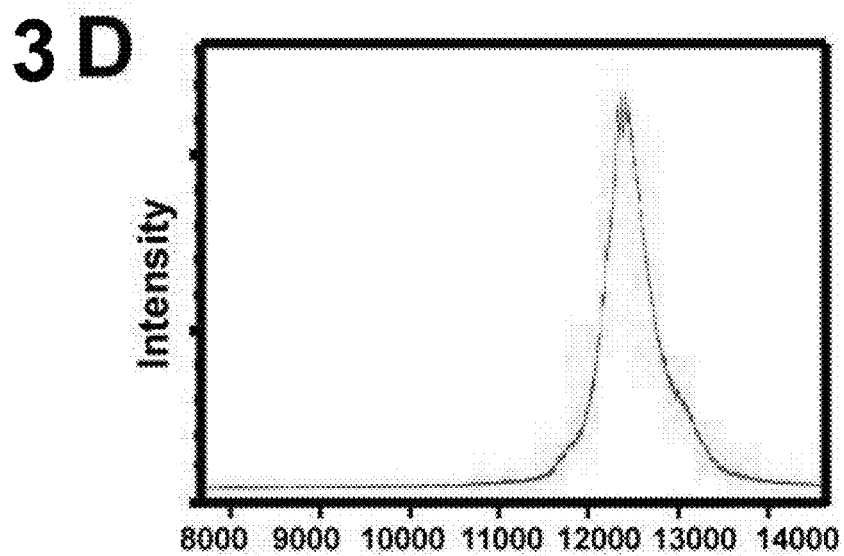
3E
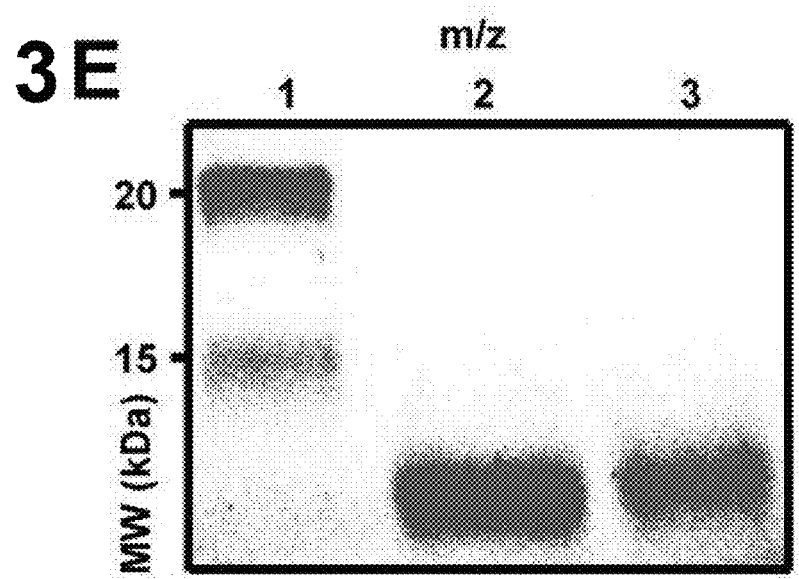

3F

Figure 4 (cont)
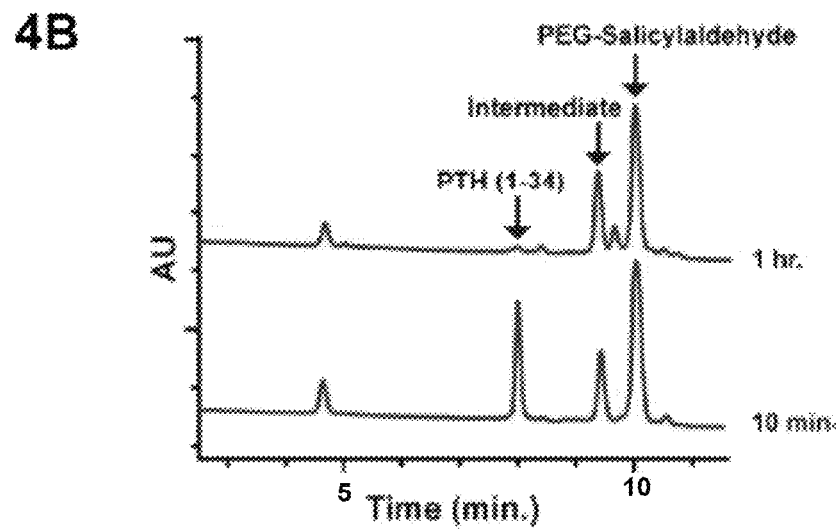
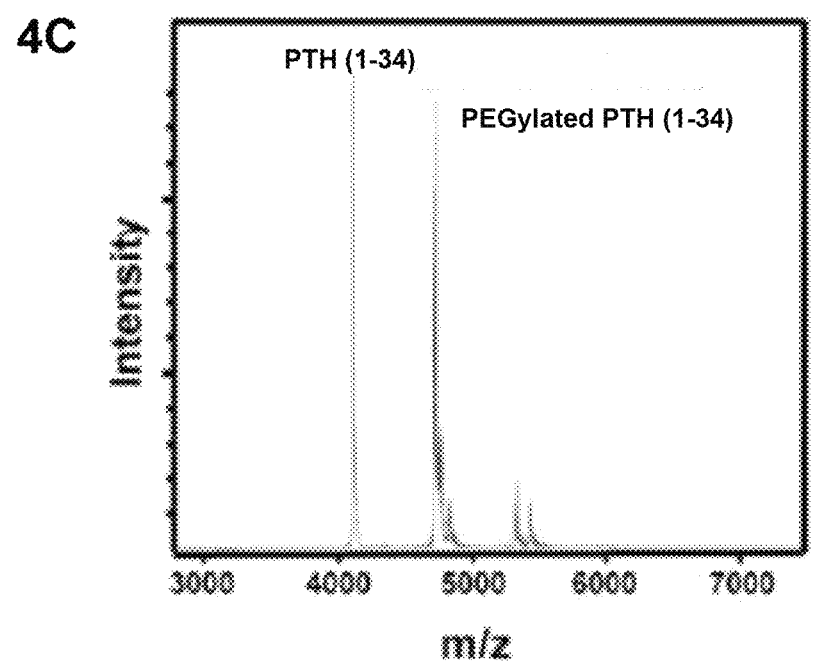

Figure 5

Excluded Compound 1
CAS Registry Number: 1379581-54-0 ($C_{76}H_{124}N_{18}O_{31}$)
Name not available Excluded Compound 2
CAS Registry Number: 1353563-96-8
($C_2H_4O)_n C_{147}H_{235}N_{41}O_{50}$
Name - Poly(oxy-1,2-ethanediyl), α-(2-aminoethyl)-ω-hydroxy-, 1'-ether with L-seryl-L-asparaginyl-L-threonyl-L-seryl-L-α-glutamyl-L-seryl-L-phenylalanyl-$N^6$-[N-(3-hydroxy-1-oxopropyl)-L-seryl-L-asparaginyl-L-threonyl-L-seryl-L-α-glutamyl-L-seryl-L-phenylalanyl]-L-lysine-L-phenylalanyl-L-arginyl-L-valyl-L-threonyl-L-glutaminyl-L-leucyl-L-alanyl-L-prolyl-L-lysyl-L-alanyl-L-glutaminyl-L-isoleucyl-L-lysyl-L-α-glutamine
Polymer Excluded Compound 3
CAS Registry Number: 1254174-69-0
($C_2H_4O)_n C_{80}H_{118}N_{24}O_{19}$
Name - Poly(oxy-1,2-ethanediyl), α-[2-[(2-hydrazinylacetyl)amino]ethyl]-ω-hydroxy-, $1^N$-ether with N-(3-hydroxy-1-oxopropyl)-L-seryl-L-tyrosyl-L-seryl-L-norleucylglycyl-L-histidyl-L-phenylalanyl-L-arginyl-L-tryptophylglycyl-L-lysyl-L-prolyl-L-valinamide
Polymer Excluded Compound 4
CAS Registry Number: 1254174-68-9
($C_2H_4O)_n C_{83}H_{122}N_{24}O_{21}$
Name - Poly(oxy-1,2-ethanediyl), α-[2-[(2-hydrazinylacetyl)amino]ethyl]-ω-hydroxy-, $1^N$-ether with N-(3-hydroxy-1-oxopropyl)-L-seryl-L-tyrosyl-L-seryl-L-norleucyl-L-α-glutamyl-L-histidyl-D-phenylalanyl-L-arginyl-L-tryptophylglycyl-L-lysyl-L-prolyl-L-valinamide
Polymer Excluded Compound 5
CAS Registry Number: 1242240-17-0
$C_{51}H_{74}N_8O_{17}$
Name - L-Threoninamide, 3-(5,12-dihydro-12-oxobenz[b]acridin-2-yl)-L-alanyl-21-amino-4,7,10,13,16,19-hexaoxaheneicosanoyl-L-threonyl-L-threonyl-L-threonyl-

Figure 5 (cont)

Excluded Compound 6

CAS Registry Number: 1242240-03-4

$C_{43} H_{64} N_8 O_{17}$

Name - L-Serinamide, 3-(9,10-dihydro-9-oxo-2-acridinyl)-L-alanyl-21-amino-4,7,10,13,16,19-hexaoxaheneicosanoyl-L-seryl-L-seryl-L-seryl- Excluded Compound 7

CAS Registry Number: 1199579-48-0

$C_{37} H_{51} N_5 O_{12}$

Name not available

Excluded Compound 8

CAS Registry Number: 1199579-43-5

$C_{78} H_{124} N_9 O_{30} P$

Name not available

Excluded Compound 9

CAS Registry Number: 1189539-31-8

$C_{141} H_{219} N_{32} O_{53} P S_5$

Name - L-Cysteinamide, N-[21-[4-[(2,4-diamino-5-pyrimidinyl)methyl]-2,6-dimethoxyphenoxy]-1,17-dioxo-4,7,10,13-tetraoxa-16-azaheneicos-1-yl]-L-seryl-L-α-aspartylglycylglycyl-L-tyrosyl-L-methionyl-L-α-aspartyl methionyl-L-seryl-L-lysyl-L-α-aspartyl-L-α-glutamyl-L-seryl-L-valyl-L-α-aspartyl-O-phosphono-L-tyrosyl-L-valyl-L-prolyl-L-methionyl-L-leucyl-L-α-aspartyl-L-methionyl-L-lysyl- Excluded Compound 10

CAS Registry Number: 1189539-30-7

$C_{141} H_{219} N_{32} O_{53} P S_5$

Name - L-Cysteinamide, N-[21-[4-[(2,4-diamino-5-pyrimidinyl)methyl]-2,6-dimethoxyphenoxy]-1,17-dioxo-4,7,10,13-tetraoxa-16-azaheneicos-1-yl]-L-seryl-L-α-aspartylglycylglycyl-O-phosphono-L-tyrosyl-L-methionyl-L-α-aspartyl-L-methionyl-L-seryl-L-lysyl-L-α-aspartyl-L-α-glutamyl-L-seryl-L-valyl-L-α-aspartyl-L-tyrosyl-L-valyl-L-prolyl-L-methionyl-L-leucyl-L-α-aspartyl-L-methionyl-L-lysyl- Excluded Compound 11

CAS Registry Number: 1189539-29-4

Name - L-Cysteinamide, N-[21-[4-[(2,4-diamino-5-pyrimidinyl)methyl]-2,6-dimethoxyphenoxy]-1,17-dioxo-4,7,10,13-tetraoxa-16-azaheneicos-1-yl]-L-seryl-L-α-aspartylglycylglycyl-O-phosphono-L-tyrosyl-L-methionyl-L-α-aspartyl-L-methionyl-L-seryl-L-lysyl-L-α-aspartyl-L-α-glutamyl-L-seryl-L-valyl-L-α-aspartyl-O-phosphono-L-tyrosyl-L-valyl-L-prolyl-L-methionyl-L-leucyl-L-α-aspartyl-L-methionyl-L-lysyl- Excluded Compound 12

CAS Registry Number: 942119-12-2

$C_{76} H_{123} N_{14} O_{19} P$

Name - L-Lysinamide, N-(14-hydroxy-14-oxido-1-oxo-4,7,10,13,15-pentaoxa-14-phosphahentriacont-1-yl)-L-seryl-L-norleucyl-L-α-glutamyl-(4R)-4-hydroxy-L-prolyl-D-phenylalanyl-L-arginyl-L-tryptophyl-, (3→8)-lactam Excluded Compound 13

CAS Registry Number: 872611-89-7

$C_{69} H_{82} N_8 O_{28}$

Name - 5,12-Naphthacenedione, 7,8,9,10-tetrahydro-6,8,11-trihydroxy-8-(2-hydroxyacetyl)-1-methoxy-10-[[2,3,6-trideoxy-3-[[N-[3-[2-[2-[2-(2,5-dihydro-2,5-dioxo-1H-pyrrol-1-yl)ethoxy]ethoxy]ethoxy]-1-oxopropyl]seryl-L-seryl-L-tyrosyl-L-tyrosyl-L-serylglycyl]amino]-α-L-*lyxo*-hexopyranosyl]oxy]-, (8S,10S)-

Excluded Compound 14

CAS Registry Number: 872611-87-5

$C_{42} H_{55} N_7 O_{18}$

Name - Glycine, N-[3-[2-[2-[2-(2,5-dihydro-2,5-dioxo-1H-pyrrol-1-yl)ethoxy]ethoxy]ethoxy]-1-oxopropyl]-L-seryl-L-seryl-L-tyrosyl-L-tyrosyl-L-seryl- (9CI)

Excluded Compound 15

CAS Registry Number: 792954-90-6

$C_{90} H_{131} F_{13} N_{22} O_{26} S$

Name - L-Lysinamide, N-(26,26,27,27,28,28,29,29,30,30,31,31,31-tridecafluoro-21,21-dioxido-1,17,23-trioxo-4,7,10,13-tetraoxa-21-thia-16,22-diazahentriacont-1-yl)-L-seryl-L-α-glutamyl-$N^6$-(aminoiminomethyl)-L-lysyl-L-seryl-L-norleucyl-L-α-glutamyl-(4R)-4-hydroxy-L-prolyl-D-phenylalanyl-L-arginyl-L-tryptophyl-, (6→11)-lactam (9CI Excluded Compound 16

CAS Registry Number: 341990-80-5

Name - L-Phenylalaninamide, $N$-(18,20-dicarboxy-16-hydroxy-16-oxido-13-oxo-3,6,9-trioxa-12-aza-16-phosphaeicos-1-yl)-$N^2$-(1,14-dioxo-3,6,9,12-tetraoxa-15-azapentacos-1-yl)-L-asparaginyl-3-{2-[2-(2-aminoethoxy)ethoxy]ethoxy]propanoyl-L-seryl-L-seryl-$N$-[tetrahydro-4-(4-hydroxyphenyl)-6-(iodomethylene)-2-oxo-2$H$-pyran-3-yl]-

Excluded Compound 17

CAS Registry Number: 341552-34-9

$C_{37} H_{51} N_5 O_{12}$

Name - L-Phenylalaninamide, $N$-[3-{2-[2-(2-aminoethoxy)ethoxy]ethoxy}-1-oxopropyl]-L-seryl-L-seryl-$N$-[6-ethylidenetetrahydro-4-(4-hydroxyphenyl)-2-oxo-2$H$-pyran-3-yl]- (9CI)

Excluded Compound 18

CAS Registry Number: 341552-26-9

$C_{43} H_{54} N_5 O_{13} P$

Name - L-Phenylalaninamide, $N$-[3-{2-[2-(2-aminoethoxy)ethoxy]ethoxy}-1-oxopropyl]-L-seryl-L-seryl-$N$-[(diphenoxyphosphinyl)(4-hydroxyphenyl)methyl]- (9CI)

Excluded Compound 19

CAS Registry Number: 341552-14-5

$C_{84} H_{128} N_9 O_{34} P_3$

Name - L-Phenylalaninamide, $N$-(18,20-dicarboxy-16-hydroxy-16-oxido-13-oxo-3,6,9-trioxa-12-aza-16-phosphaeicos-1-yl)-$N^2$-(1,14-dioxo-3,6,9,12-tetraoxa-15-azapentacos-1-yl)-L-asparaginyl-3-{2-[2-(2-aminoethoxy)ethoxy]ethoxy]propanoyl-L-seryl-L-seryl-$N$-[(diphenoxyphosphinyl)[4-(phosphonooxy)phenyl]methyl]- (9CI)

Excluded Compound 20

CAS Registry Number: 150439-04-6

$C_{60} H_{109} N_{11} O_{24}$

Name - D-Alaninamide, $N$-(3-cyclohexyl-1-oxopropyl)-L-alanyl-$O$-[2-(2-methoxyethoxy)ethyl]-L-seryl-L-alanyl-$O$-[2-(2-methoxyethoxy)ethyl]-L-seryl-L-threonyl-L-alanyl-$O$-[2-(2-methoxyethoxy)ethyl]-L-seryl-L-alanyl-$O$-[2-(2-methoxyethoxy)ethyl]-L-seryl- (9CI)

Excluded Compound 21

CAS Registry Number: 150439-01-3

Name - D-Alaninamide, O-[2-[2-(2-methoxyethoxy)ethoxy]ethyl]-L-seryl-L-phenylalanyl-L-alanyl-O-[2-[2-(2-methoxyethoxy)ethoxy]ethyl]-L-seryl-L-alanyl-O-[2-[2-(2-methoxyethoxy)ethoxy]ethyl]-L-seryl-L-threonyl-L-leucyl-L-lysyl-L-alanyl-L-alanyl- (9CI)

Excluded Compound 22

CAS Registry Number: 150438-98-5

$C_{83} H_{146} N_{14} O_{34}$

Name - D-Alaninamide, N-(1-oxo-4,7,10,13,16,19,22-heptaoxatricos-1-yl)-L-alanyl-L-alanyl-L-phenylalanyl-L-alanyl-L-alanyl-L-alanyl-O-[2-[2-(2-methoxyethoxy)ethoxy]ethyl]-L-seryl-L-threonyl-L-alanyl-O-[2-[2-(2-methoxyethoxy)ethoxy]ethyl]-L-seryl-L-alanyl-O-[2-[2-(2-methoxyethoxy)ethoxy]ethyl]-L-seryl- (9CI)

Excluded Compound 23

CAS Registry Number: 150438-96-3

$C_{78} H_{137} N_{15} O_{28}$

Name - D-Alaninamide, N-[(1,1-dimethylethoxy)carbonyl]-L-alanyl-O-[2-[2-(2-methoxyethoxy)ethoxy]ethyl]-L-seryl-L-phenylalanyl-L-alanyl-O-[2-[2-(2-methoxyethoxy)ethoxy]ethyl]-L-seryl-L-alanyl-O-[2-[2-(2-methoxyethoxy)ethoxy]ethyl]-L-seryl-L-threonyl-L-leucyl-L-lysyl-L-alanyl-L-alanyl- (9CI)

Excluded Compound 24

CAS Registry Number: 150438-95-2

$C_{64} H_{121} N_{15} O_{23} Si$

Name - D-Alaninamide, L-alanyl-O-[2-(2-methoxyethoxy)ethyl]-L-seryl-3-(trimethylsilyl)-L-alanyl-L-alanyl-O-[2-(2-methoxyethoxy)ethyl]-L-seryl-L-alanyl-O-[2-(2-methoxyethoxy)ethyl]-L-seryl-L-threonyl-L-leucyl-L-lysyl-L-alanyl-L-alanyl- (9CI)

Excluded Compound 25

CAS Registry Number: 150438-94-1

$C_{69} H_{129} N_{15} O_{25} Si$

Name - D-Alaninamide, N-[(1,1-dimethylethoxy)carbonyl]-L-alanyl-O-[2-(2-methoxyethoxy)ethyl]-L-seryl-3-(trimethylsilyl)-L-alanyl-L-alanyl-O-[2-(2-methoxyethoxy)ethyl]-L-seryl-L-alanyl-O-[2-(2-methoxyethoxy)ethyl]-L-seryl-L-threonyl-L-leucyl-L-lysyl-L-alanyl-L-alanyl- (9CI)

CAS Registry Number: 1232494-37-9

$C_{159} H_{220} N_{32} O_{41} S_2$

Name - L-Phenylalaninamide, N-[5-carboxy-2-(3,6-dihydroxyxanthylium-9-yl)benzoyl]-L-threonyl-L-phenylalanyl-L-valyl-L-α-aspartyl-L-α-glutamyl-L-arginyl-L-leucyl-L-leucyl-L-tyrosyl-L-phenylalanyl-L-leucyl-L-threonyl-L-isoleucylglycyl-L-asparaginyl-L-methionylglycyl-L-methionyl-L-tyrosyl-L-alanyl-L-alanyl-L-glutaminyl-L-leucyl-L-lysyl-, inner salt

2.

CAS Registry Number: 1185774-01-9

$C_{146} H_{219} N_{38} O_{37}$

Name - L-Lysine, N-[2-[3,6-bis(dimethylamino)xanthylium-9-yl]-3(or 4)-[[(2,5-dioxo-1-pyrrolidinyl)oxy]carbonyl]benzoyl]-L-seryl-L-tryptophyl-L-leucyl-L-lysylglycyl-L-α-glutamyl-L-phenylalanyl-L-isoleucyl-L-threonyl-L-threonyl-L-valyl-L-glutaminyl-L-glutaminyl-L-arginylglycyl-L-alanyl-L-alanyl-L-valyl-L-isoleucyl-L-lysyl-L-alanyl-L-arginyl-

3.

CAS Registry Number: 955960-78-8

$C_{68} H_{92} N_{16} O_{18}$

Name - L-Valine, N-[2-(6-hydroxy-3-oxo-3H-xanthen-9-yl)benzoyl]-L-threonyl-L-tyrosyl-L-glutaminyl-L-arginyl-L-threonyl-L-arginyl-L-alanyl-L-leucyl-

CAS Registry Number: 219127-42-1

C73 H128 N18 O26 S

Name - L-Valine, N-acetyl-b-neuraminoyl-L-seryl-Lasparaginyl-L-lysylglycyl-L-alanyl-L-isoleucyl-Lisoleucylglycyl-L-leucyl-L-methionyl-Lvalylglycylglycyl-L-valyl-

2.

CAS Registry Number: 183746-03-4

C73 H128 N18 O26 S

Name - L-Valine, N-(N-acetylneuraminoyl)-L-seryl-Lasparaginyl-L-lysylglycyl-L-alanyl-L-isoleucyl-Lisoleucylglycyl-L-leucyl-L-methionyl-Lvalylglycylglycyl-L-valyl-

CAS Registry Number: 591773-31-8

C21 H21 I4 N3 O8

L-Serine, O-(4-hydroxy-3,5-diiodophenyl)-3,5-diiodo-L-tyrosyl-L-seryl-

2.

CAS Registry Number: 591773-30-7

C21 H22 I3 N3 O8

L-Serine, O-(4-hydroxy-3-iodophenyl)-3,5-diiodo-L-tyrosyl-L-seryl-

Figure 9

1. CAS Registry Number: 1096702-17-8

MF - C107 H147 N21 O45 S2

Vincaleukoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-δ-glutamyl-2-amino-2-deoxy-D-mannonoyl-L- δ -glutamyl-2-amino-2-deoxy-D-mannonoyl-L- δ -glutamyl-2-amino-2-deoxy-D-mannonoyl-L- δ -glutamyl-2-amino-2-deoxy-D-mannonoyl-L-cysteine 2. CAS Registry Number: 1096702-13-4

MF- C 96 H131 N19 O39 S2

Name: Vincaleukoblastin-23-oic acid, O4-deacetyl-,2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-α.-aspartyl-2-amino-2-deoxy-D-mannonoyl-2-amino-2-deoxy-D-mannonoyl-2-amino-2-deoxy-D-mannonoyl-L-cysteine 3. CAS Registry Number: 1096702-12-3

MF - C108 H152 N24 O43 S2

Name - VincaleuKoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-α.-glutamyl-2-amino-2-deoxy-D-mannonoyl-L-arginyl-2-amino-2-deoxy-D-mannonoyl-L-α.-glutamyl-2-amino-2-deoxy-D-mannonoyl-L-cysteine 4. CAS Registry Number: 1096702-10-1

MF - C104 H141 N21 O45 S2

Name - Vincaleukoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-p-aspartyl-2-amino-2-deoxy-D-mannonoyl-L-p-aspartyl-2-amino-2-deoxy-D-mannonoyl-L-p-aspartyl-2-amino-2-deoxy-D-mannonoyl-L-cysteine 5. CAS Registry Number: 1096702-09-8

MF - C100 H13e N20 O42 S2

Name - Vincaleukoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-

Figure 9 (cont)

2-amino-2-deoxy-D-mannonoyl-L-α.-aspartyl-2- amino-2-deoxy-D-mannonoyl-2-amino-2-deoxy-D-mannonoyl-L-α.-aspartyl-2-amino-2-deoxy-D-mannonoyl-L-cysteine 6. CAS Registry Number: 1096702-08-7

MF - C108 H151 N23 O43 S2

Name - Vincaleukoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-α.-aspartyl-2-amino-2-deoxy-D-mannonoyl-4-(2-aminoethyl)-1-piperazineacetyl-2-amino-2-deoxy-D-mannonoyl-L-α.-aspartyl-2-amino-2-deoxy-D-mannonoyl-L-cysteine 7. CAS Registry Number: 1096702-07-6

MF - C104 H141 N21 O45 S2

Name - Vincaleukoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-α.-aspartyl-2-amino-2-deoxy-D-mannonoyl-L-α.-aspartyl-2-amino-2-deoxy-D-mannonoyl-L-α.-aspartyl-2-amino-2-deoxy-D-mannonoyl-L-cysteine 8. CAS Registry Number: 1096702-06-5

MF - C94 H125 N19 O37 S2.

Name - Vincaleukoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-α.-aspartyl-2-amino-2-deoxy-D-mannonoyl-L-α.-aspartyl-2-amino-2-deoxy-D-mannonoyl-L-cysteine 9. CAS Registry Number: 1096702-05-4

MF - C90 H120 N18 O34 S2

Name - Vincaleukoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-α.-aspartyl-2-amino-2-deoxy-D-mannonoyl-2-amino-2-deoxy-D-mannonoyl-L-cysteine 10. CAS Registry Number: 1096702-04-3

Name - Vincaleukoblastin-23-oic acid, O4-deacetyl-, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-v.-aspartyl-2-amino-2-deoxy-D-mannonoyl-L-cysteine

11. CAS Registry Number: 1096702-03-2

MF - C74 H93 N15 O21 S2

Name - Vincaleukoblastin-23-oic acid, 2-[(2-mercaptoethoxy)carbonyl]hydrazide, disulfide with N-[4-[[(2-amino-3,4-dihydro-4-oxo-6-pteridinyl)methyl]amino]benzoyl]-L-γ-glutamyl-2-amino-2-deoxy-D-mannonoyl-L-cysteine

12. CAS Registry Number: 1096701-98-2

MF - C48 H67 N13 O28 S

Name - L-Cysteine, N-[4-[[(2-amino-3,4-dihydro-4-oxo-6-pteridinyl)methyl]amino]benzoyl]-L-γ-glutamyl-2-amino-2-deoxy-D-mannonoyl-L-α.-aspartyl-2- amino-2-deoxy-D-mannonoyl-L-α.-aspartyl-2-amino-2-deoxy-D-mannonoyl-

13. CAS Registry Number: 1096701-97-1

MF - C44 H62 N 12 O25 S

Name - L-Cysteine, N-[4-[[(2-amino-3,4-dihydro-4-oxo-6-pteridinyl)methyl]amino]benzoyl]-L-γ-glutamyl-2-amino-2-deoxy-D-mannonoyl-L-α.-aspartyl-2-amino-2-deoxy-D-mannonoyl-2-amino-2-deoxy-D-mannonoyl-

14. CAS Registry Number: 1096701-96-0

MF - C38 H51 N11 O20 S

Name – L-Cysteine, N-[4-[[(2-amino-3,4-dihydro-4-oxo-6-ptendinyl)methyl]amino]benzoyl]-L-γ-glutamyl-2-amino-2-deoxy-D-mannonoyl-L-α.-aspartyl-2-amino-2-deoxy-D-mannonoyl

15. CAS Registry Number: 1096701-95-9

MF - C28 H35 N9 O12 S

Name - L-Cysteine, N-[4-[[(2-amino-3,4-dihydro-4-oxo-6-pteridinyl)methyl]amino]benzoyl]-L-γ-glutamyl-2-amino-2-deoxy-D-mannonoyl-

16. CAS Registry Number: 1096701-92-6

MF - C58 H83 N 15 O36 S

Name - L-Cysteine, N-[4-[[(2-amino-3,4-dihydro-4-oxo-6-pteridinyl)methyl]amino]benzoyl]-L-γ-glutamyl-2- amino-2-deoxy-D-mannonoyl-L-β-aspartyl-2-amino-2-deoxy-D-mannonoyl-L-β-aspartyl-2-amino-2-deoxy-D-mannonoyl-L-β-aspartyl-2-amino-2-deoxy-D-mannonoyl-

Figure 9 (cont)

17. CAS Registry Number: 1096701-91-5

MF - C61 H89 N15 O36 S

Name - L-Cysteine, N-[4-[[(2-amino-3,4-dihydro-4-oxo-6-ptendinyl)methyl]amino]benzoyl]-L-γ-glutamyl-2-amino-2-deoxy-D-mannonoyl-L-α.-glutamyl-2-amino-2-deoxy-D-mannonoyl-L-α.-glutamyl-2-amino-2-deoxy-D-mannonoyl-L-α-glutamyl-2- amino-2-deoxy-D-mannonoyl-

18. CAS Registry Number: 1096701-90-4

MF - C54 H78 N14 O33 S

Name- L-Cysteine, N-[4-[[(2-amino-3,4-dihydro-4-oxo-6-ptendinyl)methyl]amino]benzoyl]- L-γ-glutamyl-2-amino-2-deoxy-D-mannonoyl-L-α.-aspartyl-2-amino-2-deoxy-D-mannonoyl-2-amino-2-deoxy-D-mannonoyl-L-α.-aspartyl-2-amino-2-deoxy-D-mannonoyl-

19. CAS Registry Number: 1096701-89-1

MF - C62 H93 N17 O34 S

Name - L-Cysteine, N-[4-[[(2-amino-3 4-dihydro-4-oxo-6-pteridinyl)methyl]amino]benzoyl]-L-γ-glutamyl-2-amino-2-deoxy-D-mannonoyl-L-α-aspartyl-2-amino-2-deoxy-D-mannonoyl-4-(2-aminoethyl)-1-piperazineacetyl-2-amino-2-deoxy-D-mannonoyl-L-α.-aspartyl-2-amino-2-deoxy-D-mannonoyl-

20. CAS Registry Number: 1096701-88-0

MF - C62 H94 N18 O34 S

Name - L-Cysteine, N-[4-[[(2-amino-3,4-dihydro-4-oxo-6-pteridinyl)methyl]amino]benzoyl]-L-γ-glutamyl-2-am1no-2-deoxy-D-mannonoyl-L-α-glutamyl-2-amino-2-deoxy-D-mannonoyl-L-arginyl-2-amino-2-deoxy-D-mannonoyl-L-α-glutamyl-2-amino-2-deoxy-D-mannonoyl-

21. CAS Registry Number: 1096701-87-9

MF - C50 H73 N13 O30 S

Name - L-Cysteine, N-[4-[[(2-amino-3,4-dihydro-4-oxo-6-pteridinyl)methyl]amino]benzoyl]-L-γ-glutamyl-2-amino-2-deoxy-D-mannonoyl-L-α-aspartyl-2-amino-2-deoxy-D-mannonoyl-2-amino-2-deoxy-D-mannonoyl-2-amino-2-deoxy-D-mannonoyl-

22. CAS Registry Number: 1096701-86-8

MF - C58 H83 N15 O36 S

Name - L-Cysteine, N-[4-[[(2-amino-3,4-dihydro-4-oxo-6- pteridinyl)methyl]amino]benzoyl]-L-γ-glutamyl-2- amino-2-deoxy-D-mannonoyl-L.-α-aspartyl-2-amino-2-deoxy-D-mannonoyl-L-α-aspartyl-2-amino-2-deoxy-D-mannonoyl-L-α-aspartyl-2- amino-2-deoxy-D-mannonoyl-

Figure 9 (cont)

23. CAS Registry Number: 1096413-47-6

MF - C103 H150 N22 O47 S3

Name - D-Alanine, N-[4-[[(2-amino-3 4-dihydro-4-oxo-6- pteridinyl)methyl]amino]benzoyl]-L-γ-glutamyl-2- amino-2-deoxy-D-mannonoyl-L-α-aspartyl-2- amino-2-deoxy-D-mannonoyl-L-α-aspartyl-2- amino-2-deoxy-D-mannonoyl-L-α-aspartyl-2- amino-2-deoxy-D-mannonoyl-3-[[2-[[[2-[(2S,4R')- 4-[[[2-[( 1 R, 3R)-1-(acetyloxy)-4-methyl-3-[[(2S, 3S)-3-methyl-2-[[[(2R)-1-methyl-2-piperidinyl]carbonyl]am ino]-1-oxopentyl]][( 1 oxobutoxy)methyl]aminopentyl]-4-thiazolyl]carbonyl]amino]-5-(4-hydroxyphenyl)-2- methyl-1-oxopentyl]hydrazinyl]carbonyl]oxy ]ethyl]dithio]-

24. CAS Registry Number: 1096168-85-2

MF - C83 H105 N17 O43 S2

Name - D-Alanine, N-[4-LL(2-amino-3,4-dihydro-4-oxo-6-pteridinyl)methyl]amino]benzoyl]-L-γ-glutamyl-2- amino-2-deoxy-D-mannonoyl-L-α-aspartyl-2- amino-2-deoxy-D-mannonoyl-L-α-aspartyl-2- amino-2-deoxy-D-mannonoyl-L-α-aspartyl-2-amino-2-deoxy-D-mannonoyl-3-[[2-[[[[(4S)-4, 11- diethyl-3,4, 12, 14-tetrahydro-4-hydroxy-3, 14-dioxo-1 H-pyrano[3',4':6, 7]indolizino[1,2-b)quinolin-9 yl]oxy]carbonyl]oxy]ethyl]dithio]-

25. CAS Registry Number: 1096168-84-1

MF - C87 H115 Cl2 N15 O38 S2

Name - D-Cysteine, N-[4-[[(2-amino-3,4-dihydro-4-oxo- 6-pteridinyl)methyl]amino]benzoyl]-L-γ-glutamyl- 2-amino-2-deoxy-D-mannonoyl-L-α-aspartyl-2- amino-2-deoxy-D-mannonoyl-L-α-aspartyl-2- amino-2-deoxy-D-mannonoyl- (7,3')-disulfide with cyclo[2,2-dimethyl-β-alanyl-(2S)-2-hydroxy- 4-methylpentanoyl-(2E, 5S,6S,7 R, -S)-8-chloro- 5-hydroxy-7-[[(2-merca ptoethoxy)carbonyl]oxy]-
6- methyl-8-phenyl-2-octenoyl-3-chloro-O-methyl-D-tyrosyl-

26. CAS Registry Number: 1096168-66-9

MF - C54 H78 N14 O33 S

Name - D-Cysteine, N-[4-[[(2-amino-3,4-dihydro-4-oxo- 6-pteridinyl)methyl]amino)benzoyl]-L-γ-glutamyl- 2-amino-2-deoxy-D-mannonoyl-L-α-aspartyl-2- amino-2-deoxy-D-mannonoyl-2-amino-2-deoxy-D-mannonoyl-L-α-aspartyl-2-amino-2-deoxy-D-mannonoyl-

27. CAS Registry Number: 1096168-65-8

Name – D-Cysteine, N-[4-[[(2-amino-3,4-dihydro-4-oxo- 6-pteridinyl)methyl]amino)benzoyl]-L-γ-glutamyl -2-amino-2-deoxy-D-mannonoyl-2-amino-2- deoxy-D-mannonoyl-2-amino-2-deoxy-D-mannonoyl-L-α-aspartyl-2-amino-2-deoxy-D-mannonoyl-

28. CAS Registry Number: 1096168-64-7
MF - C46 H68 N12 O27 S
Name - L-Cysteine, N-[4-[[(2-amino-3,4-dihydro-4-oxo-6- pteridinyl)methyl]amino]benzoyl]-L-γ-glutamyl-2-amino-2-deoxy-D-mannonoyl-2-amino-2-deoxy-D- mannonoyl-2-amino-2-deoxy-D-mannonoyl-2- amino-2-deoxy-D-mannonoyl-

29. CAS Registry Number: 539792-09-1
MF - C61 H93 N27 O23
Name: L-Argininamide, N-[4-[[(2-amino-3,4-dihydro-4-oxo-6-pteridinyl)methyl]amino]benzoyl]-L-γ-glutamyl-L-seryl-L-threonyl-L-α-aspartyl-L-arginyl-L-α-aspartyl-L-arginyl-L-α-aspartyl-N-[3-[[2-(aminooxy)acetyl]amino]propyl]-

Figure 10

1. CAS Registry Number: 1432140-85-6
MF - C31 H55 N13 O10 S
Name – not available 2. CAS Registry Number: 1432140-82-3
MF - C31 H56 N14 O9 S
Name - not available 3. CAS Registry Number: 1421957-60-9
MF - C126 H214 N42 O31 S
Name –L-Alaninamide,N-[5 -[(3aS,4S,6aR)-hexahydro- 2-oxo-1 H-thieno[3,4-d]imidazol-4-yl]-1-oxopentyl]-L-seryl-L-valyl-L-isoleucyl-L-leucyl-L-isoleucyl-L-arginylglycylglycyl-L-arginyl-L-valyl-L-lysyl-L-v.-aspartyl-L-leucyl-L-prolylglycyl-L-valyl-L-arginyl-L-tyrosyl-L-histidyl-L-threonyl-L-valyl-L-arginylglycyl- 4. CAS Registry Number: 1416326-10-7
MF - C62 H99 N17 O24 S3
Name - L-Cysteine, N-[5-[(3aS,4S,6aR)-hexahydro-2-oxo-1 H-thieno[3,4-d]imidazol-4-yl]-1-oxopentyl]-L-serylglycyl-L-serylglycyl-L-cysteinyl-L-leucyl-L-α.-glutamyl-L-alanyl-L-prolyl-L-asparaginyl-L-isoleucyl-L-v.-glutamylglycyl- 5. CAS Registry Number: 1416326-09-4
MF - C71 H100 N18 O24 S3
Name - L-Cysteine, N-[5-[(3aS,4S,6aR)-hexahydro-2-oxo-1 H-thieno[3,4-d]imidazol-4-yl]-1-oxopentyl]-L-serylglycyl-L-serylglycyl-L-cysteinyl-L-seryl-L- leucyl-L-tryptophyl-L-α. aspartyl-L-threonyl-L-threonylglycyl-L-tryptophyl- 6. CAS Registry Number: 1416326-08-3
MF - C69 H96 N18 O25 S3
Name - L-Cysteine, N-[5-[(3aS,4S,6aR)-hexahydro-2-oxo-1 H-thieno[3,4-d]imidazol-4-yl]-1-oxopentyl]-L-serylglycyl-L-serylglycyl-L-cysteinyl-L-seryl-L- threonyl-L-tryptoph yl-L-α.-asp artyl-L -threonyl-L-threonyl glycyl-L-tryptophyl- 7. CAS Registry Number: 1374518-37-2
MF - C149 H215 N43 O29 S

Figure 10 (cont)

Name – not available

8. CAS Registry Number: 1374518-36-1

MF - C146 H213 N41 O30 S

Name – not available

9. CAS Registry Number: 1374201-83-8

MF - C17 H28 N4 O6 S2

Name – L-Cysteine, N-[5-[(3aS,4S,6aR)-hexahydro-2- oxo-1 H-thieno[3,4-d]imidazol-4-yl]-1-oxopentyl]-L-threonyl-

10. CAS Registry Number: 1374201-82-7

MF - C16 H26 N4 O6 S2

Name - L-Cysteine, N-[5-[(3aS,4S,6aR)-hexahydro-2- oxo-1 H-thieno[3,4-d]imidaz ol-4-yl]-1-oxopentyl]-L-seryl-

11. CAS Registry Number: 1374201-78-1

MF - C20 H35 N7 O6 S

Name - L-Arginine, N-[5-[(3aS,4S,6aR)-hexahydro-2- oxo-1 H-th ieno[3,4-d]imidazol-4-yl]-1-oxopentyl]-L-threonyl-

12. CAS Registry Number: 1332654-67-7

MF - C98 H173 Cl N38 O25 S

Name - L-Valine, N-[5-[(3aS,4S,6aR)-hexahydro-2-oxo- 1 H-thieno[3,4-d]imidazol-4-yl]-1-oxopentyl]-L-serylglycyl-N5-(2-ch loro-1-iminoethyl)-L-ornithylglycyl-L-lysylglycylglycyl-L-lysylglycyl-L-leucylg lycyl-L-lysylglycylglycyl-L-alanyl-L-lysyl-L-arginyl-L-histidyl-L-arginyl-L-lysyl-

13. CAS Registry Number: 1262241-24-6

MF - C65 H95 N13 O16 S

Name - L-Phenylalaninamide, N-[5-[(3aS,4S,6aR)-hexahy dro-2-oxo-1 H-thieno[3,4-d]imidazol-4-yl]- 1-oxopentyl]-L-seryl-L-glutaminyl-L-asparaginyl-L-tyrosyl-L-prolyl-L-isoleucyl-L-valyl-N-[( 1 S)-3- methyl-1-[[(2R)-2-methyl-2-oxiranyl]carbonyl]butyl]-

14. CAS Registry Number: 1262241-23-5

Name – L-Leucinamide, N-[5-[(3aS,4S,6aR)-hexahydro-2-oxo-1 H-thieno[3,4-d]imidazol-4-yl]-1-oxopentyl]-L-seryl-L-glutaminyl-L-asparaginyl-L-tyrosyl-L-prolyl-L-isoleucyl-L-valyl-L-phenylalanyl-N-(4-methyl-2-oxo-2H-1-benzopyran-7-yl)-

15. CAS Registry Number: 1262241-22-4

MF - C56 H80 N12 O15 S

Name - L-phenylalanine,N-[5-[(3aS,4S,6aR)-hexahydro-2-oxo-1 H-thieno[3,4-d]imidazol-4-yl]-1-oxopentyl]-L-seryl-L-glutaminyl-L-asparaginyl-L-tyrosyl-L-prolyl-L-isoleucyl-L-valyl-

16. CAS Registry Number: 1236396-03-4

MF - C47 H57 N7 O11 S2

Name – not available

17. CAS Registry Number: 229413-07-3

MF - C47 H58 N8 O10 S2

Name – not available

18. CAS Registry Number: 1204808-92-3

MF - C143 H183 Eu N37 O53 S2

Name – not available

19. CAS Registry Number: 1204739-32-1

MF - C143 H183 Eu N37 O53 S2

Europate( 1-), [N-[ 5-[(3aS,4S,6aR")-hexahydro-2-oxo-1 H-thieno[3,4-d]imidazol-4-yl]-1-oxopentyl]-L-serylglycylglycyl-L-serylglycylglycyl-L-serylglycylglycyl-L-serylglycylglycyl-L-serylglycylglycyl-L-serylglycylglycyl-L-serylglycylglycyl-D-phenylalanyl-(2S)-2-azetidinecarbonyl-N-[4-[[[[4-[2-[bis[[6-[[bis[(carboxy-κO)methyl]amino-κN]methyl]-4-[2-[4-(α-D-galactopyranosyloxy)phenyl]ethynyl]-2-pyridinyl-κN]methyl]amino-κN]ethyl]phenyl]amino]thioxomethyl]amino]phenyl]-L-argininamidato(4-)]-, hydrogen (1.1)

20. CAS Registry Number: 1204656-94-9

MF - C84 H125 N31 O33 S

Name : L-Argininamide, N-[5-[(3aS,4S,6a R)-hexahydro-2-oxo-1 H-thieno[3,4-d]imidazol-4-yl]-1-oxopentyl]-L-serylglycylglycyl-L-serylglycylglycyl-L-serylglycylglycyl-L-serylglycyl-L-serylglycylglycyl-L-serylglycylglycyl-L-serylglycylglycyl-D-phenylalanyl-(2S)-2-azetidinecarbonyl-N-(4-aminophenyl)-

Figure 10 (cont)

21. CAS Registry Number: 1204656-93-8

MF - C78 H119 N29 O34 S

Name - L-Arginine, N-[5-[(3aS,4S,6aR)-hexahydro-2- oxo-1 H-thieno[3,4-d]imidazol-4-yl]-1-oxopentyl]-L-serylglycylglycyl-L-serylglycylglycyl-L-serylglycylglycyl-L-serylglycylglycyl-L-serylglycylglycyl- L-serylglycylglycyl-L-serylglycylglycyl-D-phenylalanyl-(2S)-2-azetidinecarbonyl-

22. CAS Registry Number: 1196960-22-1

MF - C78 H128 N26 O24 S

Name - L-Arginine, N-[5-[(3aS,4S,6aR")-hexahydro-2-oxo-1 H-thieno[3,4-d]imidazol-4-yl]-1-oxopentyl]-L- seryl-L-α-glutamyl-L-valyl-L-asparaginyl-L- leu cyl-L-α-aspartyl-L-alanyl-L-α-glutamyl-L-phenylalanyl-L-arginyl-L-lysyl-L-arginyl-

23. CAS Registry Number: 1188 360-23-7

MF - C103 H156 N26. O34 S

Name – L-Aspartamide, N-[5-[(3aS,4S,6aR)-hexahydro-2-oxo-1 H-thieno[3,4-d]imidazol-4-yl]-1 oxopentyl]-L-serylglycyl-L-serylglycyl-L-seryl-L-glutaminyl-L-α-glutamyl-L-threonyl-L-phenylalanyl-L-seryl-L-α-aspartyl-L-leucyl-6-methyl-L-tryptophyl-L-lysyl-L-leucyl-L-leucyl-L-prolyl-L-α-glutamyl-

24. CAS Registry Number: 1188360-22-6

MF - C102 H153Cl N26 O34 S

Name: L-Aspartamide, N-[5-[(3aS,4S,6aR)-hexahydro-2-oxo-1 H-thieno[3,4-d]im idazol-4-yl]-1-oxopentyl]-L-serylglycyl-L-serylglycyl-L-seryl-L-glutaminyl-L-α-glutamyl-L-threonyl-L-phenylalanyl-L-seryl-L-α-aspartyl-L-leucyl-6-chloro-L-tryptophyl-L-lysyl-L-leucyl-L-leucyl-L-prolyl-L-α-glutamyl-

25. CAS Registry Number: 11883 60-21-5

MF - C102 H154 N26 O34 S

Name - L-Aspartamide, N-[5-[(3aS,4S,6aR)-hexahydro-2-oxo-1 H-thieno[3,4-d]imidazol-4-yl]-1-oxopentyl]-L-serylglycyl-L-serylglycyl-L-seryl-L-glutaminyl-L-α-glutamyl-L-threonyl-L-phenylalanyl-L-seryl-L-α-aspartyl-L-leucyl-L-tryptophyl-L-lysyl-L-leucyl-L-leucyl-L-prolyl-L-α-glutamyl-

26. CAS Registry Number: 1180668-49-8

Name - L-Lysine, N-[5-[(3aS,4S,6aR)-hexahydro-2-oxo-
1H-thieno[3,4-d]imidazol-4-yl]-1-oxopentyl]-L-serylglycyl-L-serylglycyl-L-arginyl-L-alanyl-
L-seryl-L-valyl-L-phenylalanyl-l-tyrosyl-O-phosphono-L-tyrosyl-L-α-glutamyl-L-isoleucyl-L-leucyl-
L-asparaginyl-L-seryl-

27. CAS Registry Number: 1147270-43-6
MF - C94 H150 N32 O33S
Name: L-Argirnne, N-(5-t(3aS,4S,6aR)-hexahydro-2-oxo-1H-thieno[3,4-d]imidazol-4-yl]-1-
oxopentyl]-L-serylglycyl-L-serylglycyl-L-isoleucyl-L-seryl-L-glutaminyl-L-alanyl-L-valyl-L-
histidyl-L-alanyl-L-alanyl-L-histidyl-L-alanyl-L-α-glutamyl-L-isoleucyl-L-asparaginyl-L-α-
glutamyl-L-alanylglycyl-

28. CAS Registry Number: 1147270-42-5
MF - C88 H127 N25 O27 S
Name - L-Glutamamlde, N-[5-[(3aS,4S,6aR)-hexahydro-2-oxo-1H-thieno[3,4-d]imidazol-4-yl]-1-
oxopentyl]-L-serylg lycyl-L-seryl lycyl-L-glutaminyl-L-glutaminyl-L-lysyl-L-phenylalanyl-
L-glutaminyl-L-phenylalanyl-L-glutaminyl-L-phenylalanyl-L-α-glutamyl-L-glutaminyl-

29. CAS Registry Number: 1147270-41-4
MF - C119 H182 N34 O35 S
Name- L-Glutamamide, N-[5-[(3aS,4S,6aR)-hexahydro-2-oxo-1H-thieno[3,4-d]imidazol-4-yl]-1
oxopentyl]-L-serylglycyl-L-serylglycyl-L-isoleucyl-L-lysyl-L-valyl-L-alanyl-
L-valylglycylglycylglycyl-L-glutaminyl-L-glutaminyl-L-lysyl-L-phenylalanyl-L-glutaminyl-
L-phenylalanyl-L-glutaminyl-L-phenylalanyl-L-α-glutamyl-L-glutaminyl-

30. CAS Registry Number: 1147270-40-3
MF - C109 H161 N35 O37 S
Name - L-Glutamamide, N-(S 5-[(3aS,4S,6aR)-hexahydro-2-oxo-1H-thieno[3,4-d]im idazol-4-yl]-1-
oxopentyl]-L-serylglycyl-L-serylglycyl-L-arginylglycyl-L-α-aspartyl-L-serylglycylglycylglycyl-L-
glutaminyl-L-glutaminyl-L-lysyl-L-phenylalanyl-L-glutaminyl-L-phenylalanyl-L-glutaminyl-L-
phenylalanyl-L-α-glutamyl-L-glutaminyl-

31. CAS Registry Number: 1052687-54-3
MF - C75 H99 N 15 O39 S
Name - L:Serine, N-(2,3-dihydroxybenzoyl)-O-[N-(2,3-dihydroxybenzoyl)-O-(N-(5-[6-0-(N-(5-
[(3aS,4S,6aR)-hexahydro-2-oxo-1H-thieno[3,4-d]imidazol-4-yl]-1-oxopentyl]-L-seryl-L-alanyl-

Figure 10 (cont)

L-threonyl-L-seryl-L-seryl-L-serylglycyl-L-serylglycyl-L-seryl]-β-D-glucopyranosyl]-2,3-dihydroxybenzoyl]-L-seryl]-L-seryl]-P-D-glucopyL-seryl]-, ( 3--, $1^3$ )-lactone

32. CAS Registry Number: 1052687-53-2

MF - C75 H99 N15 O39 S

Name - L Serine, N-(2,3-dihydroxybenzoyl)-O-[N-(2,3 dihydroxybenzoyl)-O-[N-[5-[4-O-[N-[5-[(3aS,4S,6aR)-hexahydro-2-oxo-1 H-thieno[3,4-d]imidazol-4-yl]-1-oxopentyl]-L-seryl-L-alanyl-L-threonyl-L-seryl-L-seryl-L-serylglycyl-L-serylglycyl-L-seryl]-β-D-glucopyranosyl]-2,3-dihydroxybenzoyl]-L-seryl]-L-seryl]-, ( 3--, $1^3$ )-lactone

33. CAS Registry Number: 1052687-26-9

MF - C39 H64 N12 O20 S

Name --L-Serine, N- [5-[3aS,4S,6aR)-hexahydro-2-oxo1 H-thieno[3,4-d]imidazol-4-yl]-1-oxopentyl]-L-seryl-L-alanyl-L-threonyl-L-seryl-L-seryl-L-serylglycyl-L-serylglycyl-

34. CAS Registry Number: 1046465-81-9

MF - C47 H74 N10 O12 S

Name -- not available

35. CAS Registry Number: 1044498-22-7

MF - C96 H160 N26 O27 S4

Name - L-Tyrosine, N-[5-[(3aS,4S,6a R)-hexahydro-2-oxo-1 H-thieno[3,4-d]imidazol-4-yl]-1-oxopentyl]-L-serylglycylglycylglycyl-L-seryl-L-lysyl-L-methionyl-L-arginyl-L-methionyl-L-alanyl-L-threonyl-L-prolyl-L-leucyl-L-leucyl-L-methionyl-L-glutaminyl-L-alanyl-L-leucyl-

36. CAS Registry Number: 1002105-33-0

MF - C86 H142 N32 O19 S

Name - L-Leucine, N-[5-[(3aS,4S,6aR)-hexahydro-2-oxo-1H-thieno[3,4-d]imidazol-4-yl]-1-oxopentyl]-L- seryl-L-isoleucyl-L-tyrosyl-L-arginyl-L-arginylglycyl-L-seryl-L-arginyl-L-arginyl-L-tryptophyl-L-arginyl-L-lysyl-

37. CAS Registry Number: 1000873-73-3

MF - C85 H129 N25 O19 S

Name - L-Lysine, N-[5-[(3aS,4S,6aR)-hexahydro-2-oxo-1H-thieno[3,4-d]imidazol-4-yl]-1-oxopentyl]-L-threonyl-L-tryptophyl-L-tyrosyl-L-lysyl-L-isoleucyl-L-alan yl-L-phenylalanyl-L-glutaminyl-L-arginyl-L-asparaginyl-L-arginyl-

Figure 10 (cont)

38. CAS Registry Number: 959902-31-9

MF - C76 H110 N24. O18S3

Name - L-Cysteine, N-[:i-[(3aS,4S,6aR)-hexahydro-2- oxo-1 H-th ieno[3,4-d]imidazol-4-yl]-1-oxopentyl] serylglycyl-L-serylglycyl-L-arginyl-L-lysyl-L-leucyl-L-tryptophyl-L-cysteinyl-L-histidyl-L-histidyl-L-phenylalanyl-

39. CAS Registry Number: 959852-48-3

MF - C65 H103 N27 O20 S3

Name - Glycine, N-[5-[(3aS,4S,6aR)-hexahydro-2-oxo-1 H-thieno[3,4-d]imidazol-4-yl]-1-oxopentyl]-L-seryl-L-alanyl-L-cysteinyl-L-α-aspartyl-L-arginyl-L-histidyl-L-glutaminyl-L-histidyl-L-lysyl-L-arginyl-L-cysteinylglycyl- , cyclic (3->11)-disulfide

40. CAS Registry Number: 948844-62-0

MF - C52 H85 N13 O15 S2

Name - L-Cysteine, N-[5-[(3a S,4S,6a R)-hexahydro-2- oxo-1H-thieno[3,4-d]imidazol-4-yl]-1-oxopentyl]- L-seryl-L-leucyl-L-leucyl-L-prolylglycyl-L-leucyl-L-prolylglycylglycylglycyl-

41. CAS Registry Number: 9421 56-60-7

MF - C98 H176 N32 O20 S

Name - L-Valine, N-[5-[(3aS,4S,6a R)-hexahydro-2-oxo-1H-thieno[3,4-d]imidazol-4-yl]-1-oxopentyl]-L-threonyl-L-lysyl-L-arginyl-L-lysyl-L-arginyl-L-lysyl-L-lysyl-L-g lutaminyl-L-arginyl-L-valyl-L-lysyl-L-isoleucyl-L-isoleucyl-L-phenylalanyl-

42. CAS Registry Number: 908857-92-1

MF - C69 H108 N24 O23 S3

Name - L-Lysine, N-[5-[(3aS,4S,6aR)-hexahydro-2-oxo-1H-thieno[3,4-d]imidazol-4-yl]-1-oxopentyl]-L-serylglycyl-L-serylglycyl-L-cysteinyl-L-asparaginyl-L-prolyl-L-arginylglycyl-L-α-aspartyl-O-methyl-L-tyrosyl-L-arginyl-L-cysteinyl- , cyclic (5->13)-disulfide

43. CAS Registry Number: 906461-19-6

MF - C77 H111 N19 O28 S

Name — L-Serine, N-[5-[(3aS,4S,6aR)-hexahydro-2-oxo- 1H-thieno[3,4-d]imidazol-4-yl]-1-oxopentyl]-L-serylglycyl-L-serylglycyl-L-α-glutamyl-L-prolyl-L-valyl-L-α-aspartyl-L-prolyl-L-asparaginyl-L-leucyl-L-α-aspartyl-L-prolyl-L-tryptophyl-

44. CAS Registry Number: 906461-18-5

Name - L-Serine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-L-prolyl-L-valyl-L-α.-aspartyl-L-prolyl-L-asparaginyl-L-leucyl-L-α-glutamyl-L-prolyl-L-tryptophyl-

45. CAS Registry Number: 906461-17-4

MF - C77 H112 N28 O28 S

Name - L-Serine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-L-prolyl-L-valyl-L-α-aspartyl-L-prolyl-L-seryl-L-leucyl-L-α-glutamyl-L-prolyl-L-tryptophyl-

46. CAS Registry Number: 906461-16-3

MF - C80 H119 N19 O27 S

Name - L-Serine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-L-prolyl-L-valyl-L-α-aspartyl-L-prolyl-L-lysyl-L-leucyl-L-α-glutamyl-L-prolyl-L-tryptophyl-

47. CAS Registry Number: 906461-15-2

MF - C80 H119 N21 O27 S

Name - L-Serine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-L-prolyl-L-valyl-L-α-aspartyl-L-prolyl-L-arginyl-L-leucyl-L-α-glutamyl-L-prolyl-L-tryptophyl-

48. CAS Registry Number: 906461-14-1

MF - C64 H92 N16 O22 S

Name - L-Tryptophan, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-α-aspartyl-L-prolyl-L-asparaginyl-L-leucyl-L-α-aspartyl-L-prolyl-

49. CAS Registry Number: 906461-13-0

MF - C63 H91 N15 O22 S

Name – L-Tryptophan, N-[5-[(3aS,4S,6aR)-hexahydro-2-oxo-1H-thieno[3,4-d]imidazol-4-yl]-1-oxopentyl]- L-Serylglycyl-L-serylglycyl-L-valyl-L-α-aspartyl-L- prolyl-L-seryl-L-leucyl-L-α-aspartyl-L-prolyl-

50. CAS Registry Number: 906461-12-9

Name - L-Tryptophan, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-α-aspartyl-L-prolyl-L-lysyl-L-leucyl-L-v-aspartyl-L-prolyl-

51.

CAS Registry Number: 906461-11-8

MF - C66 H98 N18 O21 S

Name - L-Tryptophan, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-α-aspartyl-L-prolyl-L-arginyl-L-leucyl-L-α-aspartyl-L-prolyl-

52.

CAS Registry Number: 906461-10-7

MF - C64 H93 N15 O22 S

Name - L-Tryptophan, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-α-aspartyl-L-prolyl-L-seryl-L-leucyl-L-α-glutamyl-L-prolyl-

53.

CAS Registry Number: 906461-09-4

MF - C65 H94 N16 O22 S

Name - L-Tryptophan, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-α-aspartyl-L-prolyl-L-asparaginyl-L-leucyl-L-α-glutamyl-L-prolyl-

54.

CAS Registry Number: 906461-08-3

MF - C67 H100 N16 O21 S

Name - L-Tryptophan, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-α-aspartyl-L-prolyl-L-lysyl-L-leucyl-L-α-glutamyl-L-prolyl-

55.

CAS Registry Number: 906461-07-2

Name - L-Tryptophan, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-α-aspartyl-L-prolyl-L-arginyl-L-leucyl-L-α-glutamyl-L-prolyl-

56.

CAS Registry Number: 906461-06-1

MF - C63 H103 N19 O21 S

Name - L-Serine, N-[5-[(3aS,4S,6aR)-hexahydro-2-oxo-1H-thieno[3,4-d]imidazol-4-yl]-1-oxopentyl]-Lserylglycyl-L-serylglycyl-L-leucylglycyl-L-isoleucyl-L-seryl-L-tyrosylglycyl-L-arginyl-L-lysyl-

57.

CAS Registry Number: 906461-05-0

MF - C20 H32 N6 O9 S

Name - Glycine, N-[5-[(3aS,4S,6aR)-hexahydro-2-oxo-1H-thieno[3,4-d]imidazol-4-yl]-1-oxopentyl]-Lserylglycyl-L-seryl-

58.

CAS Registry Number: 887367-25-1

MF - C102 H153 N25 O35 S

Name - L-Asparagine, N-[5-[(3aS,4S,6aR)-hexahydro-2-oxo-1H-thieno[3,4-d]imidazol-4-yl]-1-oxopentyl]-L-serylglycyl-L-serylglycyl-L-seryl-L-glutaminyl-L-α-glutamyl-L-threonyl-L-phenylalanyl-L-seryl-L-α-aspartyl-L-leucyl-L-tryptophyl-L-lysyl-L-leucyl-L-leucyl-L-prolyl-L-α-glutamyl-

59.

CAS Registry Number: 884876-59-9

MF - C83 H113 N17 O20 S

Name - L-Proline, N-[5-[(3aS,4S,6aR)-hexahydro-2-oxo-1H-thieno[3,4-d]imidazol-4-yl]-1-oxopentyl]-Lthreonyl-L-leucyl-L-prolyl-L-tyrosyl-L-tryptophyl-L-tryptophyl-L-leucyl-L-threonyl-L-prolyl-L-seryl-L-asparaginyl-

60.

CAS Registry Number: 862167-86-0

Name - L-Proline, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-threonyl-L-prolyl-L-prolyl-L-prolyl-L-leucyl-L-prolyl-

61.

CAS Registry Number: 862075-29-4

MF - C73 H129 N23 O23 S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-leucyl-L-isoleucyl-L-lysyl-L-arginyl-L-arginyl-L-seryl-L-threonyl-L-α-glutamyl-

62.

CAS Registry Number: 862075-28-3

MF - C73 H124 N25 O27 P S

Name - L-Isoleucine, N-[5-[(3aS,4S,6aR)-hexahydro-2-oxo-1H-thieno[3,4-d]imidazol-4-yl]-1-oxopentyl]-L-serylglycyl-L-serylglycyl-L-prolyl-L-arginyl-L-prolyl-L-leucyl-L-arginyl-L-arginyl-L-α-glutamyl-O-phosphono-L-seryl-L-α-glutamyl-

63.

CAS Registry Number: 862075-27-2

MF - C73 H123 N25 O24 S

Name - L-Isoleucine, N-[5-[(3aS,4S,6aR)-hexahydro-2-oxo-1H-thieno[3,4-d]imidazol-4-yl]-1-oxopentyl]-L-serylglycyl-L-serylglycyl-L-prolyl-L-arginyl-L-prolyl-L-leucyl-L-arginyl-L-arginyl-L-α-glutamyl-L-seryl-L-α-glutamyl-

64.

CAS Registry Number: 862075-26-1

MF - C73 H130 N23 O26 P S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-leucyl-L-isoleucyl-L-lysyl-L-arginyl-L-arginyl-L-seryl-O-phosphono-L-threonyl-L-α-glutamyl-

65.

CAS Registry Number: 862075-25-0

Name - Glycine, N-[5-[(3aS,4S,6aR)-hexahydro-2-oxo-1H-thieno[3,4-d]imidazol-4-yl]-1-oxopentyl]-Lserylglycyl-L-serylglycylglycyl-L-threonyl-L-prolyl-L-prolyl-L-prolyl-L-prolyl-L-tyrosyl-L-threonyl-L-valyl-

66.

CAS Registry Number: 862075-24-9

MF - C70 H107 N17 O21 S

Name - L-Proline, N-[5-[(3aS,4S,6aR)-hexahydro-2-oxo-1H-thieno[3,4-d]imidazol-4-yl]-1-oxopentyl]-L-serylglycyl-L-serylglycylglycyl-L-alanyl-L-prolyl-L-prolyl-L-threonyl-L-prolyl-L-prolyl-L-prolyl-L-leucyl-L-prolyl-

67.

CAS Registry Number: 862075-23-8

MF - C69 H112 N17 O29 P S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-Lglutaminyl-L-prolyl-L-leucyl-O-phosphono-L-threonyl-L-prolyl-L-valyl-L-threonyl-L-α-aspartyl-

68.

CAS Registry Number: 857286-00-1

MF - C68 H117 N19 O16 S2

Name - Glycinamide, N-[5-[(3aS,4S,6aR)-hexahydro-2-oxo-1H-thieno[3,4-d]imidazol-4-yl]-1-oxopentyl]-L-seryl-L-valyl-L-leucyl-L-histidyl-L-leucyl-L-valyl-L-leucyl-L-alanyl-L-leucyl-L-arginyl-N-[(2E)-3-(methylsulfonyl)-2-propenyl]-

69.

CAS Registry Number: 857285-95-1,

MF - C70 H122 N22 O17 S2

Name - Glycinamide, N-[5-[(3aS,4S,6aR)-hexahydro-2-oxo-1H-thieno[3,4-d]imidazol-4-yl]-1-oxopentyl]-L-seryl-L-threonyl-L-leucyl-L-histidyl-L-leucyl-Lvalyl-L-leucyl-L-arginyl-L-leucyl-L-arginyl-N-[(2E)-3-(methylsulfonyl)-2-propenyl]-

70.

CAS Registry Number: 811437-79-3

Name - L-Arginine, N-{5-[(3aS,4S,6aR)-hexahydro-2-oxo-1H-thieno[3,4-d]imidazol-4-yl]-1-oxopentyl]-L-serylglycyl-L-serylglycyl-L-seryl-L-seryl-L-alanyl-L-tyrosyl-L-seryl-

71.

CAS Registry Number: 811437-78-2

MF - C51 H84 N14 O21 S

Name - L-Lysine, N-{5-[(3aS,4S,6aR)-hexahydro-2-oxo-1H-thieno[3,4-d]imidazol-4-yl]-1-oxopentyl]-L-serylglycyl-L-serylglycyl-L-threonyl-L-α-glutamyl-L-α-glutamyl-L-glutaminyl-L-leucyl-

72.

CAS Registry Number: 811437-77-1

MF - C53 H83 N13 O18 S

Name - L-Lysine, N-{5-[(3aS,4S,6aR)-hexahydro-2-oxo-1H-thieno[3,4-d]imidazol-4-yl]-1-oxopentyl]-L-serylglycyl-L-serylglycyl-L-leucyl-L-threonyl-L-α-glutamyl-L-phenylalanyl-L-alanyl-

73.

CAS Registry Number: 811437-75-9

MF - C51 H75 N13 O21 S

Name - L-Lysine, N-{5-[(3aS,4S,6aR)-hexahydro-2-oxo-1H-thieno[3,4-d]imidazol-4-yl]-1-oxopentyl]-L-serylglycyl-L-serylglycyl-L-α-aspartyl-L-phenylalanyl-L-alanyl-L-α-glutamyl-L-α-aspartyl-

74.

CAS Registry Number: 811437-73-7

MF - C55 H87 N15 O18 S

Name - L-Arginine, N-{5-[(3aS,4S,6aR)-hexahydro-2-oxo-1H-thieno[3,4-d]imidazol-4-yl]-1-oxopentyl]-L-serylglycyl-L-serylglycyl-L-leucyl-L-tyrosyl-L-α-glutamyl-L-isoleucyl-L-alanyl-

75.

CAS Registry Number: 811437-67-9

MF - C45 H69 N11 O16 S

Name - L-Lysine, N-{5-[(3aS,4S,6aR)-hexahydro-2-oxo-1H-thieno[3,4-d]imidazol-4-yl]-1-oxopentyl]-L-serylglycyl-L-serylglycyl-L-tyrosyl-L-leucyl-L-α-aspartyl-

CAS Registry Number: 811437-65-7

MF - C44 H64 N14 O16 S
Name - L-Arginine, N-[5-[(3aS,4S,6aR)-hexahydro-2-oxo-1H-thieno[3,4-d]imidazol-4-yl]-1-oxopentyl]-L-serylglycyl-L-serylglycyl-L-tryptophyl-L-α-aspartyl-L-seryl-

77.

CAS Registry Number: 811437-63-5

MF - C37 H61 N11 O16 S
Name - L-Lysine, N-[5-[(3aS,4S,6aR)-hexahydro-2-oxo-1H-thieno[3,4-d]imidazol-4-yl]-1-oxopentyl]-L-serylglycyl-L-serylglycyl-L-threonylglycyl-L-α-glutamyl-

78.

CAS Registry Number: 811437-61-3

MF - C41 H65 N11 O17 S
Name - L-Lysine, N-[5-[(3aS,4S,6aR)-hexahydro-2-oxo-1H-thieno[3,4-d]imidazol-4-yl]-1-oxopentyl]-L-serylglycyl-L-serylglycyl-L-prolyl-L-α-glutamyl-L-α-glutamyl-

79.

CAS Registry Number: 811437-58-8

MF - C40 H68 N12 O15 S
Name - L-Lysine, N-[5-[(3aS,4S,6aR)-hexahydro-2-oxo-1H-thieno[3,4-d]imidazol-4-yl]-1-oxopentyl]-Lserylglycyl-L-serylglycyl-L-leucyl-L-glutaminyl-L-seryl-

80.

CAS Registry Number: 811437-55-5

MF - C40 H67 N13 O14 S
Name - L-Arginine, N-[5-[(3aS,4S,6aR)-hexahydro-2-oxo-1H-thieno[3,4-d]imidazol-4-yl]-1-oxopentyl]-L-serylglycyl-L-serylglycyl-L-leucyl-L-prolyl-L-seryl-

81.

CAS Registry Number: 811437-53-3

MF - C41 H63 N13 O15 S
Name - L-Lysine, N-[5-[(3aS,4S,6aR)-hexahydro-2-oxo-1H-thieno[3,4-d]imidazol-4-yl]-1-oxopentyl]-Lserylglycyl-L-serylglycyl-L-histidyl-L-prolyl-L-α-aspartyl-

CAS Registry Number: 811437-52-2

MF - C45 H67 N13 O15 S

Name - L-Arginine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-L-prolyl-L-phenylalanyl-

83.

CAS Registry Number: 811437-51-1

MF - C41 H65 N13 O17 S

Name - L-Arginine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-L-prolyl-L-α-glutamyl-

84.

CAS Registry Number: 811437-50-0

MF - C44 H65 N13 O17 S

Name - L-Arginine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-L-α-aspartyl-L-phenylalanyl-

85.

CAS Registry Number: 667430-86-6

MF - C127 H185 N33 O44 S

Name - L-Lysine, N-[5-[(3aS,4S,6aR)-hexahydro-2-oxo-1H-thieno[3,4-d]imidazol-4-yl]-1-oxopentyl]-Lserylglycyl-L-serylglycyl-L-lysyl-L-prolyl-L-seryl-L-tyrosyl-L-glutaminyl-Lphenylalanylglycylglycyl-L-histidyl-L-asparaginyl-L-seryl-L-valyl-L-α-aspartyl-Lphenylalanyl-L-α-glutamyl-L-α-glutamyl-L-α-aspartyl-L-threonyl-L-leucyl-L-prolyl-

86.

CAS Registry Number: 630093-44-6

MF - C124 H204 N34 O42 S

Name - L-Leucinamide, N-[5-[(3aS,4S,6aR)-hexahydro-2-oxo-1H-thieno[3,4-d]imidazol-4-yl]-1-oxopentyl]-L-seryl-L-isoleucyl-L-seryl-Lglutaminyl-L-valyl-L-asparaginyl-L-α-glutamyl-L-α-glutamyl-L-isoleucyl-L-asparaginyl-Lglutaminyl-L-seryl-L-leucyl-L-alanyl-L-tyrosyl-L-isoleucyl-L-arginyl-L-lysyl-L-seryl-L-α-aspartyl-L-α-glutamyl-L-leucyl-

CAS Registry Number: 630093-43-5

MF - C124 H204 N34 O40 S

Name - L-Leucinamide, N-[5-[(3aS,4S,6aR)-hexahydro-2-oxo-1H-thieno[3,4-d]imidazol-4-yl]-1-
oxopentyl]-L-seryl-L-isoleucyl-L-seryl-Lglutaminyl-L-valyl-L-asparaginyl-L-α-glutamyl-L-α-
glutamyl-L-isoleucyl-L-asparaginyl-L-glutaminyl-L-alanyl-L-leucyl-L-alanyl-L-tyrosyl-L-
isoleucyl-L-arginyl-L-lysyl-L-alanyl-L-α-aspartyl-L-α-glutamyl-L-leucyl-

88.

CAS Registry Number: 623579-62-4

MF - C82 H121 N21 O26 S

Name - L-Lysine, N-[5-[(3aS,4S,6aR)-hexahydro-2-oxo-1H-thieno[3,4-d]imidazol-4-yl]-1-
oxopentyl]-Lthreonyl-L-arginyl-L-α-aspartyl-L-isoleucyl-Ltyrosyl-L-α-glutamyl-L-threonyl-L-α-
aspartyl-L-tyrosyl-L-tyrosyl-L-arginyl-

89.

CAS Registry Number: 604784-58-9

MF - C40 H66 N10 O14 S

Name - L-Leucine, N-[5-[(3aS,4S,6aR)-hexahydro-2-oxo-1H-thieno[3,4-d]imidazol-4-yl]-1-
oxopentyl]-L-threonyl-L-valyl-L-glutaminyl-L-glutaminyl-L-α-glutamyl-

90.

CAS Registry Number: 573700-00-2

573699-99-7

MF - C71 H137 N21 O13 S 76-05-1

C2 H F3 O2

C71 H137 N21 O13 S . x C2 H F3 O2

Name - Glycinamide, N-[5-[(3aS,4S,6aR)-hexahydro-2-oxo-1H-thieno[3,4-d]imidazol-4-yl]-1-
oxopentyl]-L-seryl-N-[(1S,5S,9S,13S,17S,21S,25S,29S)-33-amino-1,5,9,13,17,21,25-
heptakis(4-aminobutyl)-29-(2-amino-2-oxoethyl)-3,7,11,15,19,23,27-heptaoxo-
4,8,12,16,20,24,28-heptaazatritriacont-1-yl]-,trifluoroacetate (salt)

91.

CAS Registry Number: 573699-99-7

Figure 10 (cont)

MF - C71 H137 N21 O13 S
Name - Glycinamide, N-[5-[(3aS,4S,6aR)-hexahydro-2-oxo-1H-thieno[3,4-d]imidazol-4-yl]-1-oxopentyl]-L-seryl-N-[(1S,5S,9S,13S,17S,21S,25S,29S)-33-amino-1,5,9,13,17,21,25-heptakis(4-aminobutyl)-29-(2-amino-2-oxoethyl)-3,7,11,15,19,23,27-heptaoxo-4,8,12,16,20,24,28-heptaazatritriacont-1-yl]-

92.

CAS Registry Number: 573699-98-6
573699-97-5
C64 H123 N19 O12 S
76-05-1
C2 H F3 O2
MF - C64 H123 N19 O12 S . x C2 H F3 O2
Name - Glycinamide, N-[5-[(3aS,4S,6aR)-hexahydro-2-oxo-1H-thieno[3,4-d]imidazol-4-yl]-1-oxopentyl]-L-seryl-N-[(1S,5S,9S,13S,17S,21S,25S)-29-amino-1,5,9,13,17,21-hexakis(4-aminobutyl)-25-(2-amino-2-oxoethyl)-3,7,11,15,19,23-hexaoxo-4,8,12,16,20,24-hexaazanonacos-1-yl]-,trifluoroacetate (salt)

93.

CAS Registry Number: 573699-97-5
MF - C64 H123 N19 O12 S
Name - Glycinamide, N-[5-[(3aS,4S,6aR)-hexahydro-2-oxo-1H-thieno[3,4-d]imidazol-4-yl]-1-oxopentyl]-L-seryl-N-[(1S,5S,9S,13S,17S,21S,25S)-29-amino-1,5,9,13,17,21-hexakis(4-aminobutyl)-25-(2-amino-2-oxoethyl)-3,7,11,15,19,23-hexaoxo-4,8,12,16,20,24-hexaazanonacos-1-yl]-

94.

CAS Registry Number: 573699-96-4
573699-95-3
MF - C57 H109 N17 O11 S
76-05-1
C2 H F3 O2
C57 H109 N17 O11 S . x C2 H F3 O2
Name - Glycinamide, N-[5-[(3aS,4S,6aR)-hexahydro-2-oxo-1H-thieno[3,4-d]imidazol-4-yl]-1-oxopentyl]-L-seryl-N-[(1S,5S,9S,13S,17S,21S)-25-amino-1,5,9,13,17-pentakis(4-aminobutyl)-21-(2-amino-2-oxoethyl)-3,7,11,15,19-pentaoxo-4,8,12,16,20-pentaazapentacos-1-yl]-,trifluoroacetate (salt)

CAS Registry Number: 573699-95-3

MF - C57 H109 N17 O11 S

Name - Glycinamide, N-[5-[(3aS,4S,6aR)-hexahydro-2-oxo-1H-thieno[3,4-d]imidazol-4-yl]-1-oxopentyl]-L-seryl-N-[(1S,5S,9S,13S,17S,21S)-25-amino-1,5,9,13,17-pentakis(4-aminobutyl)-21-(2-amino-2-oxoethyl)-3,7,11,15,19-pentaoxo-4,8,12,16,20-pentaazapentacos-1-yl]-

96.

CAS Registry Number: 503179-59-7

MF - C77 H116 N22 O32 S

Name - L-Arginine, N-[5-[(3aS,4S,6aR)-hexahydro-2-oxo-1H-thieno[3,4-d]imidazol-4-yl]-1-oxopentyl]-L-seryl-L-alanyl-L-asparaginyl-L-alanyl-L-α-glutamyl-L-α-aspartyl-L-alanyl-L-glutaminyl-L-α-glutamyl-L-phenylalanyl-L-seryl-L-α-aspartyl-L-valyl-L-α-glutamyl-

97.

CAS Registry Number: 490022-93-0

MF - C120 H190 N32 O37 S

Name - L-Threonine, N-[5-[(3aS,4S,6aR)-hexahydro-2-oxo-1H-thieno[3,4-d]imidazol-4-yl]-1-oxopentyl]-L-seryl-L-glutaminyl-L-asparaginyl-L-tyrosyl-Lprolyl-L-isoleucyl-L-valyl-β-alanyl-L-arginyl-Lglutaminyl-L-seryl-L-threonyl-L-prolyl-L-isoleucylglycyl-L-leucylglycyl-L-glutaminyl-L-alanyl-L-leucyl-L-tyrosyl-L-threonyl-

98.

CAS Registry Number: 384828-77-7

MF - C77 H134 N34 O17 S

Name - L-Phenylalaninamide, N-[5-[(3aS,4S,6aR)-hexahydro-2-oxo-1H-thieno[3,4-d]imidazol-4-yl]-1-oxopentyl]-L-threonyl-L-arginyl-L-arginyl-L-seryl-L-lysyl-L-arginyl-L-arginyl-L-seryl-L-histidyl-L-arginyl-L-lysyl-

99.

CAS Registry Number: 384828-52-8

Name - L-Lysinamide, N-[5-[(3aS,4S,6aR)-hexahydro-2-oxo-1H-thieno[3,4-d]imidazol-4-yl]-1-oxopentyl]-L-seryl-L-tryptophyl-L-leucylglycyl-L-arginyl-Lglutaminyl-L-leucyl-L-arginyl-L-isoleucyl-L-alanylglycyl-L-lysyl-L-arginyl-L-leucyl-L-α-glutamylglycyl-L-arginyl-L-seryl-

100.

CAS Registry Number: 378788-32-0

MF - C53 H82 N14 O25 S2
Name - L-Glutamic acid, N-[5-[(3aS,4S,6aR)-hexahydro-2-oxo-1H-thieno[3,4-d]imidazol-4-yl]-1-oxopentyl]-L-seryl-L-isoleucyl-L-α-glutamyl-L-glutaminyl-L-seryl-L-cysteinyl-L-α-aspartyl-Lglutaminyl-L-α-aspartyl-

101.

CAS Registry Number: 372166-23-9

MF - C60 H98 N18 O19 S
Name - L-Lysine, N-[5-[(3aS,4S,6aR)-hexahydro-2-oxo-1H-thieno[3,4-d]imidazol-4-yl]-1-oxopentyl]-Lserylglycyl-L-serylglycyl-L-leucylglycyl-Lisoleucyl-L-seryl-L-tyrosylglycyl-L-arginyl-

102.

CAS Registry Number: 366493-76-7
MF - C132 H219 N39 O39 S3
Name - L-Tyrosinamide, N-[5-[(3aS,4S,6aR)-hexahydro-2-oxo-1H-thieno[3,4-d]imidazol-4-yl]-1-oxopentyl]-L-seryl-L-glutaminyl-L-alanyl-L-valyl-L-glutaminyl-L-α-glutamyl-L-histidyl-L-alanyl-Lseryl-L-threonyl-L-asparaginyl-L-methionylglycyl-L-leucyl-L-α-glutamyl-L-alanyl-L-isoleucyl-L-isoleucyl-L-arginyl-L-lysyl-L-alanyl-L-leucyl-L-methionylglycyl-L-lysyl-

103.

CAS Registry Number: 366493-66-5
MF - C128 H220 N38 O40 S
Name - Glycinamide, N-[5-[(3aS,4S,6aR)-hexahydro-2-oxo-1H-thieno[3,4-d]imidazol-4-yl]-1-oxopentyl]-L-serylglycyl-L-seryl-L-α-glutamyl-L-isoleucyl-L-α-glutamyl-L-asparaginyl-L-leucyl-L-leucyl-L-α-glutamyl-L-arginyl-L-arginyl-L-threonyl-L-valyl-L-leucyl-L-glutaminyl-L-leucyl-L-leucyl-L-leucylglycyl-L-asparaginyl-L-prolyl-L-threonyl-L-lysyl-

CAS Registry Number: 366493-65-4

MF - C134 H227 N41 O40 S

Name - L-α-Glutamine, N-[5-[(3aS,4S,6aR)-hexahydro-2-oxo-1H-thieno[3,4-d]imidazol-4-yl]-1-oxopentyl]-L-seryl-L-lysyl-L-asparaginyl-L-seryl-L-lysyl-L-leucyl-L-asparaginyl-L-seryl-L-histidyl-L-glutaminyl-L-lysyl-L-valyl-L-threonyl-L-leucyl-L-leucyl-L-glutaminyl-L-leucyl-L-leucyl-L-leucylglycyl-L-histidyl-L-lysyl-L-asparaginyl-L-α-glutamyl-

105.

CAS Registry Number: 366493-64-3

MF - C132 H226 N42 O38 S

Name - L-Glutamamide, N-[5-[(3aS,4S,6aR)-hexahydro-2-oxo-1H-thieno[3,4-d]imidazol-4-yl]-1-oxopentyl]-L-seryl-L-leucyl-L-glutaminyl-Lasparaginyl-L-leucyl-L-lysyl-L-asparaginyl-L-leucylglycyl-L-α-glutamyl-L-seryl-L-alanyl-Lthreonyl-L-leucyl-L-arginyl-L-seryl-L-leucyl-Lleucyl-L-leucyl-L-asparaginyl-L-prolyl-L-histidyl-L-leucyl-L-arginyl-

106.

CAS Registry Number: 366493-60-9

MF - C142 H231 N45 O36 S2

Name - L-Cysteinamide, N-[5-[(3aS,4S,6aR)-hexahydro-2-oxo-1H-thieno[3,4-d]imidazol-4-yl]-1-oxopentyl]-L-threonyl-L-lysyl-L-phenylalanyl-Lvalyl-L-asparaginyl-L-leucyl-L-tyrosyl-L-threonyl-L-arginyl-L-α-glutamyl-L-arginyl-L-glutaminyl-L-α-aspartyl-L-arginyl-L-leucyl-L-alanyl-L-valyl-L-leucyl-L-leucyl-L-prolylglycyl-L-arginyl-L-histidyl-L-prolyl-

107.

CAS Registry Number: 366493-54-1

MF - C142 H240 N46 O35 S2

Name - L-Alaninamide, N-[5-[(3aS,4S,6aR)-hexahydro-2-oxo-1H-thieno[3,4-d]imidazol-4-yl]-1-oxopentyl]-L-seryl-L-threonyl-L-alanyl-L-leucyl-L-leucyl-L-tyrosyl-L-seryl-L-lysyl-L-arginyl-L-leucyl-L-isoleucyl-L-threonyl-L-tyrosyl-L-arginyl-L-leucyl-L-arginyl-L-histidyl-L-leucyl-L-leucyl-L-arginyl-L-alanyl-L-arginyl-L-cysteinyl-L-α-aspartyl-

CAS Registry Number: 366493-46-1

MF - C130 H220 N40 O42 S2

Name - L-Leucinamide, N-[5-[(3aS,4S,6aR)-hexahydro-2-oxo-1H-thieno[3,4-d]imidazol-4-yl]-1-oxopentyl]-L-seryl-L-leucylglycyl-L-methionyl-L-valyl-L-glutaminyl-L-α-aspartyl-L-alanyl-L-alanyl-L-seryl-L-lysyl-L-histidyl-L-lysyl-L-glutaminyl-L-leucyl-L-seryl-L-α-glutamyl-L-leucyl-L-leucyl-L-arginyl-L-serylglycyl-L-seryl-L-seryl-L-prolyl-L-asparaginyl-

109.

CAS Registry Number: 366493-43-8

MF - C140 H230 N46 O41 S2

Name - L-α-Glutamine, N-[5-[(3aS,4S,6aR)-hexahydro-2-oxo-1H-thieno[3,4-d]imidazol-4-yl]-1-oxopentyl]-L-seryl-L-asparaginyl-L-methionyl-L-histidylglycyl-L-seryl-L-leucyl-L-leucyl-L-glutaminyl-L-α-glutamyl-L-lysyl-L-histidyl-L-arginyl-L-isoleucyl-L-leucyl-L-histidyl-L-lysyl-L-leucyl-L-leucyl-L-glutaminyl-L-asparaginylglycyl-L-asparaginyl-L-seryl-L-prolyl-L-alanyl-

110.

CAS Registry Number: 366493-39-2

MF - C119 H203 N35 O35 S

Name - L-Prolinamide, N-[5-[(3aS,4S,6aR)-hexahydro-2-oxo-1H-thieno[3,4-d]imidazol-4-yl]-1-oxopentyl]-L-seryl-L-valyl-L-glutaminyl-L-prolyl-L-prolyl-L-arginyl-L-seryl-L-isoleucyl-L-seryl-L-prolyl-L-seryl-L-alanyl-L-leucyl-L-glutaminyl-L-α-aspartyl-L-leucyl-L-leucyl-L-arginyl-L-threonyl-L-leucyl-L-lysyl-L-seryl-

111.

CAS Registry Number: 351999-11-6

C45 H68 N12 O17 S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-seryl-

112.

CAS Registry Number: 351999-10-5

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-seryl-L-leucyl-L-lysyl-L-alanyl-L-asparaginyl-L-valyl-L-tyrosyl-

113.

CAS Registry Number: 351999-02-5

MF - C79 H120 N20 O26 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-serylglycyl-L-leucyl-L-lysyl-L-leucyl-L-asparaginyl-L-valyl-L-tyrosyl-

114.

CAS Registry Number: 351999-01-4

MF - C80 H122 N20 O26 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-alanyl-L-leucyl-L-lysyl-L-leucyl-L-asparaginyl-L-valyl-L-tyrosyl-

115.

CAS Registry Number: 351999-00-3

MF - C76 H114 N20 O27 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-serylglycyl-L-lysyl-L-leucyl-L-asparaginyl-L-valyl-L-tyrosyl-

116.

CAS Registry Number: 351998-99-7

MF - C77 H116 N20 O27 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-seryl-L-alanyl-L-lysyl-L-leucyl-L-asparaginyl-L-valyl-L-tyrosyl-

117.

CAS Registry Number: 351998-98-6

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-seryl-L-leucylglycyl-L-leucyl-L-asparaginyl-L-valyl-L-tyrosyl-

118.

CAS Registry Number: 351998-97-5

MF - C77 H115 N19 O27 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-seryl-L-leucyl-L-alanyl-L-leucyl-L-asparaginyl-L-valyl-L-tyrosyl-

119.

CAS Registry Number: 351998-96-4

MF - C76 H114 N20 O27 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-seryl-L-leucyl-L-lysylglycyl-L-asparaginyl-L-valyl-L-tyrosyl-

120.

CAS Registry Number: 351998-95-3

MF - C80 H122 N20 O27 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-L-phenylalanyl-L-seryl-L-seryl-L-leucyl-L-lysyl-L-leucyl-L-asparaginyl-L-valyl-L-tyrosyl-

121.

CAS Registry Number: 351998-94-2

MF - C76 H116 N18 O25 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-phenylalanyl-L-seryl-L-seryl-L-leucyl-L-lysyl-L-leucyl-L-asparaginyl-L-valyl-L-tyrosyl-

122.

CAS Registry Number: 351998-93-1

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-seryl-Lseryl-L-leucyl-L-lysyl-L-leucyl-L-asparaginyl-L-valyl-L-tyrosyl-

123.

CAS Registry Number: 351998-92-0

MF - C64 H102 N16 O22 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-seryl-L-leucyl-L-lysyl-L-leucyl-L-asparaginyl-L-valyl-L-tyrosyl-

124.

CAS Registry Number: 351998-91-9

MF - C61 H97 N15 O20 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-leucyl-L-lysyl-L-leucyl-L-asparaginyl-L-valyl-L-tyrosyl-

125.

CAS Registry Number: 351998-90-8

MF - C55 H86 N14 O19 S

Name - L-Glutamic acid, N-[5-[(3aS,4S,6aR)-hexahydro-2-oxo-1H-thieno[3,4-d]imidazol-4-yl]-1-oxopentyl]-L-serylglycyl-L-serylglycyl-L-lysyl-L-leucyl-L-asparaginyl-L-valyl-L-tyrosyl-

126.

CAS Registry Number: 351998-89-5

MW - C75 H115 N19 O24 S

Name - L-Tyrosine, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-Lphenylalanyl-L-seryl-L-seryl-L-leucyl-L-lysyl-L-leucyl-L-asparaginyl-L-valyl-

127.

CAS Registry Number: 351998-88-4

MW - C66 H106 N18 O22 S

Name - L-Valine, N-[5-[(3aS,4S,6aR)-hexahydro-2-oxo-1H-thieno[3,4-d]imidazol-4-yl]-1-oxopentyl]-Lserylglycyl-L-serylglycyl-L-asparaginyl-Lphenylalanyl-L-seryl-L-seryl-L-leucyl-L-lysyl-L-leucyl-L-asparaginyl-

CAS Registry Number: 351998-87-3

MW - C61 H97 N17 O21 S

Name - L-Asparagine, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-Lphenylalanyl-L-seryl-L-seryl-L-leucyl-L-lysyl-L-leucyl-

129.

CAS Registry Number: 351998-86-2

MW - C57 H91 N15 O19 S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-asparaginyl-Lphenylalanyl-L-seryl-L-seryl-L-leucyl-L-lysyl-

130.

CAS Registry Number: 351858-61-2

MW - C26 H42 N6 O9 S

Name - L-Alaninamide, N-[5-[(3aS,4S,6aR)-hexahydro-2-oxo-1H-thieno[3,4-d]imidazol-4-yl]-1-oxopentyl]-L-threonyl-L-valyl-N-[(1S)-2-carboxy-1-formylethyl]-

131.

CAS Registry Number: 345894-77-1

MW - C81 H127 N19 O32 S2

Name - L-Lysine, N-[5-[(3aS,4S,6aR)-hexahydro-2-oxo-1H-thieno[3,4-d]imidazol-4-yl]-1-oxopentyl]-Lseryl-L-serylglycyl-L-alanyl-L-α-aspartyl-Lthreonyl-L-α-glutamyl-L-α-aspartyl-L-valyl-Lvalyl-L-alanyl-(2S)-2-aminobutanoyl-(2S)-2-hydroxypropanoyl-L-methionyl-L-seryl-L-tyrosyl-

132.

CAS Registry Number: 345231-92-7

MW - C82 H123 N23 O24 S

Name - L-Lysine, N-[5-[(3aS,4S,6aR)-hexahydro-2-oxo-1H-thieno[3,4-d]imidazol-4-yl]-1-oxopentyl]-L-threonyl-L-arginyl-L-asparaginyl-L-isoleucyl-L-tyrosyl-L-α-glutamyl-L-threonyl-L-asparaginyl-Ltyrosyl-L-tyrosyl-L-arginyl-

CAS Registry Number: 303175-72-6

MW - C76 H114 N17 O32 P S

Name - L-Isoleucine, N-[5-[(3aS,4S,6aR)-hexahydro-2-oxo-1H-thieno[3,4-d]imidazol-4-yl]-1-oxopentyl]-L-serylglycyl-L-serylglycyl-L-α-glutamyl-L-α-glutamyl-L-prolyl-L-glutaminyl-O-phosphono-L-tyrosyl-L-α-glutamyl-L-α-glutamyl-L-isoleucyl-L-prolyl-

134.

CAS Registry Number: 278597-07-2

MW - C140 H229 N45 O42 S2

Name - L-Glutamic acid, N-[5-[(3aS,4S,6aR)-hexahydro-2-oxo-1H-thieno[3,4-d]imidazol-4-yl]-1-oxopentyl]-L-seryl-L-asparaginyl-L-methionyl-L-histidylglycyl-L-seryl-L-leucyl-L-leucyl-Lglutaminyl-L-α-glutamyl-L-lysyl-L-histidyl-L-arginyl-L-isoleucyl-L-leucyl-L-histidyl-L-lysyl-L-leucyl-L-leucyl-L-glutaminyl-L-asparaginylglycyl-L-asparaginyl-L-seryl-L-prolyl-L-alanyl-

135.

CAS Registry Number: 251463-47-5

MW - C70 H112 N21 O30 P S

Name - L-Tyrosine, N-[5-[(3aS,4S,6aR)-hexahydro-2-oxo-1H-thieno[3,4-d]imidazol-4-yl]-1-oxopentyl]-L-serylglycyl-L-serylglycylglycylglycyl-L-lysyl-L-lysyl-L-alanyl-L-threonyl-L-glutaminyl-Ophosphono-L-seryl-L-glutaminyl-L-α-glutamyl-

136.

CAS Registry Number: 251463-46-4

MW - C70 H111 N21 O27 S

Name - L-Tyrosine, N-[5-[(3aS,4S,6aR)-hexahydro-2-oxo-1H-thieno[3,4-d]imidazol-4-yl]-1-oxopentyl]-L-serylglycyl-L-serylglycylglycylglycyl-L-lysyl-L-lysyl-L-alanyl-L-threonyl-L-glutaminyl-L-seryl-Lglutaminyl-L-α-glutamyl-

137.

CAS Registry Number: 251463-45-3

MW - C100 H151 N24 O35 P S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-Lprolyl-L-leucyl-L-seryl-L-glutaminyl-L-

Figure 10 (cont)

α-glutamyl-O-phosphono-L-seryl-L-phenylalanyl-L-seryl-L-α-aspartyl-L-leucyl-L-tryptophyl-L-lysyl-

138.

CAS Registry Number: 251463-44-2

MW - C64 H104 N18 O25 S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-leucyl-L-alanyl-L-alanyl-L-alanyl-L-α-aspartyl-L-alanyl-Lalanyl-L-α-aspartyl-L-alanyl-L-alanyl-

139.

CAS Registry Number: 251463-43-1

MW - C64 H107 N18 O27 P S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-leucyl-L-alanyl-L-alanyl-O-phosphono-Lthreonyl-L-alanyl-L-alanyl-L-α-aspartyl-L-alanyl-L-alanyl-

140.

CAS Registry Number: 251463-42-0

MW - C100 H153 N24 O33 P S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-L-seryl-L-glutaminyl-L-α-glutamyl-O-phosphono-L-threonyl-L-phenylalanyl-L-seryl-L-alanyl-L-leucyl-L-tryptophyl-L-lysyl-

141.

CAS Registry Number: 251463-41-9

MW - C101 H153 N24 O34 P S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-L-seryl-L-glutaminyl-L-α-glutamyl-O-phosphono-L-threonyl-L-phenylalanyl-L-alanyl-L-α-aspartyl-L-leucyl-L-tryptophyl-L-lysyl-

142.

CAS Registry Number: 251463-39-5

Figure 10 (cont)

MW - C95 H149 N24 O35 P S
Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-L-seryl-L-glutaminyl-L-α-glutamyl-O-phosphono-L-threonyl-L-alanyl-L-seryl-L-α-aspartyl-L-leucyl-L-tryptophyl-L-lysyl-

143.

CAS Registry Number: 251463-38-4
MW - C99 H151 N24 O33 P S
Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-L-seryl-L-glutaminyl-L-alanyl-O-phosphono-L-threonyl-L-phenylalanyl-L-seryl-L-α-aspartyl-L-leucyl-L-tryptophyl-L-lysyl-

144.

CAS Registry Number: 251463-37-3
MW - C99 H150 N23 O34 P S
Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-L-seryl-L-alanyl-L-α-glutamyl-O-phosphono-L-threonyl-L-phenylalanyl-L-seryl-L-α-aspartyl-L-leucyl-L-tryptophyl-L-lysyl-

145.

CAS Registry Number: 251463-36-2
MW - C101 H153 N24 O34 P S
Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-L-alanyl-L-glutaminyl-L-α-glutamyl-O-phosphono-L-threonyl-L-phenylalanyl-L-seryl-L-α-aspartyl-L-leucyl-L-tryptophyl-L-lysyl-

146.

CAS Registry Number: 251463-35-1
MW - C101 H153 N24 O35 P S
Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-L-seryl-L-glutaminyl-

Figure 10 (cont)

L-α-glutamyl-O-phosphono-L-threonyl-L-phenylalanyl-L-seryl-L-α-aspartyl-L-leucyl-L-tryptophyl-L-lysyl-

147.

CAS Registry Number: 251463-34-0

MW - C101 H153 N24 O35 P S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-O-phosphono-L-seryl-L-glutaminyl-L-α-glutamyl-L-threonyl-Lphenylalanyl-L-seryl-L-α-aspartyl-L-leucyl-L-tryptophyl-L-lysyl-

148.

CAS Registry Number: 251463-33-9

MW - C101 H152 N24 O32 S

Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-prolyl-L-prolyl-L-leucyl-L-seryl-L-glutaminyl-L-α-glutamyl-L-threonyl-L-phenylalanyl-L-seryl-L-α-aspartyl-L-leucyl-L-tryptophyl-L-lysyl-

149.

CAS Registry Number: 215930-34-0

MW - C107 H151 N25 O36 S2

Name - L-Leucinamide, N-[5-[(3aS,4S,6aR)-hexahydro-2-oxo-1H-thieno[3,4-d]imidazol-4-yl]-1-oxopentyl]-L-serylglycyl-L-serylglycyl-L-prolyl-L-phenylalanyl-L-valyl-L-tryptophyl-L-α-aspartyl-L-α-glutamyl-L-α-aspartyl-L-cysteinyl-L-phenylalanyl-L-α-glutamyl-L-alanyl-L-alanyl-L-lysyl-L-α-aspartyl-L-α-glutamyl-

150.

CAS Registry Number: 201984-65-8

201984-64-7

MW - C93 H134 N22 O28 S 76-05-1

C2 H F3 O2

C93 H134 N22 O28 S . x C2 H F3 O2

Name - L-Prolinamide, N-[5-[(3aS,4S,6aR)-hexahydro-2-oxo-1H-thieno[3,4-d]imidazol-4-yl]-1-oxopentyl]-L-serylglycyl-L-serylglycyl-L-glutaminyl-L-α-glutamyl-L-threonyl-L-phenylalanyl-L-seryl-L-α-aspartyl-L-tyrosyl-L-tryptophyl-L-lysyl-L-leucyl-L-leucyl-,trifluoroacetate (salt)

CAS Registry Number: 201984-64-7

MW - C93 H134 N22 O28 S

Name - L-Prolinamide, N-[5-[(3aS,4S,6aR)-hexahydro-2-oxo-1H-thieno[3,4-d]imidazol-4-yl]-1-oxopentyl]-L-serylglycyl-L-serylglycyl-L-glutaminyl-L-α-glutamyl-L-threonyl-L-phenylalanyl-L-seryl-L-α-aspartyl-L-tyrosyl-L-tryptophyl-L-lysyl-L-leucyl-L-leucyl-

152.

CAS Registry Number: 201984-63-6

MW - 201984-62-5

C90 H136 N22 O25 S 76-05-1

C2 H F3 O2

C90 H136 N22 O25 S . x C2 H F3 O2

Name - L-Prolinamide, N-[5-[(3aS,4S,6aR)-hexahydro-2-oxo-1H-thieno[3,4-d]imidazol-4-yl]-1-oxopentyl]-L-serylglycyl-L-serylglycyl-L-glutaminyl-L-prolyl-L-threonyl-L-phenylalanyl-L-seryl-L-α-aspartyl-L-leucyl-L-tryptophyl-L-lysyl-L-leucyl-L-leucyl-, trifluoroacetate (salt)

153.

CAS Registry Number: 201984-62-5

MW - C90 H136 N22 O25 S

Name - L-Prolinamide, N-[5-[(3aS,4S,6aR)-hexahydro-2-oxo-1H-thieno[3,4-d]imidazol-4-yl]-1-oxopentyl]-L-serylglycyl-L-serylglycyl-Lglutaminyl-L-prolyl-L-threonyl-L-phenylalanyl-L-seryl-L-α-aspartyl-L-leucyl-L-tryptophyl-L-lysyl-L-leucyl-L-leucyl-

154.

CAS Registry Number: 201984-61-4

201984-60-3

MW - C90 H136 N22 O27 S 76-05-1

C2 H F3 O2

C90 H136 N22 O27 S . x C2 H F3 O2

Name - L-Prolinamide, N-[5-[(3aS,4S,6aR)-hexahydro-2-oxo-1H-thieno[3,4-d]imidazol-4-yl]-1-oxopentyl]-L-serylglycyl-L-serylglycyl-Lglutaminyl-L-α-glutamyl-L-threonyl-Lphenylalanyl-L-seryl-L-α-aspartyl-L-leucyl-L-tryptophyl-L-lysyl-L-leucyl-L-leucyl-,trifluoroacetate (salt)

CAS Registry Number: 201984-60-3

MW - C90 H136 N22 O27 S

Name - L-Prolinamide, N-[5-[(3aS,4S,6aR)-hexahydro-2-oxo-1H-thieno[3,4-d]imidazol-4-yl]-1-oxopentyl]-L-serylglycyl-L-serylglycyl-L-glutaminyl-L-α-glutamyl-L-threonyl-L-phenylalanyl-L-seryl-L-α-aspartyl-L-leucyl-L-tryptophyl-L-lysyl-L-leucyl-L-leucyl-

156.

CAS Registry Number: 201746-19-2

MW - C28 H49 Cl N10 O7 S

Name - Glycinamide, N-[5-[(3aS,4S,6aR)-hexahydro-2-oxo-1H-thieno[3,4-d]imidazol-4-yl]-1-oxopentyl]-L-seryl-L-lysyl-N-[(1S)-4-[(aminoiminomethyl)amino]-1-(chloroacetyl)butyl]-

157.

CAS Registry Number: 198338-78-2

MW - C148 H225 N43 O42 S3

Name - Somatostatin-28 (sheep), N-[5-[(3aS,4S,6aR)-hexahydro-2-oxo-1H-thieno[3,4-d]imidazol-4-yl]-1-oxopentyl]-8-L-leucine-22-D-tryptophan-25-L-tyrosine-

158.

CAS Registry Number: 192221-25-3

MW - C35 H57 N10 O12 S Y

Name - Yttrium-90Y, [N-[5-[(3aS,4S,6aR)-hexahydro-2-oxo-1H-thieno[3,4-d]imidazol-4-yl]-1-oxopentyl]-D-seryl-N6-[[4,7,10-tris[(carboxy-κO)methyl]-1,4,7,10-tetraazacyclododec-1-yl-κN1,κN4,κN7,κN10]acetyl-κO]-D-lysinamidato(3-)]-

159.

CAS Registry Number: 192221-22-0

MW - C35 H57 N10 O12 S Y

Name - Yttrium-88Y, [N-[5-[(3aS,4S,6aR)-hexahydro-2-oxo-1H-thieno[3,4-d]imidazol-4-yl]-1-oxopentyl]-D-seryl-N6-[[4,7,10-tris[(carboxy-κO)methyl]-1,4,7,10-tetraazacyclododec-1-yl-κN1,κN4,κN7,κN10]acetyl-κO]-D-lysinamidato(3-)]-

160.

CAS Registry Number: 192221-19-5

Name - D-Lysinamide, N-[5-[(3aS,4S,6aR)-hexahydro-2-oxo-1H-thieno[3,4-d]imidazol-4-yl]-1-oxopentyl]-D-seryl-N6-[[4,7,10-tris(carboxymethyl)-1,4,7,10-tetraazacyclododec-1-yl]acetyl]-

161.

CAS Registry Number: 189328-76-5

MW - C77 H121 N20 O31 P S

Name - L-α-Asparagine, N-[5-[(3aS,4S,6aR)-hexahydro-2-oxo-1H-thieno[3,4-d]imidazol-4-yl]-1-oxopentyl]-L-threonyl-L-seryl-L-seryl-L-valyl-L-leucyl-O-phosphono-L-tyrosyl-L-threonyl-L-alanyl-L-valyl-L-glutaminyl-L-prolyl-Lasparaginyl-L-α-glutamylglycyl-

162.

CAS Registry Number: 189328-70-9

MW - C93 H138 N25 O32 P S

Name - L-Alaninamide, N-[5-[(3aS,4S,6aR)-hexahydro-2-oxo-1H-thieno[3,4-d]imidazol-4-yl]-1-oxopentyl]-L-serylglycyl-L-leucyl-Lglutaminylglycyl-L-histidyl-L-isoleucyl-Lisoleucyl-L-α-glutamyl-L-asparaginyl-L-prolyl-Lglutaminyl-O-phosphono-L-tyrosyl-Lphenylalanyl-L-seryl-L-α-aspartyl-

163.

CAS Registry Number: 187405-63-6

MW - C55 H95 N17 O19 S

Name - L-Alanine, N-[5-[(3aS,4S,6aR)-hexahydro-2-oxo-1H-thieno[3,4-d]imidazol-4-yl]-1-oxopentyl]-L-serylglycyl-L-serylglycyl-L-alanyl-L-seryl-L-leucyl-L-arginyl-L-seryl-L-leucyl-L-valyl-

164.

CAS Registry Number: 187405-62-5

C61 H99 N17 O20 S

Name - L-Valine, N-[5-[(3aS,4S,6aR)-hexahydro-2-oxo-1H-thieno[3,4-d]imidazol-4-yl]-1-oxopentyl]-L-serylglycyl-L-serylglycyl-L-tyrosyl-L-alanyl-L-seryl-L-leucyl-L-arginyl-L-seryl-L-leucyl-

165.

CAS Registry Number: 187405-61-4

Figure 10 (cont)

MW - C60 H95 N17 O22 S
Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-α-aspartyl-L-tyrosyl-L-alanyl-L-seryl-L-leucyl-L-arginyl-L-seryl-

166.

CAS Registry Number: 187405-60-3
C59 H91 N17 O22 S
Name - L-Serine, N-[5-[(3aS,4S,6aR)-hexahydro-2-oxo-1H-thieno[3,4-d]imidazol-4-yl]-1-oxopentyl]-Lserylglycyl-L-serylglycyl-L-prolyl-L-α-aspartyl-L-tyrosyl-L-alanyl-L-seryl-L-leucyl-L-arginyl-

167.

CAS Registry Number: 187405-59-0
MW - C61 H95 N17 O21 S
Name - L-Arginine, N-[5-[(3aS,4S,6aR)-hexahydro-2-oxo-1H-thieno[3,4-d]imidazol-4-yl]-1-oxopentyl]-L-serylglycyl-L-serylglycyl-L-valyl-L-prolyl-L-α-aspartyl-L-tyrosyl-L-alanyl-L-seryl-L-leucyl-

168.

CAS Registry Number: 187405-58-9
MW - C59 H88 N14 O23 S
Name - L-Leucine, N-[5-[(3aS,4S,6aR)-hexahydro-2-oxo-1H-thieno[3,4-d]imidazol-4-yl]-1-oxopentyl]-L-serylglycyl-L-serylglycyl-L-α-aspartyl-L-valyl-Lprolyl-L-α-aspartyl-L-tyrosyl-L-alanyl-L-seryl-

169.

CAS Registry Number: 187405-57-8
MW - C58 H84 N14 O23 S
Name - L-Serine, N-[5-[(3aS,4S,6aR)-hexahydro-2-oxo-1H-thieno[3,4-d]imidazol-4-yl]-1-oxopentyl]-Lserylglycyl-L-serylglycyl-L-prolyl-L-α-aspartyl-L-valyl-L-prolyl-L-α-aspartyl-L-tyrosyl-L-alanyl-

170.

CAS Registry Number: 187405-56-7
MW - C64 H88 N14 O23 S

Figure 10 (cont)

Name - L-Alanine, N-[5-[(3aS,4S,6aR)-hexahydro-2-oxo-1H-thieno[3,4-d]imidazol-4-yl]-1-oxopentyl]-L-serylglycyl-L-serylglycyl-L-prolyl-L-tyrosyl-L-α-aspartyl-L-valyl-L-prolyl-L-α-aspartyl-L-tyrosyl-

171.

CAS Registry Number: 187405-55-6

MW - C70 H92 N14 O24 S
Name - L-Tyrosine, N-[5-[(3aS,4S,6aR)-hexahydro-2-oxo-1H-thieno[3,4-d]imidazol-4-yl]-1-oxopentyl]-L-serylglycyl-L-serylglycyl-L-tyrosyl-L-prolyl-Ltyrosyl-L-α-aspartyl-L-valyl-L-prolyl-L-α-aspartyl-

172.

CAS Registry Number: 187405-54-5
MW - C64 H88 N14 O23 S2
Name - L-Aspartic acid, N-[5-[(3aS,4S,6aR)-hexahydro-2-oxo-1H-thieno[3,4-d]imidazol-4-yl]-1-oxopentyl]-L-serylglycyl-L-serylglycyl-Lcysteinyl-L-tyrosyl-L-prolyl-L-tyrosyl-L-α-aspartyl-L-valyl-L-prolyl-

173.

CAS Registry Number: 187405-53-4
MW - C64 H89 N15 O22 S2
Name - L-Proline, N-[5-[(3aS,4S,6aR)-hexahydro-2-oxo-1H-thieno[3,4-d]imidazol-4-yl]-1-oxopentyl]-Lserylglycyl-L-serylglycyl-L-asparaginyl-Lcysteinyl-L-tyrosyl-L-prolyl-L-tyrosyl-L-α-aspartyl-L-valyl-

174.

CAS Registry Number: 187405-52-3
MW – C62 H87 N15 O23 S2
Name - L-Valine, N-[5-[(3aS,4S,6aR)-hexahydro-2-oxo-1H-thieno[3,4-d]imidazol-4-yl]-1-oxopentyl]-Lserylglycyl-L-serylglycyl-L-seryl-L-asparaginyl-Lcysteinyl-L-tyrosyl-L-prolyl-L-tyrosyl-L-α-aspartyl-

175.

CAS Registry Number: 179244-17-8
MW - C42 H64 N8 O14 S

Figure 10 (cont)

Name - L-Leucine, N-[N-[N-[N-[N-[N-[5-(hexahydro-2-oxo-1H-thieno[3,4-d]imidazol-4-yl)-1-oxopentyl]-L-threonyl]-L-valyl]-L-seryl]-L-tyrosyl]-L-α-glutamyl]-, [3aS-(3aα,4β,6aα)]-

176.

CAS Registry Number: 177353-34-3

MW - C123 H199 N37 O34 S

Name -L-Argininamide, N-[5-(hexahydro-2-oxo-1Hthieno[3,4-d]imidazol-4-yl)-1-oxopentyl]-Lserylglycyl-L-serylglycyl-L-seryl-L-arginyl-Lleucyl-L-threonyl-L-prolyl-L-glutaminyl-L-seryl-Llysyl-L-prolyl-L-prolyl-L-leucyl-L-prolyl-L-prolyl-L-lysyl-L-prolyl-L-seryl-L-tryptophyl-L-valyl-L-seryl-, [3aS-(3aα,4β,6aα)]-

177.

CAS Registry Number: 177353-33-2

MW - C80 H134 N26 O22 S

Name -L-Argininamide, N-[5-(hexahydro-2-oxo-1Hthieno[3,4-d]imidazol-4-yl)-1-oxopentyl]-L-serylglycyl-L-serylglycyl-L-isoleucyl-L-leucyl-Lalanyl-L-prolyl-L-prolyl-L-valyl-L-prolyl-L-prolyl-L-arginyl-L-asparaginyl-L-threonyl-, [3aS-(3aα,4β,6aα)]-

178.

CAS Registry Number: 174138-09-1

MW - C73 H110 N20 O27 S

Name -Glycine, N-[5-(hexahydro-2-oxo-1H-thieno[3,4-d]imidazol-4-yl)-1-oxopentyl]-L-threonyl-L-seryl-L-prolyl-L-threonyl-L-seryl-L-prolyl-L-threonyl-Lseryl-L-prolyl-L-threonyl-L-seryl-L-prolyl-N6-(4-azido-2-hydroxybenzoyl)-L-lysyl-, [3aS-(3aα,4β,6aα)]-

179.

CAS Registry Number: 171778-68-0

MW - C97 H155 N29 O32 S2

Name -L-Aspartic acid, N-[5-(hexahydro-2-oxo-1Hthieno[3,4-d]imidazol-4-yl)-1-oxopentyl]-Lserylglycyl-L-serylglycyl-L-arginyl-L-histidyl-L-lysyl-L-lysyl-L-leucyl-L-methionyl-L-phenylalanyl-L-lysyl-L-threonyl-L-α-glutamylglycyl-L-prolyl-L-α-aspartyl-L-seryl-,[3aS-(3aα,4β,6aα)]-

180.

CAS Registry Number: 171778-67-9

Name -L-Arginine, N-[5-(hexahydro-2-oxo-1Hthieno[3,4-d]imidazol-4-yl)-1-oxopentyl]-L-serylglycyl-L-serylglycyl-L-leucyl-L-lysyl-L-seryl-L-lysyl-L-lysylglycyl-L-glutaminyl-L-seryl-L-threonyl-L-seryl-, [3aS-(3aα,4β,6aα)]-

181.

CAS Registry Number: 171778-66-8

MW - C73 H126 N26 O24 S

Name -L-Leucine, N-[5-(hexahydro-2-oxo-1Hthieno[3,4-d]imidazol-4-yl)-1-oxopentyl]-Lserylglycyl-L-serylglycyl-L-lysylglycyl-Lglutaminyl-L-seryl-L-threonyl-L-seryl-L-arginyl-L-histidyl-L-lysyl-L-lysyl-, [3aS-(3aα,4β,6aα)]-

182.

CAS Registry Number: 171778-65-7

MW - C82 H143 N29 O27 S

Name -L-Lysine, N-[5-(hexahydro-2-oxo-1H-thieno[3,4-d]imidazol-4-yl)-1-oxopentyl]-L-serylglycyl-Lserylglycyl-L-leucyl-L-lysyl-L-seryl-L-lysyl-L-lysylglycyl-L-glutaminyl-L-seryl-L-threonyl-Lseryl-L-arginyl-L-histidyl-, [3aS-(3aα,4β,6aα)]-

183.

CAS Registry Number: 171778-64-6

MW - C79 H138 N28 O25 S

Name -L-Leucine, N-[5-(hexahydro-2-oxo-1Hthieno[3,4-d]imidazol-4-yl)-1-oxopentyl]-L-serylglycyl-L-serylglycyl-L-lysyl-L-lysylglycyl-Lglutaminyl-L-seryl-L-threonyl-L-seryl-L-arginyl-L-histidyl-L-lysyl-L-lysyl-, [3aS-(3aα,4β,6aα)]-

184.

CAS Registry Number: 171778-63-5

MW - C94 H166 N32 O29 S

Name -L-Leucine, N-[5-(hexahydro-2-oxo-1Hthieno[3,4-d]imidazol-4-yl)-1-oxopentyl]-L-serylglycyl-L-serylglycyl-L-leucyl-L-lysyl-L-seryl-L-lysyl-L-lysylglycyl-L-glutaminyl-L-seryl-L-threonyl-L-seryl-L-arginyl-L-histidyl-L-lysyl-Llysyl-,[3aS-(3aα,4β,6aα)]-

185.

CAS Registry Number: 171778-62-4

Name -L-Phenylalanine, N-[5-(hexahydro-2-oxo-1Hthieno[3,4-d]imidazol-4-yl)-1-oxopentyl]-Lserylglycyl-L-serylglycyl-L-seryl-L-lysyl-L-lysylglycyl-L-glutaminyl-L-seryl-L-threonyl-L-seryl-L-arginyl-L-histidyl-L-lysyl-L-lysyl-L-leucyl-L-methionyl-, [3aS-(3aα,4β,6aα)]-

186.

CAS Registry Number: 171778-61-3

MW - C96 H157 N29 O30 S2

Name -L-Proline, N-[5-(hexahydro-2-oxo-1H-thieno[3,4-d]imidazol-4-yl)-1-oxopentyl]-L-serylglycyl-Lserylglycyl-L-seryl-L-threonyl-L-seryl-L-arginyl-Lhistidyl-L-lysyl-L-lysyl-L-leucyl-L-methionyl-Lphenylalanyl-L-lysyl-L-threonyl-L-α-glutamylglycyl-, [3aS-(3aα,4β,6aα)]-

187.

CAS Registry Number: 168022-85-3

MW - C74 H123 N21 O28 S

Name -L-Threonine, N-[5-(hexahydro-2-oxo-1Hthieno[3,4-d]imidazol-4-yl)-1-oxopentyl]-L-serylglycyl-L-serylglycyl-L-threonyl-L-glutaminyl-L-isoleucyl-L-α-aspartyl-L-seryl-L-prolyl-L-leucyl-L-asparaginylglycyl-L-lysyl-L-valyl-, [3aS-(3aα,4β,6aα)]-

188.

CAS Registry Number: 168022-84-2

MW - C82 H129 N25 O27 S

Name -L-Lysine, N-[5-(hexahydro-2-oxo-1H-thieno[3,4-d]imidazol-4-yl)-1-oxopentyl]-L-serylglycyl-L-serylglycyl-L-tryptophyl-L-arginyl-L-threonyl-L-glutaminyl-L-isoleucyl-L-α-aspartyl-L-seryl-L-prolyl-L-leucyl-L-asparaginylglycyl-, [3aS-(3aα,4β,6aα)]-

189.

CAS Registry Number: 155743-48-9

MW - C71 H91 N15 O22 S2

Name -L-Tyrosine, N-[N-[N-[N-[N-[N-[N-[N-[N-[N2-[N-[5-(hexahydro-2-oxo-1H-thieno[3,4-d]imidazol-4-yl)-1-oxopentyl]-L-seryl]-L-glutaminyl]-Ltyrosyl]glycyl]-L-tyrosyl]-L-cysteinyl]glycyl]-Lphenylalanyl]glycyl]-L-alanyl]-L-α-glutamyl]-,[3aS-(3aα,4β,6aα)]-

190.

CAS Registry Number: 155743-38-7

Name -L-Cysteine, N-[N2-[N-[N-[1-[N-[N-[N-[N2-[N-[5-(hexahydro-2-oxo-1H-thieno[3,4-d]imidazol-4-yl)-1-oxopentyl]-L-threonyl]-L-glutaminyl]-Lhistidyl]glycyl]-L-seryl]-L-prolyl]-L-tyrosyl]glycyl]-L-arginyl]-, [3aS-(3aα,4β,6aα)]-

191.

CAS Registry Number: 146877-07-8

MW - C148 H222 I N43 O42 S3

Name -Somatostatin-28 (sheep), N-[5-(hexahydro-2-oxo-1H-thieno[3,4-d]imidazol-4-yl)-1-oxopentyl]-8-L-leucine-22-D-tryptophan-25-[2-(iodo-125I)-L-tyrosine]-,[3aS-(3aα,4β,6aα)]-

192.

CAS Registry Number: 144120-00-3

MW - C95 H125 F3 I N25 O21 S

Name -α1-13-Corticotropin, 1-[N-[5-(hexahydro-2-oxo-1H-thieno[3,4-d]imidazol-4-yl)-1-oxopentyl]-Lserine]-2-[3-(iodo-125I)-L-tyrosine]-4-Lnorleucine-7-D-phenylalanine-11-[N6-[4-[3-(trifluoromethyl)-3H-diazirin-3-yl]benzoyl]-Llysine]-13-L-valinamide-, [3aS-(3aα,4β,6aα)]-

193.

CAS Registry Number: 144119-98-2

MW - C95 H126 F3 N25 O21 S

Name -α1-13-Corticotropin, 1-[N-[5-(hexahydro-2-oxo-1H-thieno[3,4-d]imidazol-4-yl)-1-oxopentyl]-Lserine]-4-L-norleucine-7-D-phenylalanine-11-[N6-[4-[3-(trifluoromethyl)-3H-diazirin-3-yl]benzoyl]-L-lysine]-13-L-valinamide-, [3aS-(3aα,4β,6aα)]-

194.

CAS Registry Number: 143519-58-8

MW - C148 H223 N43 O42 S3

Name -Somatostatin-28 (sheep), N-[5-(hexahydro-2-oxo-1H-thieno[3,4-d]imidazol-4-yl)-1-oxopentyl]-8-L-leucine-22-D-tryptophan-25-L-tyrosine-,[3aS-(3aα,4β,6aα)]-

195.

CAS Registry Number: 91295-35-1

MW - C86 H123 N23 O20 S

Name -α1-13-Corticotropin, N-[5-(hexahydro-2-oxo-1Hthieno[3,4-d]imidazol-4-yl)-1-oxopentyl]-4-Lnorleucine-7-D-phenylalanine-13-L-valinamide-,[3aS-(3aα,4β,6aα)]-

POLYMERS, PHARMACEUTICAL COMPOSITIONS AND METHODS OF SYNTHESIZING THE SAME

CROSS REFERENCE TO RELATED APPLICATIONS

This application claims priority under 35 USC § 119(e) from U.S. Provisional Application Ser. No. 61/980,255, filed Apr. 16, 2014, which application is herein specifically incorporated by reference in its entirety.

GOVERNMENTAL SUPPORT

The research leading to the present invention was supported, at least in part, by National Science Foundation Awards CHE-1152317 and IOS-1126971 and National Institutes of Health Award 32877-21/22. Accordingly, the Government has certain rights in the invention.

FIELD OF THE INVENTION

This invention relates to novel polymers to which polyethylene glycol has been attached (PEGylated polymers). The invention also relates to novel methods for the preparation of the PEGylated polymers. This invention further relates to novel oxazolidine compounds and use thereof in the preparation of the PEGylated polymers. This invention further relates to novel polymers to which AG moiety has been attached, and the AG is an active group, or a functional group as defined herein.

BACKGROUND OF THE INVENTION

PEG is a water-soluble, amphiphilic compound characterized by low immunogenicity, low antigenicity and low toxicity (J. M. Harris et al, In *Poly(ethylene glycol) chemistry and biological applications*, 1$^{st}$ edition, San Francisco, ACS, 1997; J. S. Kang et al, *Expert Opin Emerg Drugs*, 2009, 14, 363-380). PEGylation, the covalent attachment of PEG chains to proteins, has been used to advantage to improve the stability and pharmacokinetics of numerous biological therapeutics (Y. J. Wang, et al, *J. Controlled Release*, 2010, 145, 306-313; D. E. Borchmann, et al, *Rapid Commun.*, 2014, 35, 27-43). In general, PEGylated molecules exhibit enhanced solubility and stability in vitro and in vivo and improved safety profiles relative to their unPEGylated counterparts. Further to the above, PEGylation has been shown to impart numerous clinical benefits to PEGylated molecules, including increased efficacy, decreased side effects, and lower frequency of dosing (J. Kling *BioProcess International* 2013, 11, 35-43). Since the U.S. Food and Drug Administration's (FDA's) first approval of a PEGylated product (ADAGEN®; pegademase bovine) in 1990, a dozen PEGylated products have been approved and many more are in development. The worldwide market for PEGylated proteins was estimated to be about $7 billion in 2012 and sales of PEGylated protein therapeutics are projected to outpace the biopharmaceutical market in years to come (J. Kling *BioProcess International* 2013, 11, 35-43).

Despite the clear advantages of PEGylated proteins, the PEGylation process is complicated and often results in low yields. The process also suffers from difficulties associated with the variable nature of PEG conjugations, both with regard to location and number on a protein. Such variability can in turn lead to deleterious alterations at binding sites or active sites on a PEGylated protein that can reduce biological activity thereof. Reaction mixtures also typically comprise various undesirable species, including PEGylated isoforms (positional isoforms), excessively PEGylated proteins, native (unPEGylated) proteins, and unreacted PEGs. Purification of the desired species of PEGylated proteins is thus complicated by variabilities in the PEGylation process. In light of the above, the PEGylation reaction has to be approached in a very protein/product specific fashion, which impairs development of generalized processes for both the reaction and purification of PEGylated proteins (Yoshimoto et al, *Biotechnol. J.*, 2012, 7, 592-593; Fee et al, In Janson (Ed.), *Protein Purification* (3$^{rd}$ edition), John Wiley & Sons, Inc., Hoboken, 2011, 339-362).

In an effort to address some of the aforementioned challenges, methods are being developed to explore extrinsic and intrinsic chemical reactivity for site-selective bioconjugation (A. Dumas, et al, *Angew. Chem. Int. Ed.*, 2013, 52, 3916-3921; N. Li, et al, *J. Am. Chem. Soc.*, 2011, 133, 15316-15319; Z. Zhou, et al, *Bioconj. Chem.*, 2014, 25, 138-146; M. Wendeler, et al, *Bioconj. Chem.*, 2014, 25, 93-101; A. C. Obermeyer, et al, *Angew. Chem. Int. Ed.*, 2014, 53, 1057-1061; Y.-M. Li, et al, *Angew. Chem. Int. Ed.*, 2014, 126, 2230-2234; N. Toda, et al, *Angew. Chem. Int. Ed.*, 2013, 52, 12592-12596; M. Marsac, et al, *Bioconj. Chem.*, 2006, 17, 1492-1498). Particulars pertaining to extrinsic bioconjugation and intrinsic bioconjugation, which are one-step and two-step processes, respectively, are discussed in detail herein below. In short, although advances have been made using these approaches, neither approach appears well suited to the development of generalized processes for the efficient PEGylation of proteins.

Thus, there remains a need to develop new protocols that enable site-specific PEGylation of peptides and proteins.

SUMMARY OF THE INVENTION

As described in detail herein below, the present inventors have developed a new method for the site-specific introduction of PEG (polyethylene glycol) chains or AG moieties onto proteins. "AG" is a moiety as described herein.

In one aspect, the present invention presents processes for preparing novel polymers. Specifically, the present invention presents processes for preparing novel polymers according to formula I:

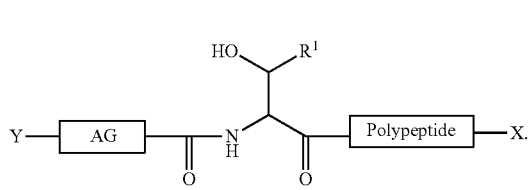

wherein
AG is
a) a moiety comprising polyethylene glycol; or AG is -(L$^1$-O)$_m$-LINK-; LINK is an alkylene linker; the subscript m is an integer from 2-200; L$^1$ is substituted or unsubstituted alkylene; and Y is hydroxy, protected hydroxyl, amino or protected amino; or Y is —O—R$^2$, —O—C(O)—R$^2$, —NH—C(O)—R$^2$ or —NH—C(O)—O—R$^2$;
b) a biotin moiety; and Y is absent;
c) a folate moiety; and Y is absent;
d) a fluorescein moiety; and Y is absent;

e) a lipid moiety; and Y is absent;
f) a carbohydrate moiety; and Y is absent;
g) a doxorubicin moiety; and Y is absent;
h) a small molecule therapeutic moiety, wherein the small molecule therapeutic moiety comprises at least one carboxylic group; and Y is absent;
i) a naproxen moiety; and Y is absent;
j) an ibuprofen moiety; and Y is absent;
k) a small molecule hormone moiety, wherein the small molecule hormone moiety comprises of at least one carboxylic group; and Y is absent;
l) a thyroxine moiety; and Y is absent; or
m) a small molecule imaging agent moiety, wherein the small molecule imaging agent comprises at least one carboxylic group; and Y is absent;

X is hydroxyl, alkoxy, amino or substituted amino;
$R^1$ is H or methyl;
each $R^2$ is independently H, alkyl, or aryl.

In one embodiment, the process comprises the steps of:
A1) providing a compound of formula II:

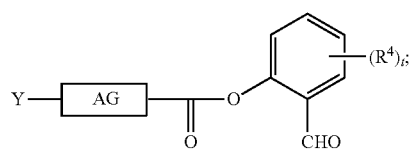

A2) reacting the compound of formula II with a polypeptide of formula III:

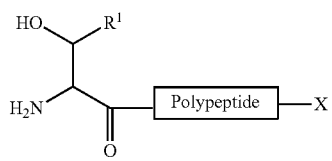

to form the oxazolidine compound of formula IV:

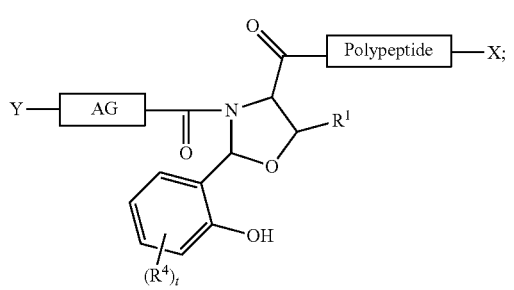

and A3) reacting the oxazolidine compound of formula IV with an acid to form the polymer of formula I.

In another aspect, the present invention presents processes for preparing polymers according to formula V:

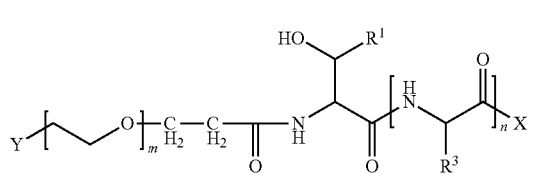

or a pharmaceutically acceptable salt, stereoisomer, isotopic variant or tautomer thereof;
comprising the steps of
B1) providing a compound of formula VI:

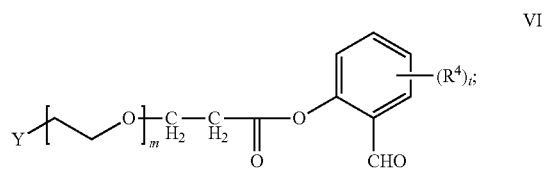

B2) reacting the compound of formula VI with a polypeptide of formula VII

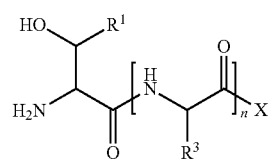

to form the oxazolidine compound of formula VIII:

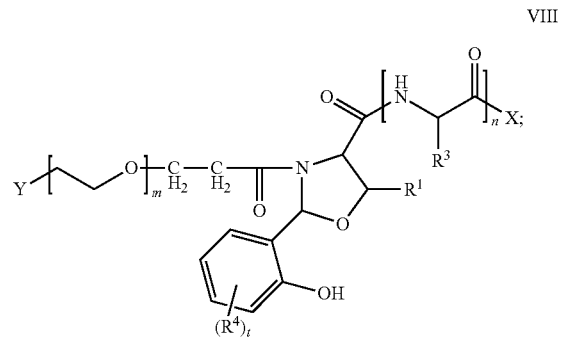

and
B3) reacting the oxazolidine compound of formula VIII with an acid to form the polymer of formula V;
wherein
X, Y, $R^1$, $R^2$, $R^3$, $R^4$, and t are as described for formula I, and
the subscript m is an integer from 2-200; the subscript n is an integer from 2-1000.

In yet another aspect, the present invention provides, oxazolidine compounds according to formula IV or VIII:

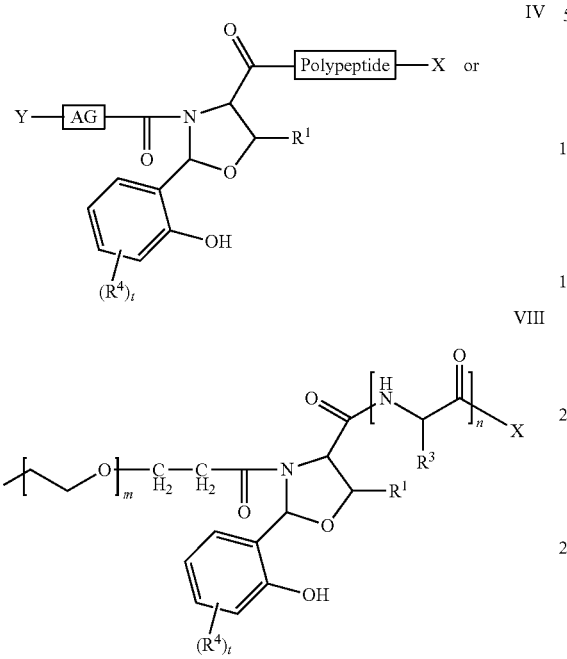

or a stereoisomer, a tautomer, or an isotopic variant thereof;
wherein
AG, Polypeptide, X, Y, $R^1$, $R^2$, $R^3$, $R^4$, and t are as described for formula I, and
the subscript m is an integer from 2-200; the subscript n is an integer from 2-1000.

In another aspect, the present invention provides, polymers or compounds according to formula I:

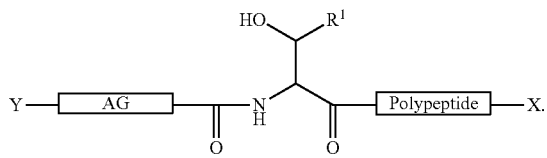

wherein
AG is
a) a moiety comprising polyethylene glycol; or AG is -($L^1$-O)$_m$-LINK-; LINK is an alkylene linker; the subscript m is an integer from 2-200; $L^1$ is substituted or unsubstituted alkylene; and Y is hydroxy, protected hydroxyl, amino or protected amino; or Y is —O—$R^2$, —O—C(O)—$R^2$, —NH—C(O)—$R^2$ or —NH—C(O)—O—$R^2$;
b) a biotin moiety; and Y is absent;
c) a folate moiety; and Y is absent;
d) a fluorescein moiety; and Y is absent;
e) a lipid moiety; and Y is absent;
f) a carbohydrate moiety; and Y is absent;
g) a doxorubicin moiety; and Y is absent;
h) a small molecule therapeutic moiety, wherein the small molecule therapeutic moiety comprises at least one carboxylic group; and Y is absent;
i) a naproxen moiety; and Y is absent;
j) an ibuprofen moiety; and Y is absent;
k) a small molecule hormone moiety, wherein the small molecule hormone comprises at least one carboxylic group; and Y is absent;
l) a thyroxine moiety; and Y is absent; or
m) a small molecule imaging agent moiety, wherein the small molecule imaging agent comprises of at least one carboxylic group; and Y is absent;
X is hydroxyl, alkoxy, amino or substituted amino;
$R^1$ is H or methyl;
each $R^2$ is independently H, alkyl, or aryl; provided that the polymer or the compound is other than compounds listed in FIGS. 5-10.

In another aspect, the present invention provides, polymers or the compound according to formula V:

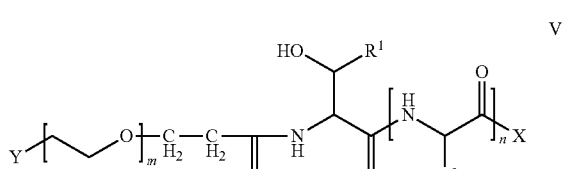

or a pharmaceutically acceptable salt, stereoisomer, isotopic variant or tautomer thereof;
wherein
X is hydroxyl, alkoxy, amino or substituted amino;
Y is hydroxy, protected hydroxyl, amino or protected amino; or Y is —O—$R^2$, —O—C(O)—$R^2$, —NH—C(O)—$R^2$ or —NH—C(O)—O—$R^2$;
$R^1$ is H or methyl;
each $R^2$ is independently H, alkyl, or aryl;
each $R^3$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
the subscript m is an integer from 2-200; and the subscript n is an integer from 2-1000; provided that polymer or the compound is other than compounds listed in FIG. 5.

In additional aspects, methods for synthesizing the oligomers of the invention are presented herein, with representative synthetic protocols and pathways thereof disclosed herein below.

Other objects and advantages will become apparent to those skilled in the art from a consideration of the ensuing detailed description, which proceeds with reference to the following illustrative drawings.

BRIEF DESCRIPTION OF THE DRAWINGS

FIG. 5 lists "Excluded Compounds 1-25".

FIG. 6 lists additional excluded compounds.

FIG. 7 lists additional excluded compounds.

FIG. 8 lists additional excluded compounds.

FIG. 9 lists additional excluded compounds.

FIG. 10 lists additional excluded compounds.

DETAILED DESCRIPTION OF THE INVENTION

Definitions

Figure 1:
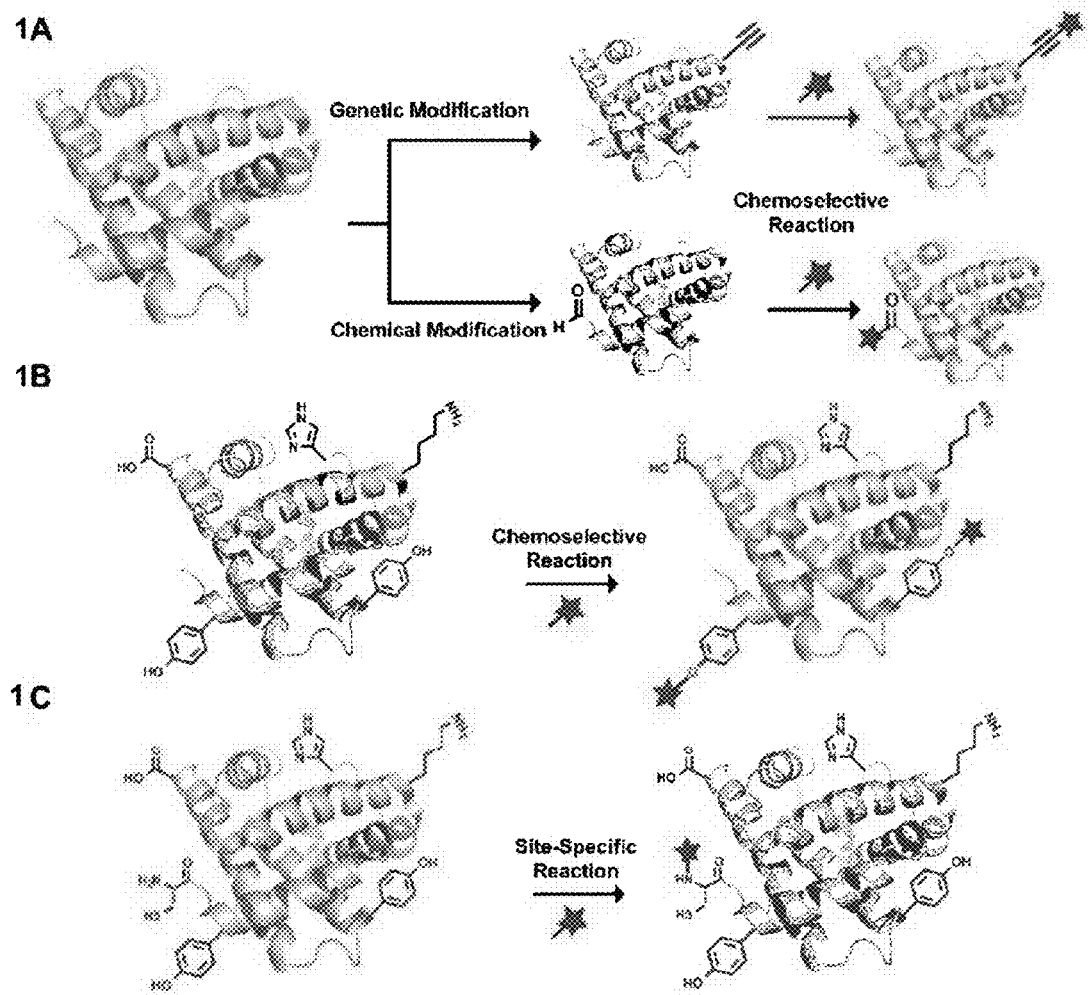
FIG. 1A-C shows Extrinsic (A) and intrinsic (B and C) bioconjugation strategies. Red star represents molecule of interest to be conjugated to protein architecture.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Oligomer' refers to a unit comprising a linear chain of two or more linked monomers. More specifically, an 'oligomer' of the invention is between 2-100 monomers, more particularly between 2-50 or 2-20.

'Acyl' or 'Alkanoyl' refers to a radical —C(O)R$^{20}$, where R$^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t$($C_6$-$C_{10}$ aryl), —C(O)—$(CH_2)_t$(5-10 membered heteroaryl), —C(O)—$(CH_2)_t$($C_3$-$C_{10}$ cycloalkyl), and —C(O)—$(CH_2)_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently
 $C_1$-$C_8$ alkyl, substituted with halo or hydroxy; or
 $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —OR$^{29}$ where R$^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkyl, thioaryloxy, thiol, alkyl-S(O)—, aryl-S(O)—, alkyl-S(O)$_2$— and aryl-S(O)$_2$—. Exemplary 'substituted alkoxy' groups are —O—$(CH_2)_t$($C_6$-$C_{10}$ aryl), —O—$(CH_2)_t$(5-10 membered heteroaryl), —O—$(CH_2)_t$($C_3$-$C_{10}$ cycloalkyl), and —O—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are $OCF_3$, $OCH_2CF_3$, $OCH_2Ph$, $OCH_2$-cyclopropyl, $OCH_2CH_2OH$, and $OCH_2CH_2NMe_2$.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl, n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and iso-amyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR'''-alkoxycarbonyl or —NH—C(O)—OR$^{27}$), amino, substituted amino, aminocarbonyl (carbamoyl or amido or —C(O)—NR''$_2$), aminocarbonylamino (—NR''—C(O)—NR''$_2$), aminocarbonyloxy (—O—C(O)—NR''$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R'', —SO$_2$NR''R''', —C(O)R'', —C(O)OR'', —OC(O)R'', —NR'''C(O)R'', —C(O)NR''R''', —NR''R''', or —(CR'''R'''')$_m$OR'''; wherein each R'' is independently selected from H, $C_1$-$C_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R''' and R'''' independently represents H or $C_1$-$C_8$ alkyl.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

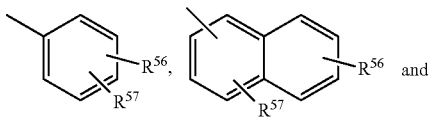

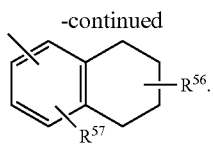

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocycloalkyl, alkanoyl, $C_1$-$C_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or $R^{56}$ and $R^{57}$ may be joined to form a cyclic ring (saturated or unsaturated) from 5 to 8 atoms, optionally containing one or more heteroatoms selected from the group N, O or S. $R^{60}$ and $R^{61}$ are independently hydrogen, C1-C8 alkyl, C1-C4 haloalkyl, C3-C10 cycloalkyl, 4-10 membered heterocycloalkyl, C6-C10 aryl, substituted aryl, 5-10 membered heteroaryl.

'Heteroaryl' means an aromatic ring structure, monocyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

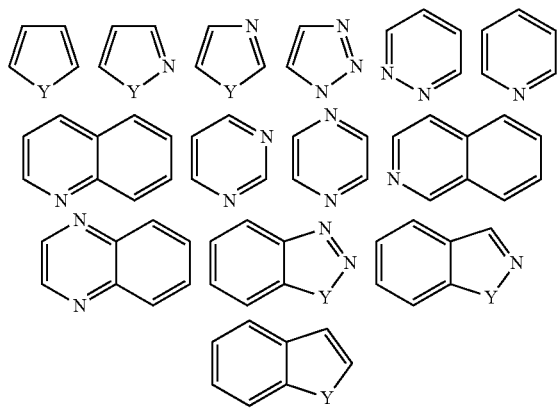

wherein each Y is selected from carbonyl, N, $NR^{65}$, O and S; and $R^{65}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative aryl having hetero atoms containing substitution include the following:

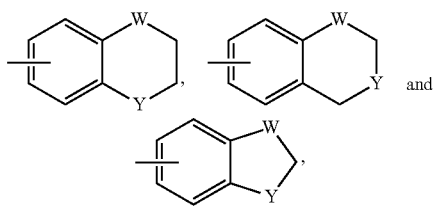

wherein each W is selected from $C(R^{66})_2$, $NR^{66}$, O and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

"Unnatural amino acids" means amino acids and corresponding peptoid oligomers that are synthesized from single amino acid starting materials. Such unnatural amino acids may be prepared and used individually in accordance with the present invention, or may incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, *Science*, 244: 182-188 (April 1989). "Natural amino acids" refers to the standard 20 amino acids which are known to those of skill in the art.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "patient" and "subject" are used interchangeably herein. Accordingly, a subject can be a mammal, in a particular embodiment a human, or a bird, a reptile, an amphibian, or a plant.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2H$ or D), carbon-13 ($^{13}C$), nitrogen-15 ($^{15}N$), or the like. It will be understood that, in a compound comprising an unnatural proportion of an isotope, any example of an atom where present, may vary in isotope composition. For example, any hydrogen may be $^2H/D$, or any carbon may be $^{13}C$, or any nitrogen may be $^{15}N$, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The Novel Methods

The conjugation of poly(ethylene glycol) to proteins has become one of the most successful and widely utilized approaches to improve the stability and pharmacokinetics of biological therapeutics (Y. J. Wang, et al, *J. Controlled Release*, 2010, 145, 306-313; D. E. Borchmann, et al, *Rapid Commun.*, 2014, 35, 27-43). This 'PEGylation' increases the hydrodynamic volume of the product molecules, establishing reduced clearance rates and protection from proteolytic degradation by endogenous enzymes (G. Pasut et al, *Adv. Drug Delivery Rev.*, 2009, 61, 1177-1188). Implementation of typical chemical conjugation strategies can result in heterogeneous PEGylated proteins due to the presence of multiple sites of reactivity on the protein surface (S. N. S. Alconcel, et al, *Polym. Chem.*, 2011, 2, 1442-1448). This polydispersity can engender difficult separation and diminished biological activity for a significant fraction of the product species (C. J. Fee et al, *Chem. Eng. Sci.*, 2006, 61, 924-939). For example, PEGylated Interferon α-2a, a hepatitis C therapeutic, can consist of various positional isomers and retains only a fraction of its activity (7%) in comparison to the original protein (P. Bailin, et al, *Bioconj. Chem.*, 2001, 12, 195-202). In this study, the present inventors introduce a new method for the site-specific introduction of PEG chains onto proteins.

Ongoing studies are developing both extrinsic and intrinsic chemical reactivity for site-selective bioconjugation (A. Dumas, et al, *Angew. Chem. Int. Ed.*, 2013, 52, 3916-3921; N. Li, et al, *J. Am. Chem. Soc.*, 2011, 133, 15316-15319; Z. Zhou, et al, *Bioconj. Chem.*, 2014, 25, 138-146; M. Wendeler, et al, *Bioconj. Chem.*, 2014, 25, 93-101; A. C. Obermeyer, et al, *Angew. Chem. Int. Ed.*, 2014, 53, 1057-1061; Y.-M. Li, et al, *Angew. Chem. Int. Ed.*, 2014, 126, 2230-2234; N. Toda, et al, *Angew. Chem. Int. Ed.*, 2013, 52, 12592-12596; M. Marsac, et al, *Bioconj. Chem.*, 2006, 17, 1492-1498). Extrinsic bioconjugation is two-step process that requires genetic or chemical modification to incorporate a non-natural reactive moiety into the native protein target (FIG. 1A). In the first step, extrinsic chemical reactivity is established by introducing non-natural amino acids or by modifying the protein termini, such as oxidizing the N-terminus to an aldehyde. Extrinsic functionality can also be introduced into proteins via chemo-enzymatic protocols (M. Rashidian, et al, *J. Am. Chem. Soc.*, 2012, 134, 8455-8467). The second step then selectively conjugates the molecule of interest, such as PEG, to the protein target through a chemoselective process, such as a crosscoupling or 'click' reaction (N. Li, et al, *J. Am. Chem. Soc.*, 2011, 133, 15316-15319; Y.-M. Li, et al, *Angew. Chem. Int. Ed.*, 2014, 126, 2230-2234).

In contrast, intrinsic approaches use inherent reactivity to selectively label protein side-chains (FIG. 1B) (N. Toda, et al, *Angew. Chem. Int. Ed.*, 2013, 52, 12592-12596) or termini (FIG. 1C) (M. Marsac, et al, *Bioconj. Chem.*, 2006, 17, 1492-1498) in one-step. Although a number of promising intrinsic approaches have been reported, the challenge of selectivity still remains an issue (H. Ban, et al, *Bioconj. Chem.*, 2013, 24, 520-532; M. W. et al, *J. Am. Chem. Soc.*, 2012, 134, 7406-7413). For example, PEGylation of Chymotrypsinogen A using the 'tyrosine click' reaction yields two PEGylated products due to two tyrosine residues located on the external surface of the protein (H. Ban, et al, *Bioconj. Chem.*, 2013, 24, 520-532). For this reason, new protocols that enable site-specific PEGylation using intrinsic functionality are needed.

Thus, in one aspect, the present invention provides, processes for preparing novel polymers. Specifically, the present invention presents processes for preparing novel polymers according to formula I:

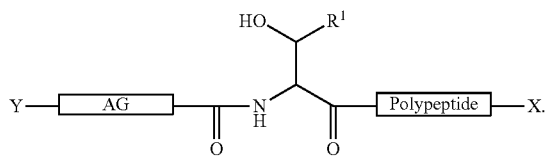

I wherein

AG is a) a moiety comprising polyethylene glycol; or AG is -(L$^1$-O)$_m$-LINK-; LINK is an alkylene linker; the subscript m is an integer from 2-200; L$^1$ is substituted or unsubstituted alkylene; and Y is hydroxy, protected hydroxyl, amino or protected amino; or Y is —O—R$^2$, —O—C(O)—R$^2$, —NH—C(O)—R$^2$ or —NH—C(O)—O—R$^2$;

b) a biotin moiety; and Y is absent;

c) a folate moiety; and Y is absent;

d) a fluorescein moiety; and Y is absent;

e) a lipid moiety; and Y is absent;

f) a carbohydrate moiety; and Y is absent;

g) a doxorubicin moiety; and Y is absent;

h) a small molecule therapeutic moiety, wherein the small molecule therapeutic moiety comprises at least one carboxylic group; and Y is absent;

i) a naproxen moiety; and Y is absent;

j) an ibuprofen moiety; and Y is absent;

k) a small molecule hormone moiety, wherein the small molecule hormone moiety comprises at least one carboxylic group; and Y is absent;

l) a thyroxine moiety; and Y is absent; or m) a small molecule imaging agent moiety, wherein the small molecule imaging agent moiety comprises at least one carboxylic group; and Y is absent;

X is hydroxyl, alkoxy, amino or substituted amino;

R$^1$ is H or methyl;

each R$^2$ is independently H, alkyl, or aryl.

In one embodiment, when the AG moiety is a polyethylene glycol comprising moiety, the polymer is PEGylated polymer.

In another embodiment, PEGylated polymer is a polymer wherein the AG moiety comprises polyethylene glycol.

In one embodiment, the polypeptide segment comprises a protein, and in a more particular embodiment thereof, the protein comprises at least one serine or threonine residue at its N-terminus. The protein may comprise at least one serine or threonine residue at its N-terminus or may be engineered to comprise same using methods known in the art.

In one embodiment, the polypeptide segment is a long peptide chain. In another embodiment, the polypeptide segment comprises more than 100 amino acids.

In one embodiment, the polypeptide segment is a protein. In another embodiment, the polypeptide segment comprises between 50-100 amino acids.

Exemplary proteins that may be conjugated using methods described herein include, without limitation, adenosine deaminase, interferon alpha, interferon beta 2B, tumor necrosis factor alpha (TNFα), adrenocorticotrophic hormone (ACTH) and analogs thereof, corticorelins, afamelanotide, thymalfasin, granulocyte colony-stimulating factor (Neupogen, for example, which has an added N-terminal methionine), immunoglobulins, alpha galactosidase, hexoaminidase A, and urate oxidase.

In one embodiment, the polypeptide segment is a short peptide chain. In another embodiment, the polypeptide segment comprises fewer than 50 amino acids.

In one embodiment, the process comprises the steps of:

A1) providing a compound of formula II:

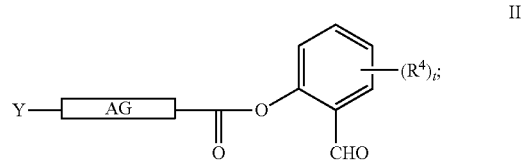

II

A2) reacting the compound of formula II with a polypeptide of formula III:

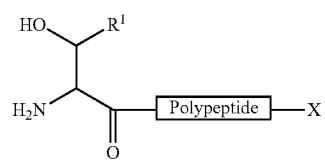

III to form the oxazolidine compound of formula IV:

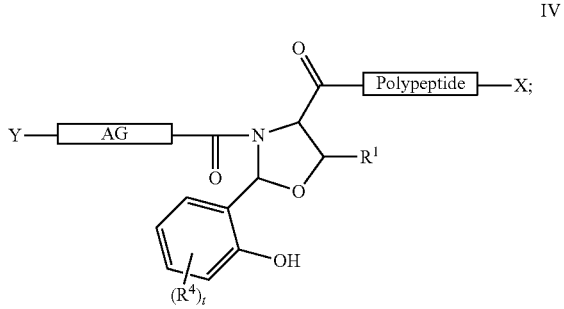

IV and

A3) reacting the oxazolidine compound of formula IV with an acid to form the polymer of formula I.

In another aspect, the present invention provides, novel polymers or compounds according to formula I:

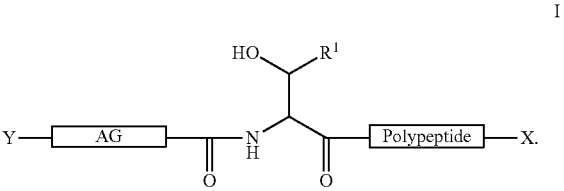

I wherein

AG is a) a moiety comprising polyethylene glycol; or AG is -(L$^1$-O)$_m$-LINK-; LINK is an alkylene linker; the subscript m is an integer from 2-200; L$^1$ is substituted or unsubstituted alkylene; and Y is hydroxy, protected hydroxyl, amino or protected amino; or Y is —O—R$^2$, —O—C(O)—R$^2$, —NH—C(O)—R$^2$ or —NH—C(O)—O—R$^2$;

b) a biotin moiety; and Y is absent;

c) a folate moiety; and Y is absent;

d) a fluorescein moiety; and Y is absent;

e) a lipid moiety; and Y is absent;

f) a carbohydrate moiety; and Y is absent;

g) a doxorubicin moiety; and Y is absent;

h) a small molecule therapeutic moiety, wherein the small molecule therapeutic moiety comprises at least one carboxylic group; and Y is absent;

i) a naproxen moiety; and Y is absent;

j) an ibuprofen moiety; and Y is absent;

k) a small molecule hormone moiety, wherein the small molecule hormone moiety comprises at least one carboxylic group; and Y is absent;

l) a thyroxine moiety; and Y is absent; or m) a small molecule imaging agent moiety, wherein the small molecule imaging agent moiety comprises at least one carboxylic group; and Y is absent;

X is hydroxyl, alkoxy, amino or substituted amino;

$R^1$ is H or methyl;

each $R^2$ is independently H, alkyl, or aryl.

In one embodiment, AG further comprises any polyethylene glycol moiety. In one embodiment, the polyethylene glycol moiety comprises a linear, branched, forked, or a releasable polyethylene glycol moiety. In a particular embodiment, the polyethylene glycol moiety comprises a linear polyethylene glycol moiety. In one embodiment AG is PEG, and PEG is a moiety comprising polyethylene glycol; and the polymer is PEGylated polymer.

In one embodiment, AG comprises a terminal group LINK.

In another embodiment, AG is -$(L^1-O)_m$-LINK-.

In one embodiment, LINK is substituted or unsubstituted alkylene or heteroalkylene.

In another embodiment, LINK is $C_2$-$C_{20}$ alkylene.

In another embodiment, LINK is $C_2$-$C_6$ alkylene.

In one particular embodiment, LINK is ethylene, propylene, or butylene.

In a more particular embodiment, LINK is ethylene or —$CH_2$—$CH_2$—.

In one embodiment, $L^1$ is substituted or unsubstituted alkylene. In another embodiment, L1 is substituted or unsubstituted ethylene. In another embodiment, L1 is unsubstituted ethylene.

In one particular embodiment, $L^1$ is —$CH_2$—$CH_2$—.

In another aspect, the present invention provides processes for preparing PEGylated polymers according to formula V:

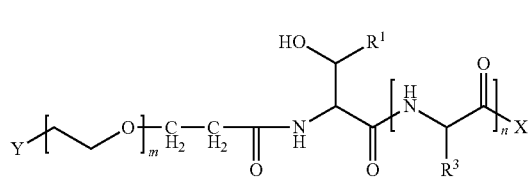

or a pharmaceutically acceptable salt, stereoisomer, isotopic variant or tautomer thereof;

comprising the steps of

B1) providing a compound of formula VI:

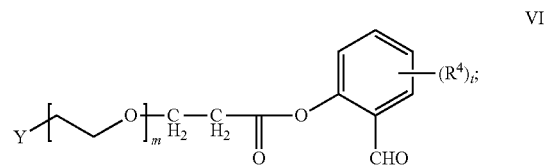

B2) reacting the compound of formula VI with a polypeptide of formula VII

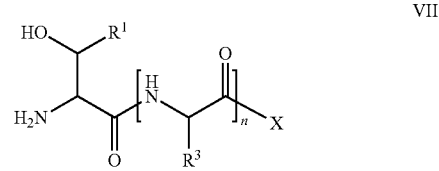

to form the oxazolidine compound of formula VIII:

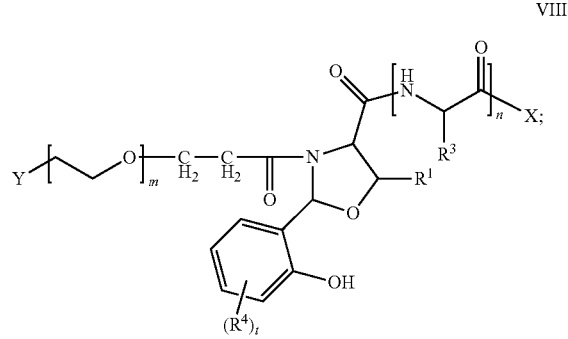

and

B3) reacting the oxazolidine compound of formula VIII with an acid to form the PEGylated polymer of formula V;

wherein

X, Y, $R^1$, $R^2$, $R^3$, $R^4$, and t are as described herein, and the subscript m is an integer from 2-200; the subscript n is an integer from 2-1000.

In one embodiment, the compound of formula II or formula VI is prepared by reacting the compound of formula IX or formula X, respectively, with the salicylaldehyde derivative of formula XI:

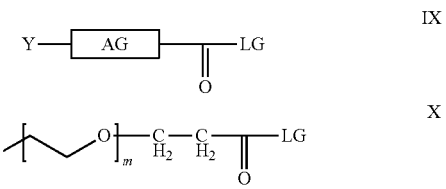

XI

[Structure: salicylaldehyde derivative with HO on benzene ring, CHO substituent, and (R⁴)ₜ]

wherein AG, Y, and m are as described herein; and LG is OH, or a leaving group.

In one embodiment, the compound of formula II is prepared by reacting the compound of formula IX with the salicylaldehyde derivative of formula XI. In another embodiment, the compound of formula VI is prepared by reacting the compound of formula X with the salicylaldehyde derivative of formula XI.

In one embodiment, LG is any conventional leaving group known to one skilled in the art.

In one embodiment, LG is OH. In another embodiment, LG is halogen. In a particular embodiment, LG is Cl.

In one embodiment, the reaction occurs in the presence of a solvent.

In another embodiment, the reaction occurs in the presence of methylene chloride, ethylene chloride, or tetrachloroethane.

In one embodiment, the reaction occurs in the presence of methylene chloride.

In another embodiment, the reaction occurs in the presence of diisopropylcarbodiimide.

In another embodiment, the reaction occurs in the presence of diisopropylcarbodiimide (DIC); and the DIC is about 1.2 equivalent of IX or X.

In another embodiment, the reaction occurs in the presence of a catalyst.

In another embodiment, the reaction occurs in the presence of a catalytic amount of dimethylaminopyridine (DMAP).

In another embodiment, the reaction occurs at around 20-30° C.

In another embodiment, the reaction occurs for 4-24 hrs.

In one embodiment, the step A2 or B2 occurs in the presence of a solvent.

In another embodiment, the step A2 or B2 occurs in the presence of a solvent; and the solvent is pyridine.

In another embodiment, the step A2 or B2 occurs in the presence of an acid.

In another embodiment, the step A2 or B2 occurs in the presence of acetic acid.

In another embodiment, the step A2 or B2 occurs in the presence of 10:1, 4:1, 3:1, 2:1, 1:1, 1:2, 1:3, 1:4, 1:5, or 1:10 mole/mole pyridine and acetic acid. In another embodiment, the step A2 or B2 occurs in the presence of 1:1 mole/mole pyridine and acetic acid.

In another embodiment, the step A2 or B2 occurs at around 20-30° C.

In another embodiment, the step A3 or B3 occurs in the presence of solvent.

In another embodiment, the step A3 or B3 occurs in the presence of an acid.

In another embodiment, the step A3 or B3 occurs in the presence of trifluoroacetic acid (TFA).

In another embodiment, the step A3 or B3 occurs in the presence of i-Pr₃SiH.

In another embodiment, the step A3 or B3 occurs in the presence of water.

In another embodiment, the step A3 or B3 occurs in the presence of TFA, water and i-Pr₃SiH (94/5/1, v/v/v).

In another embodiment, the step A3 or B3 occurs for 0.1 to 2 hrs.

In another aspect, the present invention provides, PEGylated polymers or compounds according to formula V:

V

[Structure: PEGylated polymer of formula V showing Y-[O-CH₂-CH₂]ₘ-O-C(O)-NH-C(R¹)(CH₂OH)-C(O)-NH-CH(R³)-C(O)-X with subscript n]

or a pharmaceutically acceptable salt, stereoisomer, isotopic variant or tautomer thereof;

wherein

X is hydroxyl, alkoxy, amino or substituted amino;

Y is hydroxy, protected hydroxyl, amino or protected amino; or Y is —O—R², —O—C(O)—R², —NH—C(O)—R² or —NH—C(O)—O—R²;

R¹ is H or methyl;

each R² is independently H, alkyl, or aryl;

each R³ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;

the subscript m is an integer from 2-200; and the subscript n is an integer from 2-1000.

In one embodiment, with respect to the composition of the PEGylated polymers according to formula I or formula V, the polymer is other than "Excluded Compounds 1-25". The "Excluded Compounds 1-25" are given in FIG. 5.

In one embodiment, with respect to the composition of the PEGylated polymers according to formula I or formula V, Y is other than:

[Structures shown: H₂C=CH—CH₂— (CH₂=CH—CH₂—), —NH—C(O)—CH₂—NH—NH₂, and three additional complex structures including anthracenone derivatives with NH₂ groups and a pyrimidine-containing methoxy-substituted structure]

-continued

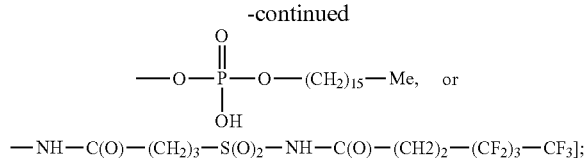

or X is other than:

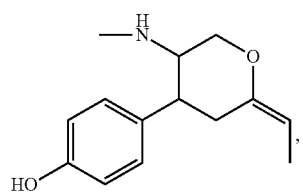

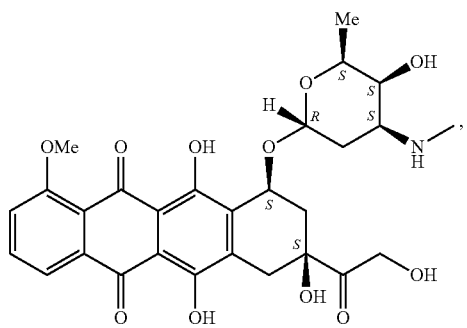

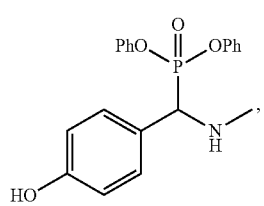

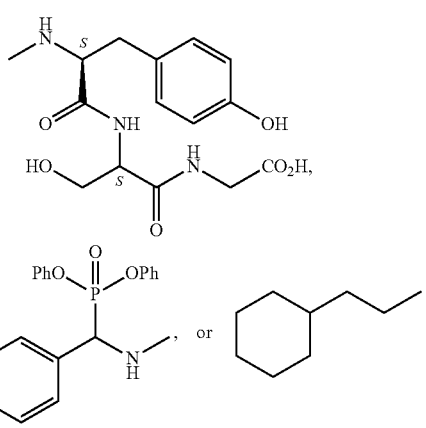

In yet another aspect, the present invention provides, oxazolidine compounds according to formula IV:

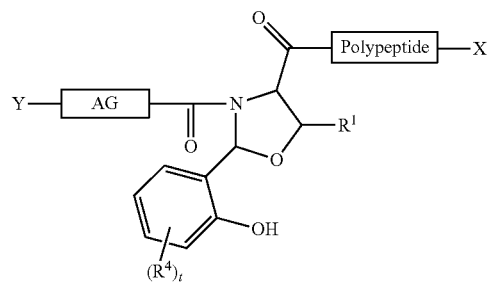

or a stereoisomer, a tautomer, or an isotopic variant thereof;
wherein
AG is
  a) a moiety comprising polyethylene glycol; or AG is -(L$^1$-O)$_m$-LINK-; LINK is an alkylene linker; the subscript m is an integer from 2-200; L$^1$ is substituted or unsubstituted alkylene; and Y is hydroxy, protected hydroxyl, amino or protected amino; or Y is —O—R$^2$, —O—C(O)—R$^2$, —NH—C(O)—R$^2$ or —NH—C(O)—O—R$^2$;
  b) a biotin moiety; and Y is absent;
  c) a folate moiety; and Y is absent;
  d) a fluorescein moiety; and Y is absent;
  e) a lipid moiety; and Y is absent;
  f) a carbohydrate moiety; and Y is absent;
  g) a doxorubicin moiety; and Y is absent;
  h) a small molecule therapeutic moiety, wherein the small molecule therapeutic moiety comprises at least one carboxylic group; and Y is absent;
  i) a naproxen moiety; and Y is absent;
  j) an ibuprofen moiety; and Y is absent;
  k) a small molecule hormone moiety, wherein the small molecule hormone moiety comprises at least one carboxylic group; and Y is absent;
  l) a thyroxine moiety; and Y is absent; or
  m) a small molecule imaging agent moiety, wherein the small molecule imaging agent moiety comprises at least one carboxylic group; and Y is absent;
X is hydroxyl, alkoxy, amino or substituted amino;
R$^1$ is H or methyl;
each R$^2$ is independently H, alkyl, or aryl;
each R$^4$ is independently H or substituted or unsubstituted alkyl;
and
the subscript t is 1, 2, 3, or 4.

In one embodiment, AG is PEG; and PEG is a polyethylene glycol moiety. In another embodiment, PEG further comprises any polyethylene glycol moiety. In one embodiment, the polyethylene glycol moiety comprises a linear, branched, forked, and/or a releasable polyethylene glycol moiety. In a particular embodiment, the polyethylene glycol moiety comprises a linear polyethylene glycol moiety.

In one embodiment, PEG comprises a terminal group LINK.

In another embodiment, PEG is -(L$^1$-O)$_m$-LINK-.

In one embodiment, LINK is substituted or unsubstituted alkylene or heteroalkylene.

In another embodiment, LINK is C$_2$-C$_{20}$ alkylene.

In another embodiment, LINK is C$_2$-C$_6$ alkylene.

In one particular embodiment, LINK is ethylene, propylene, or butylene.

In a more particular embodiment, LINK is ethylene or —CH$_2$—CH$_2$—.

In one embodiment, L$^1$ is substituted or unsubstituted alkylene. In another embodiment, L1 is substituted or unsubstituted ethylene. In another embodiment, L1 is unsubstituted ethylene.

In one particular embodiment, L$^1$ is —CH$_2$—CH$_2$—.

In yet another aspect, the present invention provides, oxazolidine compounds according to formula VIII:

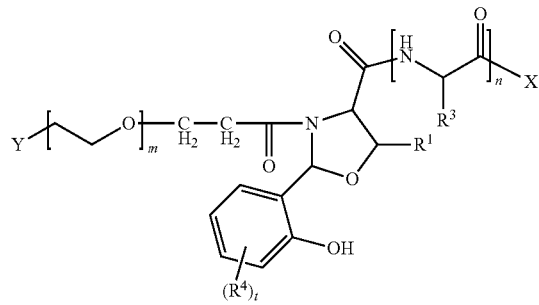

VIII or a stereoisomer, a tautomer, or an isotopic variant thereof;
wherein
X is hydroxyl, alkoxy, amino or substituted amino;
Y is hydroxy, protected hydroxyl, amino or protected amino; or Y is —O—R$^2$, —O—C(O)—R$^2$, —NH—C(O)—R$^2$ or —NH—C(O)—O—R$^2$;
R$^1$ is H or methyl;
each R$^2$ is independently H, alkyl, or aryl;
each R$^3$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
each R$^4$ is independently H or substituted or unsubstituted alkyl;
and
the subscript m is an integer from 2-200; the subscript n is an integer from 2-1000;
the subscript t is 1, 2, 3, or 4.

In one embodiment, with respect to the novel polymers, the polypeptide is a long peptide chain. In one embodiment, the polypeptide comprises more than 100 amino acid residues.

In one embodiment, the polypeptide is a protein. In another embodiment, the polypeptide comprises between 50-100 amino acid residues.

In one embodiment, the polypeptide is a short peptide chain. In another embodiment, the polypeptide comprises fewer than 50 amino acid residues.

In one embodiment, with respect to the novel polymers according to formula I or II, the amino acid residues are selected from one or more glycine, L-lysine, L-cysteine, L-aspartic acid, L-asparagine, L-glutamine, L-alanine, L-valine, L-leucine, L-iso-leucine, L-tyrosine, L-proline, L-serine, L-threonine, L-glutamic acid, L-tryptophan, L-phenylalanine, L-methionine, L-arginine, and L-histidine residues.

In one embodiment, Y is —O—R$^2$, or —O—C(O)—R$^2$.
In another embodiment, Y is —O—C(O)—R$^2$; and —C(O)—R$^2$ is acetyl, lauroyl, tridecanoyl, myristoyl, pentadecanoyl, palmitoyl, caproyl, benzoyl, cetyl, decyl, acetyl, phenyl acetyl, cyclohexyl acetyl, valeroyl, or glucuronyl residue.

In another embodiment, Y is —OCOCH$_3$.
In another embodiment, Y is —NH—C(O)—R$^2$ or —NH—C(O)—O—R$^2$.
In another embodiment, Y is NH—COCH$_3$.
In one particular embodiment, Y is NH-t-Boc. In another particular embodiment, Y is —NH$_2$.

In one embodiment, AG moiety is "AG" moiety of AG-C(O)—OH molecule. For example, biotin moiety is biotin without the COOH group:

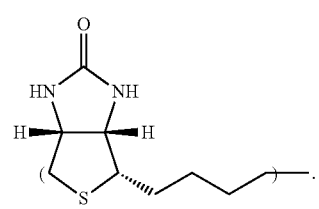

Thus, the biotin moiety is the group in the parenthesis.

Similarly, when AG is a "small molecule therapeutic" moiety; the small molecule therapeutic is any small molecule drug molecule containing a COOH group; and the "small molecule therapeutic" moiety is the small molecule drug molecule without the COOH group. For example, ibuprofen moiety is the group in the parenthesis:

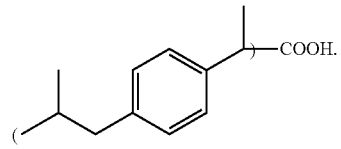

Similarly, naproxen moiety is the group in the parenthesis:

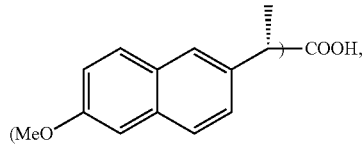

and so on.

In one embodiment, AG is a biotin moiety; the biotin moiety is:

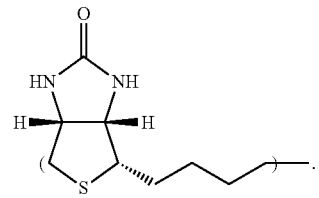

and Y is absent.

Figure 12:
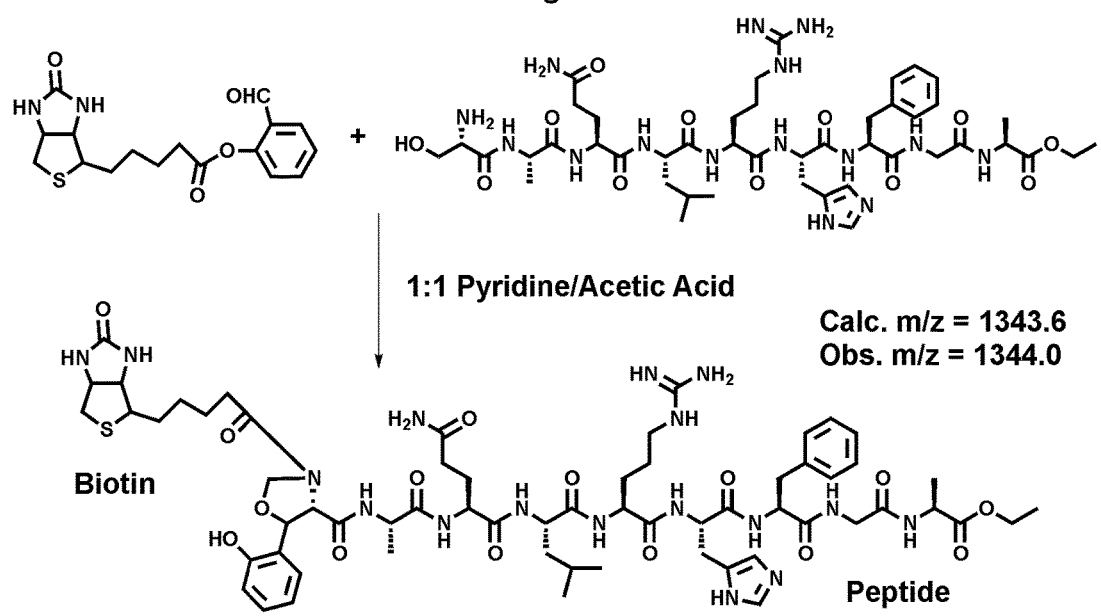
FIG. 12 depicts a reaction whereby a biotin salicylaldehyde ester is ligated to a peptide. Only the intermediate product, rather than the final product, is shown.
Figure 13:
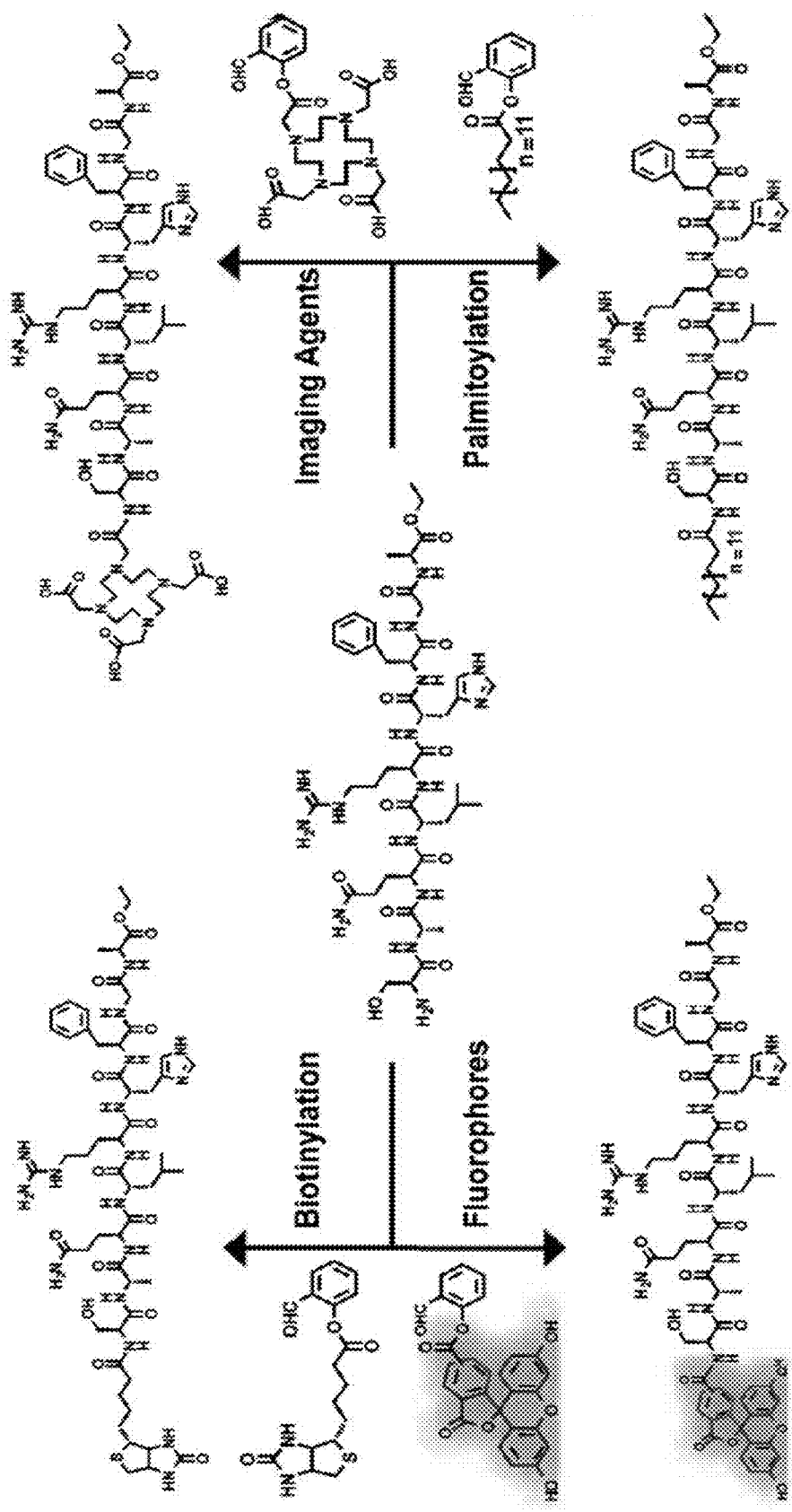
FIG. 13 depicts the structures of exemplary active groups (AGs) and ligated products comprising same.

FIG. 12 presents a chemical reaction whereby a biotin salicylaldehyde ester was ligated to a peptide. As indicated therein, the m/z of the ligated product is 1344.0, which is in close agreement with the predicted m/z of 1343.6. These results underscore that a variety of functional groups, such as biotin, and active groups can be ligated onto the N-termini of peptides/proteins using methods described herein.

In another embodiment, AG is a folate moiety; and Y is absent.

In another embodiment, AG is a folate moiety; the folate moiety is:

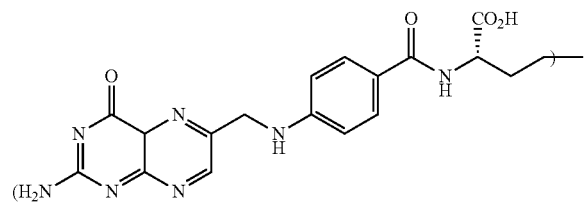

and Y is absent.

In another embodiment, the folate moiety is a PEGylated folate moiety.

In another embodiment, AG is a fluorescein moiety; and Y is absent.

In another embodiment, AG is a fluorescein moiety; the fluorescein molecule is any coumarin derivative; and Y is absent.

In another embodiment, AG is a fluorescein moiety; the fluorescein moiety is:

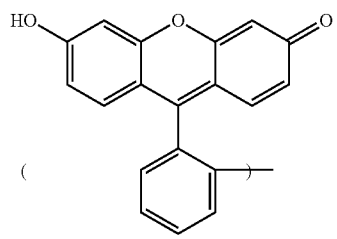

and Y is absent.

In another embodiment, AG is a lipid moiety (e.g., palmitic acid); and Y is absent.

In another embodiment, AG-C(O)— group is oleaoyl, stearoyl, or palmitoyl; and Y is absent.

In another embodiment, AG is a carbohydrate moiety; and Y is absent.

In another embodiment, AG is a carbohydrate moiety; the carbohydrate moiety is sialic acid moiety; and Y is absent.

In another embodiment, AG-C(O)— group is sialoyl; and Y is absent.

In another embodiment, AG is a doxorubicin moiety or doxorubicin-PEG moiety; and Y is absent.

In another embodiment, AG is a small molecule therapeutic moiety, wherein the small molecule therapeutic moiety comprises at least one carboxylic group; and Y is absent.

In another embodiment, AG is a naproxen moiety; and Y is absent.

In another embodiment, AG-C(O)— group is naproxenoyl; and Y is absent.

In another embodiment, AG is a naproxen moiety; the naproxen moiety is:

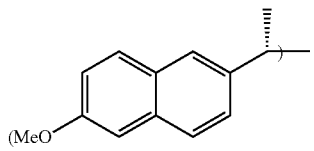

and Y is absent.

In another embodiment, AG is an ibuprofen moiety; and Y is absent.

In another embodiment, AG-C(O)— group is ibuprofenoyl; and Y is absent.

In another embodiment, AG is a ibuprofen moiety; the ibuprofen moiety is:

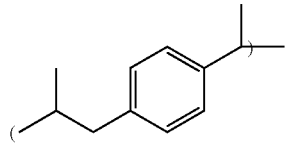

and Y is absent.

In another embodiment, AG is a small molecule hormone moiety, wherein the small molecule hormone moiety comprises at least one carboxylic group; and Y is absent.

In another embodiment, AG is a thyroxine moiety; and Y is absent.

In another embodiment, AG is a thyroxine moiety; the thyroxine moiety is:

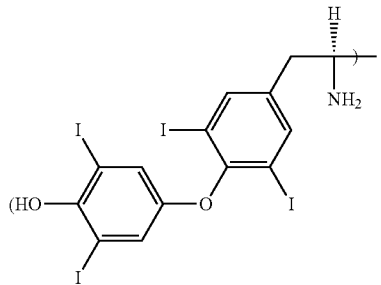

and Y is absent.

In another embodiment, AG is a small molecule imaging agent moiety, wherein the small molecule imaging agent moiety comprises at least one carboxylic group; and Y is absent.

In another embodiment, AG is a small molecule imaging agent moiety, wherein the small molecule imaging agent is DOTA imaging agent; and Y is absent.

In one embodiment, $R^1$ is H. In another embodiment, $R^1$ is Me.

In one embodiment, each of $R^3$ is independently Me, Et, n-Pr, i-Pr, n-Bu, sec-Bu, or i-Bu.

In one embodiment, each of $R^3$ is independently phenyl or benzyl, unsubstituted or substituted with one or more groups selected from alkyl, halo, hydroxy, amino, nitro, and alkoxy.

In another embodiment, each of $R^3$ is independently phenethyl, unsubstituted or substituted with one or more groups selected from alkyl, halo, hydroxy, amino, nitro, and alkoxy.

In another embodiment, each of $R^3$ is independently 2-naphthyl, unsubstituted or substituted with one or more groups selected from alkyl, halo, hydroxy, amino, nitro, and alkoxy.

In another embodiment, each of $R^3$ is independently 2,2-diphenylethyl, unsubstituted or substituted with one or more groups selected from alkyl, halo, hydroxy, amino, nitro, and alkoxy.

In another embodiment, each of $R^3$ is independently furanyl or thienyl, unsubstituted or substituted with one or more groups selected from alkyl, halo, hydroxy, amino, nitro, and alkoxy.

In another embodiment, each of $R^3$ is independently aminomethyl, 2-aminoethyl, 3-aminopropyl, 4-aminobutyl, 5-aminopentyl, or 6-aminohexyl.

In another embodiment, each of $R^3$ is independently 3-aminopropyl.

In another embodiment, each of $R^3$ is independently guanidinoalkyl.

In another embodiment, each of $R^3$ is independently guanidinomethyl, 2-guanidinoethyl, 3-guanidinopropyl, 4-guanidinobutyl, 5-guanidinopentyl, or 6-guanidinohexyl.

In another embodiment, each of $R^3$ is independently 4-guanidinobutyl.

In another embodiment, each of $R^3$ is independently imidazolylmethyl, 2-imidazolylethyl, 3-imidazolylpropyl, 4-imidazolylbutyl, 5-imidazolylpentyl, or 6-imidazolylhexyl.

In another embodiment, each of $R^3$ is independently methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In another embodiment, each of $R^3$ is selected from a group consisting of any of the $R^3$ groups described above.

In one particular embodiment, each of $R^3$ is independently Me, i-Pr, i-Bu, sec-Bu, phenethyl, 4-hydroxyphenethyl, benzimidazol-3-ylmethyl, thiomethyl, methylthioethyl, hydroxymethyl, aminopropyl, guanadinopropyl, or imdazo-4-yl methyl.

In one embodiment, t is 4; and each of $R^4$ is H; or t is 1 or 2, and each of $R^4$ is independently Me, Et, i-Pr or $CF_3$.

In one embodiment, the polypeptide, when present, is a protein.

Figure 4:
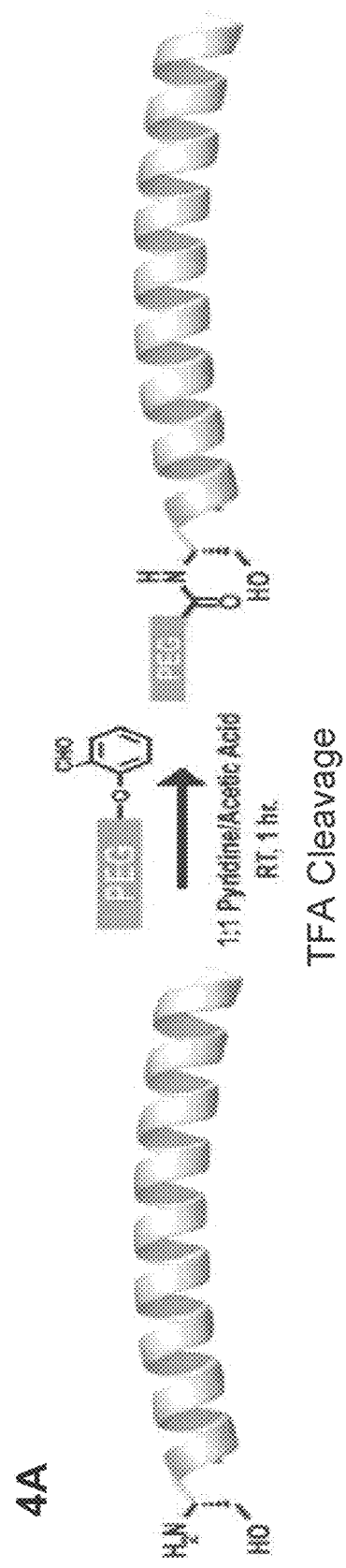
FIG. 4A-D shows synthesis of N-terminal PEGylated PTH (1-34) A) Schematic diagram of ligation between PEG-salicylaldehyde and PTH (1-34) containing an N-terminal serine residue (PDB ID: 1ET1). Final protein concentration=10 mM. B) Analytical HPLC analysis of the ligation reaction. C) MALDI-TOF analysis of purified PTH (1-34) (blue) and the crude ligation reaction after cleavage (red). D) Circular dichroism spectra of PTH (1-34) (blue) and N-terminal PEGylated PTH (1-34) (red). Scans were performed at 25° C. in 10 mM PBS buffer (pH 7.5).
Figure 4:
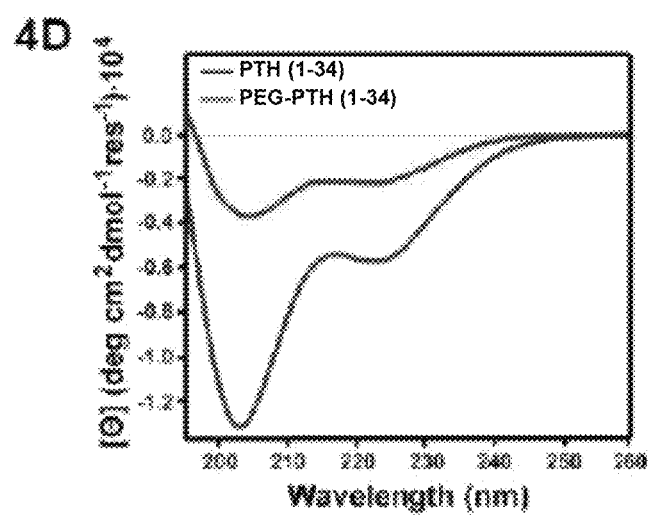

In another embodiment, the polypeptide, when present, is PTH (1-34), an exemplary polypeptide that can be conjugated to PEG or AG moieties using methods described herein. See, for example, Examples presented herein and FIG. 4.

In another embodiment, the polypeptide, when present, is a long peptide chain.

In another embodiment, the polypeptide, when present, comprises more than 100 amino acid residues.

In another embodiment, the polypeptide, when present, comprises between 50-100 amino acid residues.

In another embodiment, the polypeptide, when present, is a short peptide chain.

In another embodiment, the polypeptide, when present, comprises fewer than 50 amino acid residues.

In another embodiment, the polypeptide, when present, comprises amino acid residues; and the amino acid residues are selected from one or more glycine, L-lysine, L-cysteine, L-aspartic acid, L-asparagine, L-glutamine, L-alanine, L-valine, L-leucine, L-iso-leucine, L-tyrosine, L-proline, L-serine, L-threonine, L-glutamic acid, L-tryptophan, L-phenylalanine, L-methionine, L-arginine, and L-histidine residues.

In one embodiment, X is —$NH_2$.

In another embodiment, X is —OH.

In another embodiment, X is —O-alkyl.

In another embodiment, X is —OMe, or —OEt.

In another embodiment, m is an integer between 2-200, 2-100, 2-50, 2-30, 2-20, 2-10, or 2-5.

In another embodiment, n is an integer between 2-1000, 2-500, 2-400, 2-200, 2-100, 2-50, 2-30, 2-20, 2-10, or 2-5.

In yet another aspect, the present invention provides PEGylated polymers comprising one or more backbone-attached pendant groups, wherein each of the backbone-attached pendant groups is attached to the backbone directly or via a linker group to the backbone of the PEGylated polymer; and wherein the pendant group is $R^5$ and $R^5$ is:

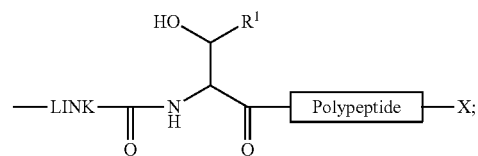

and wherein LINK is an alkylene; and X is hydroxyl, alkoxy, amino or substituted amino.

In one particular embodiment, the polymer is according to formula XIII:

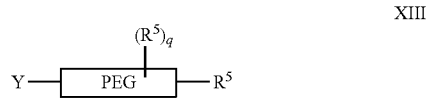

wherein $R^5$ is as described above; the subscript q is an integer from 0-20; PEG is a PEGylated polymer backbone; Y is $R^5$, —O—$R^2$, —O—C(O)—$R^2$, —NH—C(O)—$R^2$ or —NH—C(O)—O—$R^2$; and $R^2$ is H, alkyl, or aryl.

In yet another aspect, the present invention provides processes for preparing a polymer according to formula XIII:

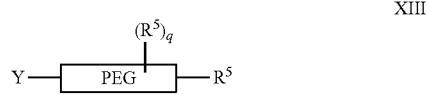

or a pharmaceutically acceptable salt, stereoisomer, isotopic variant or tautomer thereof;

comprising the steps of

C1) providing a compound of formula II:

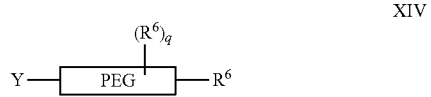

C2) reacting the compound of formula XIV with a polypeptide of formula III:

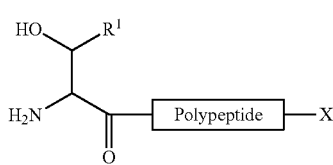

to form the compound of formula XV:

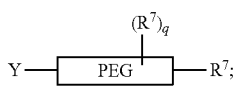

and

C3) reacting the oxazolidine compound of formula XV with an acid to form the polymer of formula XIII;

wherein the subscript q is an integer from 0-20; PEG is a PEGylated polymer backbone; Y is $R^5$, —O—$R^2$, —O—C(O)—$R^2$, —NH—C(O)—$R^2$ or —NH—C(O)—O—$R^2$; $R^2$ is H, alkyl, or aryl;

X is hydroxyl, alkoxy, amino or substituted amino;

$R^1$ is H or methyl;

each $R^2$ is independently H, alkyl, or aryl;

each $R^4$ is independently H or substituted or unsubstituted alkyl;

and the subscript t is 1, 2, 3, or 4;

each $R^6$ is independently

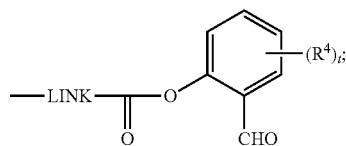

and each $R^7$ is independently

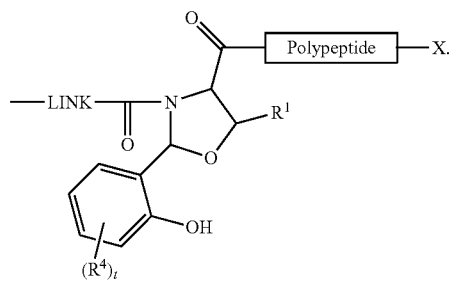

In yet another aspect, the present invention provides compounds according to formula XV:

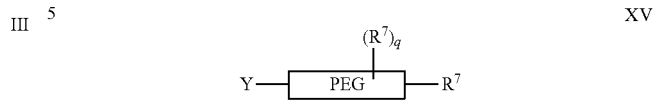

or a stereoisomer, a tautomer, or an isotopic variant thereof;

wherein PEG, Y, $R^7$ and q are as in claim 105.

In one embodiment, LINK is $C_2$-$C_{20}$ alkylene or LINK is $C_2$-$C_6$ alkylene.

In one embodiment, LINK is ethylene, propylene, or butylenes.

In one embodiment, LINK is substituted or unsubstituted ethylene.

In one embodiment, LINK is —$CH_2$—$CH_2$—.

In one embodiment, the reaction occurs in the presence of a solvent.

In one embodiment, the reaction occurs in the presence of methylene chloride, ethylene chloride, or tetrachloroethane.

In one embodiment, the reaction occurs in the presence of methylene chloride.

In one embodiment, the reaction occurs in the presence of diisopropylcarbodiimide.

In one embodiment, the reaction occurs in the presence of diisopropylcarbodiimide (DIC); and the DIC is about 1.2 equivalent of IX or X.

In one embodiment, the reaction occurs in the presence of a catalyst.

In one embodiment, the reaction occurs in the presence of a catalytic amount of dimethylaminopyridine (DMAP).

In one embodiment, the reaction occurs at around 20-30° C.

In one embodiment, the reaction occurs for 4-24 hrs.

In one embodiment, the step C2 occurs in the presence of a solvent.

In one embodiment, the step C2 occurs in the presence of a solvent; and the solvent is pyridine.

In one embodiment, the step C2 occurs in the presence of an acid.

In one embodiment, the step C2 occurs in the presence of acetic acid.

In one embodiment, the step C2 occurs in the presence of 1:1 mole/mole pyridine and acetic acid.

In one embodiment, the step C2 occurs at around 20-30° C.

In one embodiment, the step C3 occurs in the presence of solvent.

In one embodiment, the step C3 occurs in the presence of an acid.

In one embodiment, the step C3 occurs in the presence of trifluoroacetic acid (TFA).

In one embodiment, the step C3 occurs in the presence of i-$Pr_3$SiH.

In one embodiment, the step C3 occurs in the presence of water.

In one embodiment, the step C3 occurs in the presence of TFA, water and i-$Pr_3$SiH (94/5/1, v/v/v).

In one embodiment, the step C3 occurs for 0.1 to 2 hrs.

In one embodiment, $R^1$ is H.

In one embodiment, $R^1$ is Me.

In one embodiment, each of $R^3$ is independently Me, Et, n-Pr, i-Pr, n-Bu, sec-Bu, or i-Bu.

In one embodiment, each of $R^3$ is independently phenyl or benzyl, unsubstituted or substituted with one or more groups selected from alkyl, halo, hydroxy, amino, nitro, and alkoxy.

In one embodiment, each of $R^3$ is independently phenethyl, unsubstituted or substituted with one or more groups selected from alkyl, halo, hydroxy, amino, nitro, and alkoxy.

In one embodiment, each of $R^3$ is independently 2-naphthyl, unsubstituted or substituted with one or more groups selected from alkyl, halo, hydroxy, amino, nitro, and alkoxy.

In one embodiment, each of $R^3$ is independently 2,2-diphenylethyl, unsubstituted or substituted with one or more groups selected from alkyl, halo, hydroxy, amino, nitro, and alkoxy.

In one embodiment, each of $R^3$ is independently furanyl or thienyl, unsubstituted or substituted with one or more groups selected from alkyl, halo, hydroxy, amino, nitro, and alkoxy.

In one embodiment, each of $R^3$ is independently aminomethyl, 2-aminoethyl, 3-aminopropyl, 4-aminobutyl, 5-aminopentyl, or 6-aminohexyl.

In one embodiment, each of $R^3$ is independently 3-aminopropyl.

In one embodiment, each of $R^3$ is independently guanidinoalkyl.

In one embodiment, each of $R^3$ is independently guanidinomethyl, 2-guanidinoethyl, 3-guanidinopropyl, 4-guanidinobutyl, 5-guanidinopentyl, or 6-guanidinohexyl.

In one embodiment, each of $R^3$ is independently 4-guanidinobutyl.

In one embodiment, each of $R^3$ is independently imidazolylmethyl, 2-imidazolylethyl, 3-imidazolylpropyl, 4-imidazolylbutyl, 5-imidazolylpentyl, or 6-imidazolylhexyl.

In one embodiment, each of $R^3$ is independently methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In one embodiment, each of $R^3$ is independently Me, i-Pr, i-Bu, sec-Bu, phenethyl, 4-hydroxyphenethyl, benzimidazol-3-ylmethyl, thiomethyl, methylthioethyl, hydroxymethyl, aminopropyl, guanadinopropyl, or imdazo-4-yl methyl In one embodiment, t is 4; and each of $R^4$ is H; or t is 1 or 2, and each of $R^4$ is independently Me, Et, i-Pr or $CF_3$.

In one embodiment, the polypeptide is a protein.

In one embodiment, the polypeptide is PTH (1-34).

In one embodiment, the polypeptide is a long peptide chain.

In one embodiment, the polypeptide comprises more than 100 amino acids residues.

In one embodiment, the polypeptide comprises between 50-100 amino acid residues.

In one embodiment, the polypeptide is a short peptide chain.

In one embodiment, the polypeptide comprises fewer than 50 amino acid residues.

In one embodiment, the polypeptide, comprises amino acid residues; and the amino acid residues are selected from one or more glycine, L-lysine, L-cysteine, L-aspartic acid, L-asparagine, L-glutamine, L-alanine, L-valine, L-leucine, L-iso-leucine, L-tyrosine, L-proline, L-tyrosine, L-serine, L-glutamic acid, L-tryptophan, L-phenylalanine, L-methionine, L-arginine, and L-histidine residues.

In one embodiment, X is —$NH_2$.

In one embodiment, X is —OH.

In one embodiment, X is —O-alkyl.

In one embodiment, X is —OMe, or —OEt.

In one embodiment, Y is —O—$R^2$, or —O—C(O)—$R^2$.

In one embodiment, Y is —O—$R^2$; and $R^2$ is acetyl, lauroyl, tridecanoyl, myristoyl, pentadecanoyl, palmitoyl, caproyl, benzoyl, cetyl, decyl, acetyl, phenyl acetyl, cyclohexyl acetyl, valeroyl, or glucuronyl residue.

In one embodiment, Y is —$OCOCH_3$.

In one embodiment, Y is —NH—C(O)—$R^2$ or —NH—C(O)—O—$R^2$.

In one embodiment, Y is NH—$COCH_3$.

In one embodiment, Y is NH-t-Boc.

In one embodiment, the invention provides a pharmaceutical composition of the novel polymers of formula I or V, comprising a pharmaceutically acceptable carrier, and the carrier is a parenteral carrier, oral or topical carrier.

In one embodiment, the invention provides a method for preventing, treating, ameliorating or managing a disease or condition which comprises administering to a patient in need of such prevention, treatment, amelioration or management, a prophylactically or therapeutically effective amount of the pharmaceutical composition of the novel polymer of formula I.

In one embodiment, the invention provides a method for preventing, treating, ameliorating or managing a disease or condition, which comprises administering to a patient in need of such prevention, treatment, amelioration or management a prophylactically or therapeutically acceptable amount of a polymer of formula I, or the pharmaceutical composition thereof.

Pharmaceutical Compositions

When employed as pharmaceuticals, the novel compounds of this invention are typically administered in the form of a pharmaceutical composition. Such compositions can be prepared in a manner well known in the pharmaceutical art and comprise at least one active complex. Such combinations yield compositions that exhibit improved effectiveness over like compositions containing the active compounds individually, so that a synergistic effect of the combination is conferred. The exact amounts and proportions of the compounds with respect to each other may vary within the skill of the art.

Exemplary PEGylated compounds of the invention include, without limitation, cytokines, growth factors, enzymes, peptides, small molecules, antibodies and functional fragments thereof (e.g., including F(ab')$_2$ and Fab fragments). PEGylated compounds such as these can be used in a variety of therapeutic indications, including inflammatory conditions (e.g., rheumatoid arthritis and Crohn's disease), cancer, endocrine disorders, genetic disorders, and infectious disease. Examples of PEGylated products that are approved for use and available to the public include: PEG-adenosine deaminase (ADAGEN®), which is used to treat severe combined immunodeficiency disease; Pegaspargase (ONCASPAR®), which is used to treat acute lymphoblastic leukemia in patients who are hypersensitive to the native unmodified form of L-asparaginase; Peginterferon alpha-2b (PEGINTRON®), which is used to treat chronic hepatitis C; PEGylated interferon alpha (PEGASYS®), which is used to treat chronic hepatitis C and B; PEGfilgrastim (NEULASTA®), which is used to treat severe cancer chemotherapy-induced neutropenia; PEG-human growth hormone mutein antagonist (SOMAVERT®), which is used to treat acromegaly; Pegaptanib (MACUGEN®), which is used to treat neovascular age-related macular degeneration; Methoxy polyethylene glycol-epoetin beta (MIRCERA®) and PEGinesatide (OMONTYS®), which are each used to treat anemia associated with chronic kidney disease; Certolizumab Pegol (CIMZIA®), which is used to treat rheumatoid arthritis and Crohn's disease; and Pegloticase (KRYSTEXXA®), which is used to treat gout (reviewed in J. Kling *BioProcess International* 2013, 11, 35-43, the entire content of which is incorporated herein by incorporation). It will be appreciated that the methods described herein may be used to generate PEGylated compounds of the above proteins (e.g., interferon alpha or epoetin beta) having unique structures that differ from those of the PEGylated products already on the market. In circumstances wherein one of the aforementioned proteins does not comprise an N-terminal serine or threonine, one of skill in the art would be aware of various protocols that can be used to incorporate or engineer one of these amino acids into the N-terminus of such a protein. Accordingly, such novel PEGylated compounds are envisioned herein, as are therapeutic uses thereof in accordance with those therapeutic uses for which the marketed PEGylated products have already received FDA approval.

A number of PEGylated products are also in varying states of development, including, without limitation, PEGylated recombinant phenylalanine ammonia lyase for treating phenylketonuria (Phase II clinical trial); PEGylated irinotecan for treating colorectal cancer (Phase II clinical trial) and other solid cancers; PEGylated conjugate of SN38 for treating metastatic breast cancer and metastatic colorectal cancer (Phase II clinical trials) and for treating pediatric solid tumors and solid tumors (Phase I clinical trials); and PEGylated docetaxel for treating locally advanced or metastatic breast cancer, non small-cell lung cancer in patients who have relapsed following anthracycline-based chemotherapy, and hormone refractory prostate cancer (reviewed in J. Kling *BioProcess International* 2013, 11, 35-43). The methods described herein may be used to generate PEGylated compounds of the above agents (e.g., recombinant phenylalanine ammonia lyase, irinotecan, or SN38) having unique structures that differ from those of the PEGylated products in development. Where necessitated, a protein of interest can be modified to include an N-terminal serine or threonine residue using methods commonly used in the art. Accordingly, such novel PEGylated compounds are envisioned herein, as are therapeutic uses thereof in accordance with those therapeutic uses for which the unPEGylated agents have been used and for which the PEGylated products are being tested in, for example, clinical trials.

Generally, a PEGylated compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non limiting example, oral, inhaled, rectal, vaginal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Other Applications for PEGylated Compounds

PEGylation has also been used successfully to preserve the function of various enzymes (e.g., alpha-chymotrypsin, lipase, and catalase) in organic solvents (Castillo et al, *Biotechnol. Bioeng.* 2006, 94, 565-574; Inada et al, *Trends Biotechnol.* 1986, 4, 190-194; DeSantis et al, *Curr. Opin. Biotechnol.* 1999, 10, 324-330). PEGylated proteins have also been used in the textile industry to enhance desirable properties of wool (Schroeder et al, *Biocatal. Biotransformation* 2004, 22, 299-305). PEGylation has also been used to improve stain removing properties of laundry detergents at low temperatures, which in turn improves color retention in fabrics (Schroeder et al, *Appl. Microbiol. Biotechnol.* 2006, 72, 738-744). PEGylation has also been used to improve the stability of proteins used as biosensors in various assays (Santiago-Rodriguez et al, *J. Electroam. Chem.* 2011, 663, 1-7; Dattelbaum et al, *Bioconjug. Chem.* 2009, 20, 2381-2384; Gonzalez-Valdez et al, *Anal. Bioanal. Chem.* 2012, 403, 2225-2235). In light of the above, PEGylation and PEGylated compounds have shown great utility in a diverse array of purposes important in a variety of industries.

PEGylation may also have applicability to cell-based and tissue-based therapies. Adverse immune responses to cell-based and tissue-based therapies present major impediments for transplantation medicine. PEGylation shows promise in this regard as it has been used to mask erythrocytes and other cells by means thought to include camouflaging antigenic sites and membrane surface charge, as well as by physically blocking receptor-ligand and intercellular contacts. The efficacy of PEG-mediated immunocamouflage was, moreover, evident in in vivo murine models of transfusion-associated graft versus host disease. Intriguingly, studies with PEGylated rat and mouse pancreatic islet cells suggest that PEG-derivatization does not impair glucose homeostasis signaling (Scott et al, *Transfus. Clin. Biol.* 2004, 11, 40-46).

In similar fashion, PEGylation may have promise as a means to disguise medical implants from attack by a host immune system. Coatings comprising PEGylated hydrophilic peptides or proteins could potentially be used to disguise plastic and metal implants, thereby thwarting immune cell detection. Such coatings would also confer PEG-mediated inhibition of cellular interactions in general, which would reduce the likelihood of infection and undesired tissue growth on implanted devices (Kenan et al, *Chem. Biol.* 2006, 13, 695-700). Indeed, a PEGylated-peptide has been shown to coat titanium metal, which is commonly used in implants, thereby generating a nonfouling surface that efficiently blocked the adsorption of fibronectin and significantly reduced the extent of *Staphylococcus aureus* attachment and biofilm formation in vitro. Accordingly, PEGylated-peptide coatings may help to resolve two major hurdles common to implanted metals, namely nonspecific protein adsorption and bacterial colonization (Khoo et al, *J. Am. Chem. Soc.* 2009, 131, 10992-10997).

It is, furthermore, envisioned that methods presented herein can be used to generate PEGylated proteins and peptides that can be used in applications for which PEGylated proteins and peptides are known to be used, including each and every one of the aforementioned applications.

Synthetic Process of the Invention

General Synthetic Method for Synthesis of Novel Polymers of the Invention

The novel polymers of the invention can be synthesized following the synthetic schemes given below:

Scheme 1
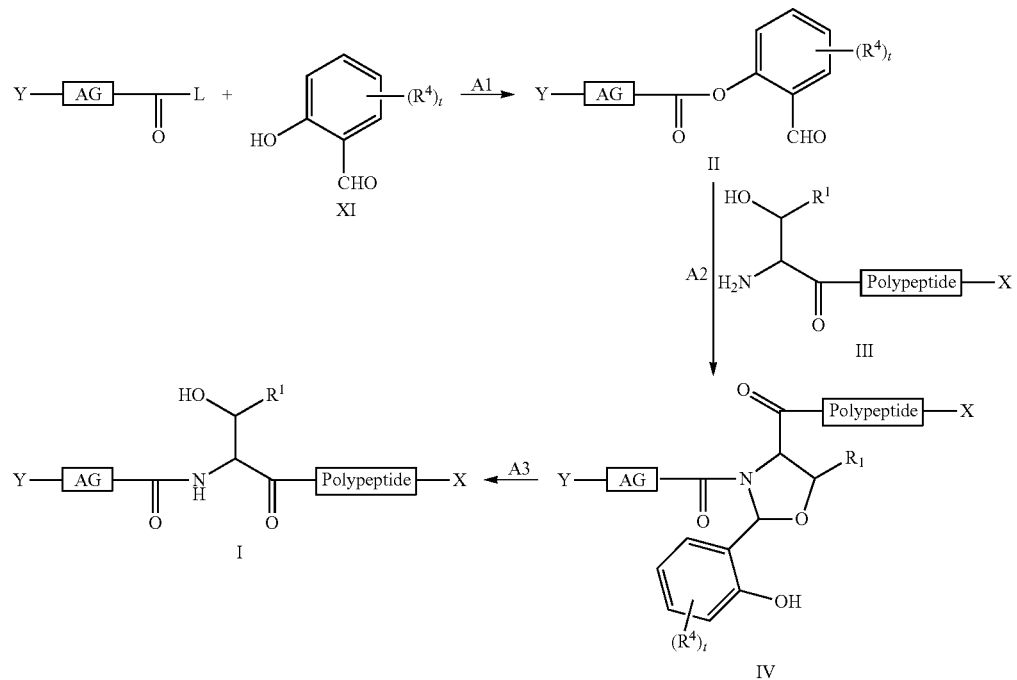
and wherein AG, Polypeptide, X, Y, $R^1$, $R^4$, L, and t are as described herein.
Scheme 2
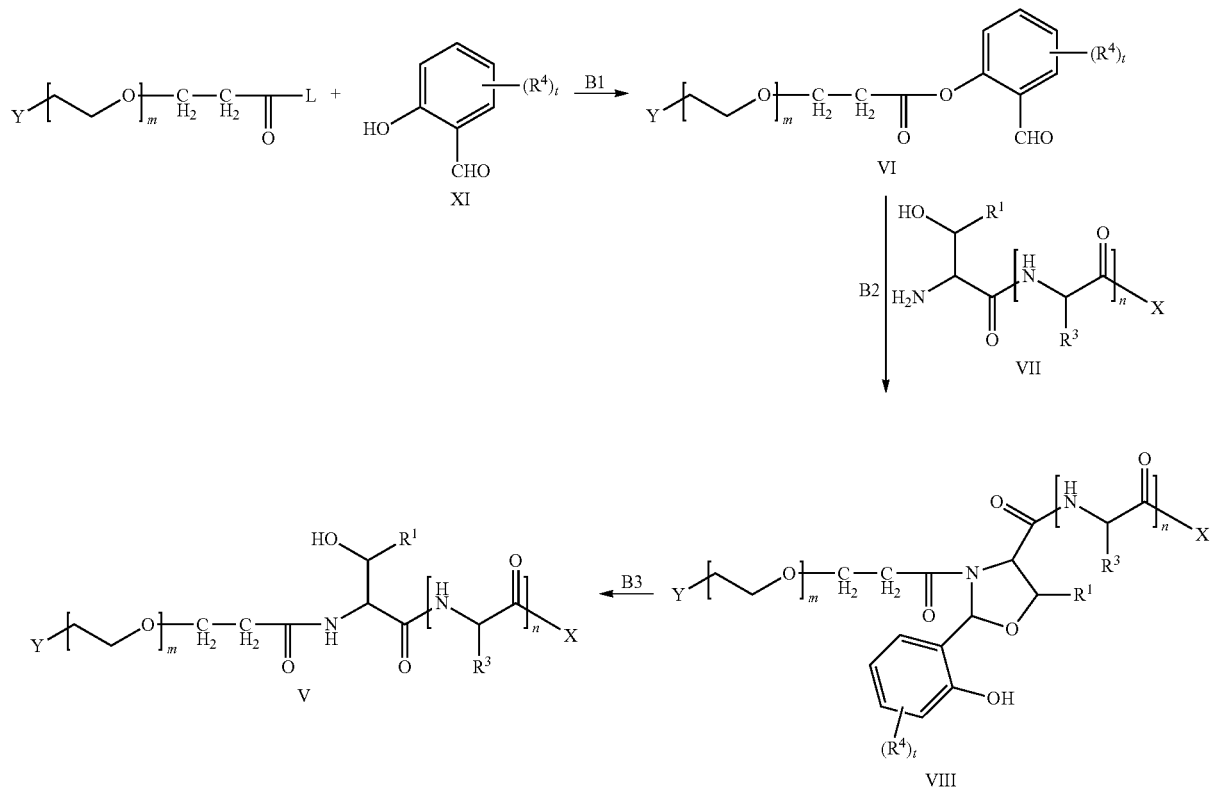

and wherein Polypeptide, X, Y, $R^1$, $R^3$, $R^4$, L, m and t are as described herein.

Figure 2:
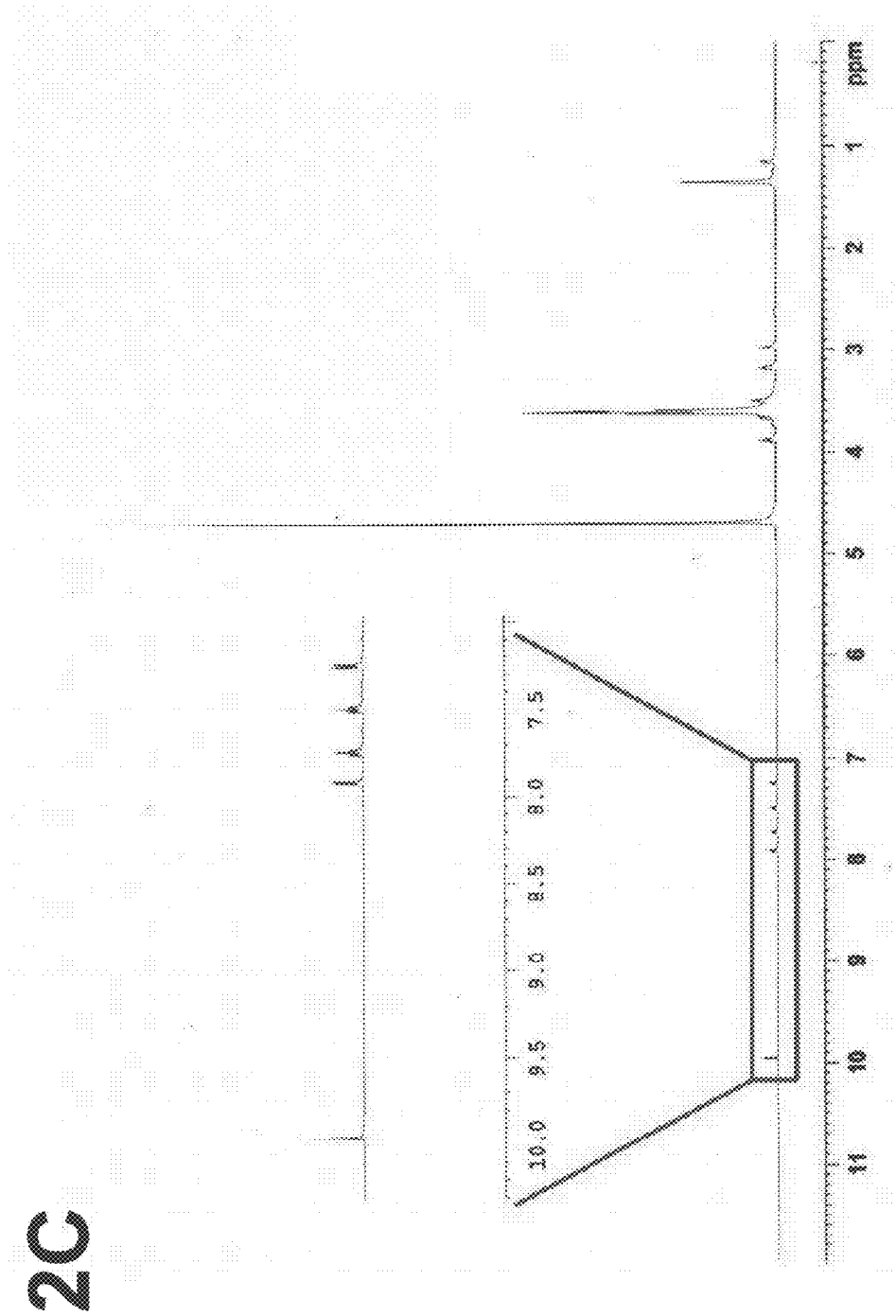
FIG. 2A-C shows synthesis and characterization of a monodisperse PEG-salicylaldehyde. A) PEG-salicylaldehyde was synthesized from commercially available starting material. Electrospray ionization (ESI) mass spectrometry (B) and $^1$H-NMR (C) confirm formation of a monodisperse PEG-salicylaldehyde. DIC: N,N'-Diisopropylcarbodiimide; DMAP: 4-Dimethylaminopyridine.

In the above scheme AG moiety is PEG or polyethylene glycol moiety. A representative PEG salicylaldehyde (II) is prepared from commercially available starting material(s) (FIG. 2A). The product is purified using HPLC and characterized by electrospray ionization (ESI) mass spectrometry. For example, the PEG salicylaldehyde where Y is —NH-Boc, PEG is $(-CH_2-CH_2-O-)_{12}-CH_2-CH_2-$, and $R^4$ is H, showed observed mass (m/z) of 844.8 (calcd. m/z 844.4) (FIG. 2B). In addition, 1H-NMR is used to characterize PEG-salicylaldehyde due to the distinct chemical shifts of the aldehyde and aromatic protons (FIG. 2c). Relative to starting material, PEG-salicylaldehyde displays the addition of salicylaldehyde as confirmed by the appearance of a sharp singlet around 10 ppm and peaks between 7-8 ppm in the 1H-NMR spectrum.

Figure 3:
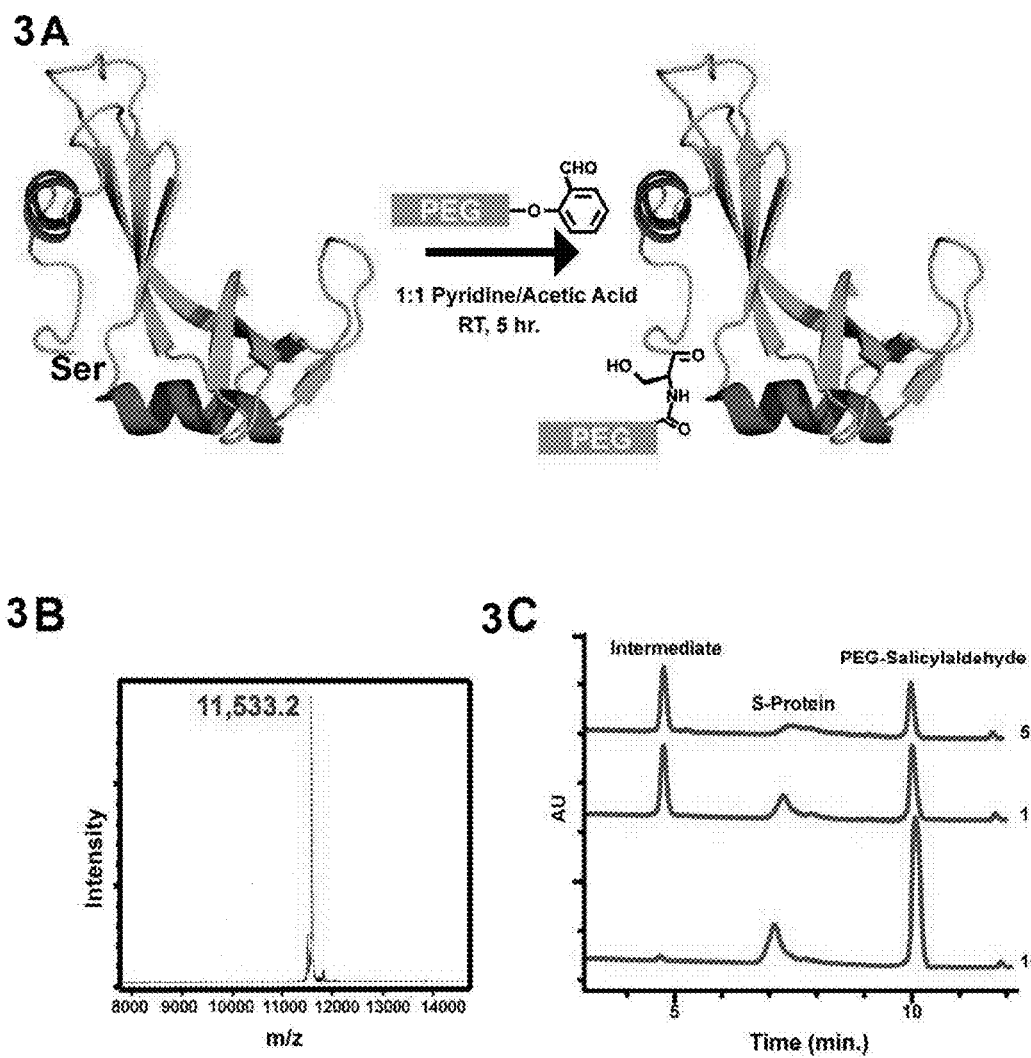
FIG. 3A-F shows synthesis of N-terminal PEGylated S-protein by ligation and characterization. A) Schematic diagram of serine ligation between PEG-salicylaldehyde and the S-protein containing an N-terminal serine residue (PDB ID: 1FS3). Final protein concentration=10 mM. B) MALDI-TOF analysis of purified S-protein. C) Analytical HPLC analysis of the ligation reaction. D) MALDI-TOF analysis of the crude ligation reaction after cleavage, confirming formation of PEGylated S-protein. E) SDS-PAGE analysis of crude ligation reaction after cleavage (lane 1, marker; lane 2, WT S-protein; lane 3, PEGylated S-protein). F) Circular dichroism spectra of S-protein (blue) and N-terminal PEGylated S-protein (red). Scans were performed at 25° C. in 10 mM PBS buffer (pH 7.5).
Figure 3:
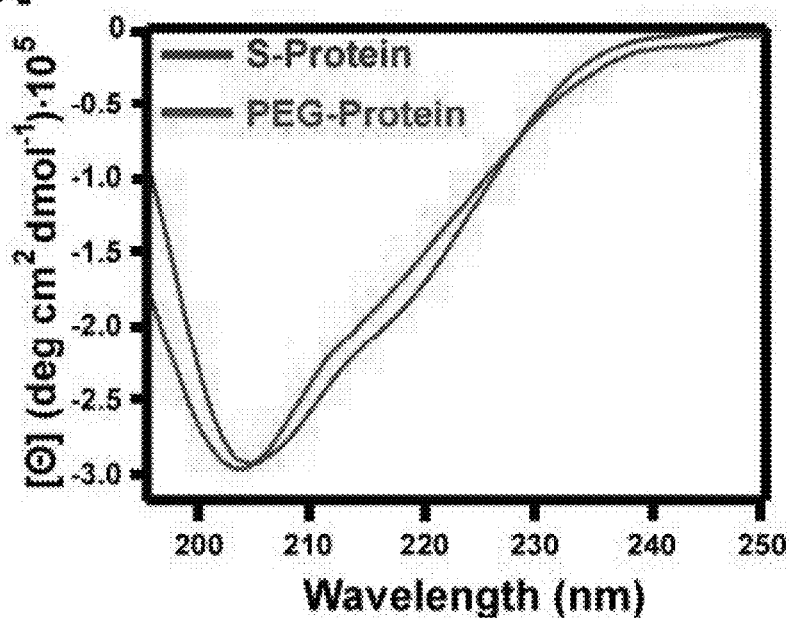

S-protein (formula III, polypeptide with terminal serine/threonine residue) is generated from bovine pancreatic ribonuclease A (RNase A) by proteolysis. S-protein contains an N-terminal serine residue required for ligation (FIG. 3A). The N-terminal portion of RNase A (residues 1-20), termed the S-peptide, can be excised by enzymatic cleavage using subtilisin to provide the S-protein (A. T. Fafarman et al, *J. Phys. Chem. B*, 2010, 114, 13536-13544; E. R. Simons et al, *J. Biol. Chem.*, 1967, 243, 218-221). Following HPLC purification and characterization by matrix-assisted laser desorption ionization time of flight mass spectrometry (MALDI-TOF), the corresponding S-protein is obtained (calc. m/z: 11,534.3; obs. m/z: 11,533.2, FIG. 3B).

PEG-salicylaldehyde, as prepared above, is coupled to the S-protein in the presence of 1:1 pyridine/acetic acid forming the corresponding N,O-benzylidene acetal intermediate of formula IV. This reaction is monitored by analytical HPLC, which established that coupling is complete after 5 hours (FIG. 3C). Following completion of the reaction (consumption of the S-protein), the intermediate is cleaved with TFA to afford the PEGylated protein conjugated through a native amide bond. MALDI-TOF analysis of the crude reaction confirmed formation of PEGylated S-protein (FIG. 3D). Following lyophilization of the aqueous solution, the crude PEGylated protein is assessed for homogeneity by gel electrophoresis (FIG. 3E). As expected, Coomassie staining revealed a distinct band corresponding to a discrete mono-PEGylated S-protein. Despite containing seven lysine residues within the S-protein, all characterization data is consistent with site-specific modification at the N-terminus. This result is distinct from other methods in which PEG chains incorporating reactive groups are conjugated to multiple sites within a protein chain that bear nucleophilic or other reactive species such as primary amines (lysine) or sulfhydryls (cysteine).

To evaluate any conformational perturbations associated with N-terminal PEGylation of the S-protein, far-UV circular dichroism (CD) spectroscopy is used. The CD signature of N-terminal PEGylated S-protein is comparable to that of the wild-type S-protein, with a characteristic minimum observed at ~204 nm (FIG. 3F) (E. R. Simons et al, *J. Biol. Chem.*, 1967, 243, 218-22). These results suggest that N-terminal PEGylation of the S-protein has negligible impact on the overall structure of the protein.

Next, the inventors used serine ligation to generate an N-terminal PEGylated variant of parathyroid hormone (1-34) or PTH (1-34) (FIG. 4A). PTH (1-34) is a therapeutic polypeptide that agonizes the class B G-protein-coupled receptor PTHr1 and is currently marketed (as Forteo®) to enhance bone density and formation in patients diagnosed with osteoporosis. PTH (1-34) exhibits a poor half-life in serum (~5 min), making it an attractive target for PEGylation to potentially enhance proteolytic stability (D. Narayanan, et al, *Mol. Pharmaceutics*, 2013, 10, 4159-4167). PEG-salicylaldehyde was therefore ligated to the N-terminal serine residue of PTH (1-34). The reaction was monitored by analytical HPLC, which determined that coupling was complete after 1 hour (FIG. 4B). Following completion (consumption of PTH 1-34), the intermediate was cleaved with TFA to afford the PEGylated peptide, as determined by and MALDI-TOF (calc. m/z: 4,736.5; obs. m/z: 4,736.4, FIG. 4C).

The helical character at the C-terminus of PTH (1-34) has been shown to be critical for recognition by the PTHr1 receptor (A. A. Pioszak et al, *Proc. Natl. Acad. Sci. USA*, 2008, 105, 5034-5039). In this case, the CD spectrum of PEGylated PTH (1-34) displayed a loss of secondary structure relative to the unmodified polypeptide (M. Pellegrini, et al, *J. Biol. Chem.*, 1998, 273, 10420-10427). These results suggest that this modification at the N-terminus of PTH (1-34) can have a significant impact on the structure of the therapeutic peptide. Recent evidence has shown that N-terminal PEGylation of small helical peptides can affect peptide helicity (E. Hamed, et al, *Biomacromolecules*, 2013, 14, 4053-4060).

Figure 11:
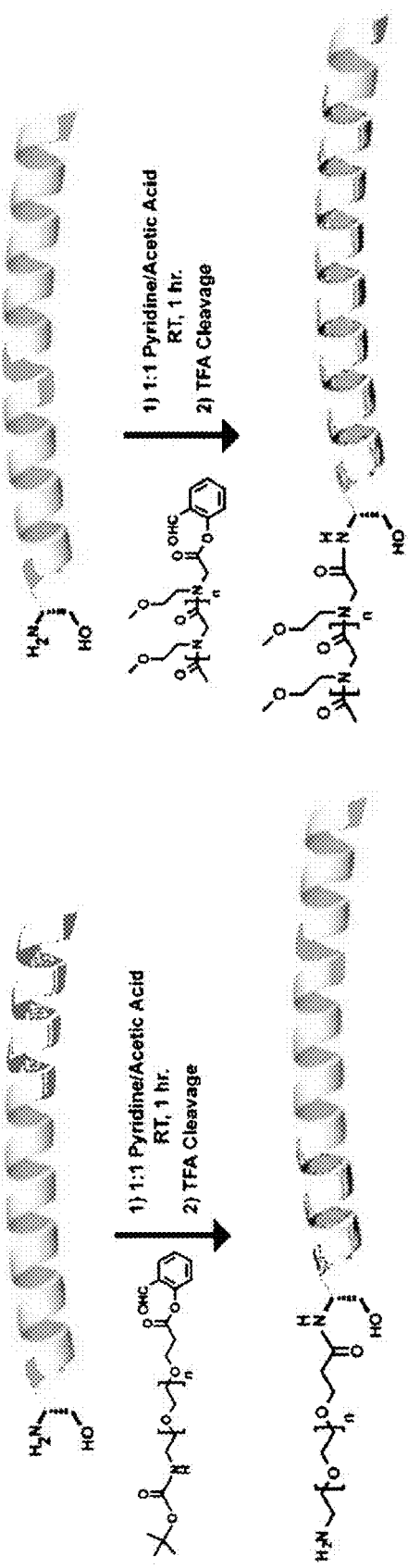
FIG. 11 presents the generic chemical structures of PTH compounds synthesized, wherein PTH1-34 is depicted as a grey helix.

Further to the above, the present inventors have evaluated six N-terminally modified PTH 1-34 compounds in a luciferase based assay (GloSensor, Promega Corp.) to establish their ability to activate the PTH receptor. All compounds exhibited full agonistic activity with nanomolar concentrations (~3-20 nM). FIG. 11 shows an image with the generic chemical structures of the compounds (PTH1-34 is depicted as a grey helix).

The invention described herein establishes a robust synthetic route for rapidly and site-specifically introducing PEG chains onto peptides and proteins through native amide linkages at N-terminal serine residues. Chemoselective fragment condensation reactions were conducted using either the S-protein or PTH (1-34) and PEG-salicylaldehyde. The inventors envision that this method will be applicable to bioconjugate homogeneous or heterogeneous PEG chains onto the N-terminus of various peptides and proteins (e.g., therapeutics) in a site-specific fashion to potentially enhance their functional attributes.

General Synthetic Procedures

The novel polymers of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M.

Wuts, *Protecting Groups in Organic Synthesis*, Second Edition, Wiley, New York, 1991, and references cited therein.

The following methods are presented with details as to the preparation of representative PEGylated polymers that have been listed hereinabove. The PEGylated polymers of the invention may be prepared from known or commercially available starting materials and reagents by one skilled in the art of organic synthesis.

Solvents and reagents purchased from commercial sources were used without further purification. Abbreviations for reagents are as follows: 9-fluorenylmethoxycarbonyl (Fmoc); tert-butoxycarbonyl (Boc); benzotriazole-1-yl-oxy-tris-pyrrolidino-phosphonium hexafluorophosphate (PyBOP); Bromo-tris-pyrrolidino phosphoniumhexafluorophosphate (PyBrOP); trifluoroacetic acid (TFA); hexafluoroisopropyl alcohol (HFIP); methylene chloride (DCM); N,N'-dimethylformamide (DMF); N,N'-diisopropylcarbodiimide (DIC); diisopropylethylamine (DIEA); acetonitrile (ACN); N-methylmorpholine (NMM); O-Benzotriazole-N,N,N',N'-tetramethyl-uronium-hexafluoro-phosphate (HBTU).

The submonomer amines 2-methoxyethylamine, propargylamine, allylamine, propylamine, aniline, (S)-(−)-1-phenylethylamine, and benzylamine were purchased from either Aldrich or TCI America. Other reagents were obtained from commercial sources and used without additional purification.

Ribonuclease A (≥60% SDS-PAGE) and subtilisin were purchased from Sigma Aldrich. Starting PEG material (t-boc-N-amido-sPEG$_{12}$-acid, >94%) was purchased from Quanta Biodesign. Other reagents were obtained from commercial sources and used without additional purification.

HPLC analysis and purifications were performed on a Agilent instrument. For analytical analysis, a $C_{18}$ reversed-phase HPLC column was used (Peeke Scientific). Samples were eluted with a 5-95% acetonitrile/water gradient (0.1% TFA) in 20 minutes with a flow rate of 0.7 mL/min and monitored at 214 nm. For purifications, semi-preparative $C_{18}$ reversed-phase HPLC columns were used (Peeke Scientific). Samples were eluted with a 5-95% acetonitrile/water gradient (0.1% TFA) in 50 minutes with a flow rate of 2.5 mL/min, and monitored at 214 nm.

All mass spectrometry data was obtained on either a Agilent 1100 Series LCMSD VL Mass Spectrometer or a Bruker UltrafleXtreme MALDI-TOF mass spectrometer in positive-ion mode. Matrix: Sinapic acid in acetonitrile with 0.01% TFA.

Representative Synthetic Methods

Synthesis of PEG-Salicylaldehyde and Ligation Reaction Conditions

EXAMPLE 1

Preparation of S-Protein:

S-protein was prepared as previously reported (A. T. Fafarman et al. *J. Phys. Chem. B*, 2010, 114, 13, 536).

General Procedure for the Preparation of PEG-Salicylaldehyde:

~25 mg of t-boc-Namido-sPEG12-acid was suspended in dry DCM and 1.2 eq. of DIC, 1.1 eq. of salicylaldehyde, and 0.1 eq. of DMAP were added. The reaction was stirred at RT for 16 hours and then purified by reversed-phase HPLC.

General Procedure for Ligation:

S-protein (2 mg) or PTH 1-34 (2 mg) was dissolved in pyridine/acetic acid (1:1 v/v) to a final concentration of ~10 mM and PEG-salicylaldehyde (~2 equiv.) was added. The reaction was stirred at room temperature and monitored using MALDI-TOF and HPLC. Following completion of the reaction (consumption of salicylaldehyde to form the acetal intermediate), the solvent was removed by lyophilization and the intermediate product was treated with TFA/H2O/i-Pr3SiH (94/5/1, v/v/v) for 2 hr to give the product containing a native amide bond at the ligation site.

Circular Dichroism (CD) Spectroscopy:

Circular Dichroism spectra were measured on an Aviv spectrophotometer (Lakewood, N.J.). Spectra were acquired at concentrations of 10 μM oligomer in 10 mM PBS (pH 7.5) in a 1 mm cuvette. Wavelength-dependent spectra were acquired from 260 nm to 180 nm (data pitch 0.5 nm, scan speed 50 nm/min, 4 sec, 1 nm bandwidth and 10 accumulations). Mean residue ellipticity values were calculated from the equation MRE=(Θsample−Θbuffer)/(L·c·n), where Θ is observed signal in millidegrees, L is the length of the cuvette in cm, c is the concentration of peptide in dmol/cm³, and n is the number of residues in the peptide and peptoid oligomers.

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for peptoid oligomers are approximate, and are provided for description.

All publications, including but not limited to patents and patent applications, cited in this specification are herein incorporated by reference as if each individual publication were specifically and individually indicated to be incorporated by reference herein as though fully set forth.

What is claimed is:

1. A compound according to formula V:

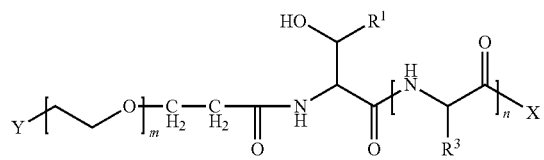

or a pharmaceutically acceptable salt, stereoisomer, isotopic variant or tautomer thereof;

wherein

X is hydroxyl, alkoxy, amino or substituted amino;

Y is hydroxy, protected hydroxyl, amino or protected amino; or Y is —O—R², —O—C(O)—R², —NH—C(O)—R² or —NH—C(O)—O—R²;

R¹ is H or methyl;

each R² is independently H, alkyl, or aryl;

each R³ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;

the subscript m is an integer from 2-200; and the subscript n is an integer from 2-1000;

provided that the compound is other than the compounds "Excluded Compounds 1-25" listed below:

Excluded Compound 1
CAS Registry Number: 1379581-54-0;
Excluded Compound 2
CAS Registry Number: 1353563-96-8;
Excluded Compound 3
CAS Registry Number: 1254174-69-0;
Excluded Compound 4
CAS Registry Number: 1254174-68-9;
Excluded Compound 5
CAS Registry Number: 1242240-17-0;
Excluded Compound 6
CAS Registry Number: 1242240-03-4;
Excluded Compound 7
CAS Registry Number: 1199579-48-0;
Excluded Compound 8
CAS Registry Number: 1199579-43-5;
Excluded Compound 9
CAS Registry Number: 1189539-31-8;
Excluded Compound 10
CAS Registry Number: 1189539-30-7;
Excluded Compound 11
CAS Registry Number: 1189539-29-4;
Excluded Compound 12
CAS Registry Number: 942119-12-2;
Excluded Compound 13
CAS Registry Number: 872611-89-7;
Excluded Compound 14
CAS Registry Number: 872611-87-5;
Excluded Compound 15
CAS Registry Number: 792954-90-6;
Excluded Compound 16
CAS Registry Number: 341990-80-5;
Excluded Compound 17
CAS Registry Number: 341552-34-9;
Excluded Compound 18
CAS Registry Number: 341552-26-9;
Excluded Compound 19
CAS Registry Number: 341552-14-5;
Excluded Compound 20
CAS Registry Number: 150439-04-6;
Excluded Compound 21
CAS Registry Number: 150439-01-3;
Excluded Compound 22
CAS Registry Number: 150438-98-5;
Excluded Compound 23
CAS Registry Number: 150438-96-3;
Excluded Compound 24
CAS Registry Number: 150438-95-2; and
Excluded Compound 25
CAS Registry Number: 150438-94-1.

2. A compound according to formula VIII:

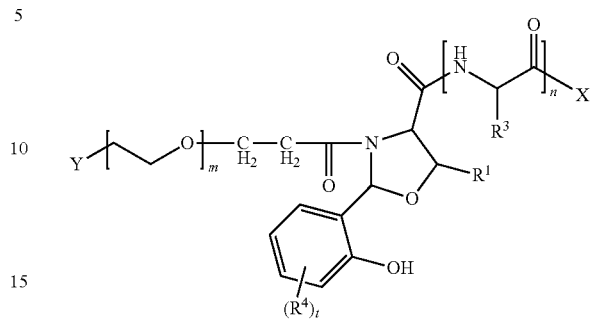

or a stereoisomer, a tautomer, or an isotopic variant thereof;
wherein
X is hydroxyl, alkoxy, amino or substituted amino;
Y is hydroxy, protected hydroxyl, amino or protected amino; or Y is —O—$R^2$, —O—C(O)—$R^2$, —NH—C(O)—$R^2$ or —NH—C(O)—O—$R^2$;
$R^1$ is H or methyl;
each $R^2$ is independently H, alkyl, or aryl;
each $R^3$ is independently selected from a group consisting of substituted or unsubstituted alkyl, substituted or unsubstituted alkenyl, substituted or unsubstituted alkynyl, substituted or unsubstituted alkoxy, substituted or unsubstituted aryl, and substituted or unsubstituted heteroaryl;
each $R^4$ is independently H or substituted or unsubstituted alkyl;
and
the subscript m is an integer from 2-200;
the subscript n is an integer from 2-1000;
the subscript t is 1, 2, 3, or 4.

3. The compound according to claim 1, wherein Y is
i) —O—$R^2$; and $R^2$ is H, Me, Et, i-Pr, n-Pr, or Ph;
ii) —O—C(O)—$R^2$; and —C(O)—$R^2$ is lauroyl, tridecanoyl, myristoyl, pentadecanoyl, palmitoyl, caproyl, benzoyl, cetyl, decyl, acetyl, phenyl acetyl, cyclohexyl acetyl, or valeroyl;
iii) —O—C(O)—$R^2$; and —C(O)—$R^2$ is glucuronyl;
iv) —O—C(O)-Me;
v) —NH—C(O)—$R^2$; and $R^2$ is Me, Et, i-Pr, or n-Pr; or
vi) NH-t-Boc or $NH_2$.

4. The compound according to claim 1, wherein Y is OH, OMe, —O—C(O)-Me, $NH_2$, or NH-t-Boc.

5. The compound according to claim 1, wherein $R^1$ is Me.

6. The compound according to claim 1, wherein each $R^3$ is independently
i) Me, Et, n-Pr, i-Pr, n-Bu, sec-Bu, or i-Bu;
ii) phenyl or benzyl, unsubstituted or substituted with one or more groups selected from alkyl, halo, hydroxy, amino, nitro, and alkoxy;
iii) phenethyl, unsubstituted or substituted with one or more groups selected from alkyl, halo, hydroxy, amino, nitro, and alkoxy;
iv) 2-naphthyl, unsubstituted or substituted with one or more groups selected from alkyl, halo, hydroxy, amino, nitro, and alkoxy;
v) 2,2-diphenylethyl, unsubstituted or substituted with one or more groups selected from alkyl, halo, hydroxy, amino, nitro, and alkoxy;

vi) furanyl or thienyl, unsubstituted or substituted with one or more groups selected from alkyl, halo, hydroxy, amino, nitro, and alkoxy;
vii) aminomethyl, 2-aminoethyl, 3-aminopropyl, 4-aminobutyl, 5-aminopentyl, or 6-aminohexyl;
viii) guanidinomethyl, 2-guanidinoethyl, 3-guanidinopropyl, 4-guanidinobutyl, 5-guanidinopentyl, or 6-guanidinohexyl;
ix) imidazolylmethyl, 2-imidazolylethyl, 3-imidazolylpropyl, 4-imidazolylbutyl, 5-imidazolylpentyl, or 6-imidazolylhexyl; or
x) methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

7. The compound according to claim 1, wherein $R^3$ is independently Me, i-Pr, i-Bu, sec-Bu, phenethyl, 4-hydroxyphenethyl, benzimidazol-3-ylmethyl, thiomethyl, methylthioethyl, hydroxymethyl, aminopropyl, guanadinopropyl, or imdazo-4-yl methyl.

8. The compound according to claim 2, wherein t is 4; and each of $R^4$ is H; or t is 1 or 2, and each of $R^4$ is independently Me, Et, i-Pr or $CF_3$.

9. The compound according to claim 1, wherein X is —OH, —OMe, —OEt, or $NH_2$.

10. The compound according to claim 1, wherein m is an integer between 2-200.

11. The compound according to claim 1, wherein n is an integer between 2-1000.

12. A pharmaceutical composition of a compound according to claim 1.

13. The compound according to claim 2, wherein Y is
i) —O—$R^2$; and $R^2$ is H, Me, Et, i-Pr, n-Pr, or Ph;
ii) —O—C(O)—$R^2$; and —C(O)—$R^2$ is lauroyl, tridecanoyl, myristoyl, pentadecanoyl, palmitoyl, caproyl, benzoyl, cetyl, decyl, acetyl, phenyl acetyl, cyclohexyl acetyl, or valeroyl;
iii) —O—C(O)—$R^2$; and —C(O)—$R^2$ is glucuronyl;
iv) —O—C(O)-Me;
v) —NH—C(O)—$R^2$; and $R^2$ is Me, Et, i-Pr, or n-Pr; or
vi) NH-t-Boc or $NH_2$.

14. The compound according to claim 2, wherein $R^1$ is Me.

15. The compound according to claim 2, wherein each $R^3$ is independently
i) Me, Et, n-Pr, i-Pr, n-Bu, sec-Bu, or i-Bu;
ii) phenyl or benzyl, unsubstituted or substituted with one or more groups selected from alkyl, halo, hydroxy, amino, nitro, and alkoxy;
iii) phenethyl, unsubstituted or substituted with one or more groups selected from alkyl, halo, hydroxy, amino, nitro, and alkoxy;
iv) 2-naphthyl, unsubstituted or substituted with one or more groups selected from alkyl, halo, hydroxy, amino, nitro, and alkoxy;
v) 2,2-diphenylethyl, unsubstituted or substituted with one or more groups selected from alkyl, halo, hydroxy, amino, nitro, and alkoxy;
vi) furanyl or thienyl, unsubstituted or substituted with one or more groups selected from alkyl, halo, hydroxy, amino, nitro, and alkoxy;
vii) aminomethyl, 2-aminoethyl, 3-aminopropyl, 4-aminobutyl, 5-aminopentyl, or 6-aminohexyl;
viii) guanidinomethyl, 2-guanidinoethyl, 3-guanidinopropyl, 4-guanidinobutyl, 5-guanidinopentyl, or 6-guanidinohexyl;
ix) imidazolylmethyl, 2-imidazolylethyl, 3-imidazolylpropyl, 4-imidazolylbutyl, 5-imidazolylpentyl, or 6-imidazolylhexyl; or
x) methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

16. The compound according to claim 2, wherein $R^3$ is independently Me, i-Pr, i-Bu, sec-Bu, phenethyl, 4-hydroxyphenethyl, benzimidazol-3-ylmethyl, thiomethyl, methylthioethyl, hydroxymethyl, aminopropyl, guanadinopropyl, or imdazo-4-yl methyl.

17. The compound according to claim 2, wherein X is —OH, —OMe, —OEt, or $NH_2$.

18. The compound according to claim 2, wherein Y is OH, OMe, —O—C(O)-Me, $NH_2$, or NH-t-Boc.

19. The compound according to claim 2, wherein m is an integer between 2-200.

20. The compound according to claim 2, wherein n is an integer between 2-1000.

21. The compound according to claim 1, wherein m is an integer between 2-50.

22. The compound according to claim 1, wherein m is an integer between 2-5.

23. The compound according to claim 1, wherein n is an integer between 2-100.

24. The compound according to claim 1, wherein n is an integer between 2-5.

25. The compound according to claim 2, wherein m is an integer between 2-50.

26. The compound according to claim 2, wherein m is an integer between 2-5.

27. The compound according to claim 2, wherein n is an integer between 2-100.

28. The compound according to claim 2, wherein n is an integer between 2-5.

* * * * *